US008084597B2

(12) United States Patent
Santner et al.

(10) Patent No.: US 8,084,597 B2
(45) Date of Patent: Dec. 27, 2011

(54) ARTIFICIAL ENTROPIC BRISTLE DOMAIN SEQUENCES AND THEIR USE IN RECOMBINANT PROTEIN PRODUCTION

(75) Inventors: Aaron A. Santner, Avon, IN (US);
Carrie Hughes Croy, Fishers, IN (US);
Farha Huseini Vasanwala, Carmel, IN (US); Vladimir N. Uversky, Carmel, IN (US); A. Keith Dunker, Indianapolis, IN (US)

(73) Assignee: Molecular Kinetics Incorporated, Indianpolis, IN (US)

( * ) Notice: Subject to any disclaimer, the term of this patent is extended or adjusted under 35 U.S.C. 154(b) by 0 days.

(21) Appl. No.: 12/886,280

(22) Filed: Sep. 20, 2010

(65) Prior Publication Data

US 2011/0117599 A1 May 19, 2011

Related U.S. Application Data

(63) Continuation-in-part of application No. 12/272,558, filed on Nov. 17, 2008.

(60) Provisional application No. 60/988,319, filed on Nov. 15, 2007.

(51) Int. Cl.
*C07H 21/04* (2006.01)
*C12P 21/04* (2006.01)
(52) U.S. Cl. ..................... 536/23.4; 435/69.7
(58) Field of Classification Search .................. None
See application file for complete search history.

(56) References Cited

OTHER PUBLICATIONS

Harris et al. (Journal of Neuroscience Research, 30: 47-62 (1991)).*
Abrahmsen et al., "Secretion of heterologous gene products to the culture medium of *Escherichia coli*," Nucleic Acids Research 14(18): 7487-7500, 1986.
Braun et al., "Proteome-scale purification of human proteins from bacteria," Procedure of National Academy of Sciences USA 99(5): 2654-2659, Mar. 5, 2002.
Dunker et al., "Intrinsically disordered protein," Journal of Molecular Graphics and Modelling 19(1): 26-59, 2001.
Dyson et al, "Production of soluble mammalian proteins in *Escherichia coli*: identification of protein features that correlate with successful expression," BMC Biotechnology 4(1): 32, Dec. 14, 2004.
Fox et al., "Maltodextrin-binding proteins from diverse bacteria and archaea are potent solubility enhancers," FEBS Letters 537: 53-57, 2003.
Gottesman et al., "Deg Phenotype of *Escherichia coli* Ion Mutants," Journal of Bacteriology 133(2): 844-851, Feb. 1978.

Hammarström, et al., "Rapid screening for improved solubility of small human proteins produced as fusion proteins in *Escherichia coli*," Protein Science 11: 313-321, 2002.
Hoh, J.H., "Functional Protein Domains From the Thermally Driven Motion of Polypeptide Chains: A Proposal," Proteins: Structure, Function, and Genetics 32(2): 223-228, Aug. 1, 1998.
Itakura et al., "Expression in *Escherichia coli* of a Chemically Synthesized Gene for the Hormone Somatostatin," Science 198: 1056-1063, Dec. 9, 1977.
Kapust et al., "*Escherichia coli* maltose-binding protein is uncommonly effective at promoting the solubility of polypeptides to which it is fused," Protein Science 8: 1668-1674, 1999.
Kataeva et al., "Improving Solubility of *Shewanella oneidensis* MR-1 and *Clostridium thermocellum* JW-20 Proteins Expressed into *Esherichia coli*," Journal of Proteome Research 4(6): 1942-1951, 2005.
Milner, S.T., "Polymer Brushes," Science 251: 905-914, Feb. 22, 1991.
Napper, D.H., "Polymeric Stabilization of Colloidal Dispersions: Stabilization by Attached Polymer: Steric Stabilization," Academic Press, London, 1983, pp. 18-30.
Nilsson et al., "Immobilization and purification of enzymes with staphylococcal protein a gene fusion vectors," EMBO Journal 4(4): 1075-1080, 1985.
Richarme et al., "Chaperone Properties of the Bacterial Periplasmic Substrate-binding Proteins," Journal of Biological Chemistry 272(25): 15607-15612, Jun. 20, 1997.
Romero et al., "Sequence Complexity of Disordered Protein," Proteins: Structure, Function, and Genetics 42(1): 38-48, 2001.
Sachdev et al., "Fusions to Maltose-Binding Protein: Control of Folding and Solubility in Protein Purification," Methods in Enzymology 326: 312-321, 2000.
Shen, S., "Multiple joined genes prevent product degradation in *Escherichia coli*," Proceedings of the National Academy of Sciences USA 81:4627-4631, Aug. 1984.
Sickmeier et al., "DisProt: the Database of Disordered Proteins," Nucleic Acids Research 35: D786-D793, 2007.
Smith, D.B., "Generating Fusions to Glutathione S-Transferase for Protein Studies," Methods in Enzymology 326: 254-270, 2000.
Takagi et al., "Characterization of DNA Polymerase from *Pyrococcus* sp. Strain KOD1 and Its Application to PCR," Applied and Environmental Microbiology 63(11): 4504-4510, 1997.
Vaillancourt et al., "Recovery of Polypeptides Cleaved from Purified Calmodulin-Binding Peptide Fusion Proteins," BioTechniques 22(3): 451-453, Mar. 1997.
Vucetic et al., "DisProt: a database of protein disorder," BioInformatics 21(1): 137-140, 2005.
Zhan et al., "Structural analysis of regulatory protein domains using GST-fusion proteins," Gene 281: 1-9, 2001.

* cited by examiner

*Primary Examiner* — Suzanne M Noakes
*Assistant Examiner* — Jae W Lee
(74) *Attorney, Agent, or Firm* — Seed IP Law Group PLLC

(57) ABSTRACT

Compositions and methods for recombinant protein production and, more particularly, fusion polypeptides, polynucleotides encoding fusion polypeptides, expression vectors, kits, and related methods for recombinant protein production.

22 Claims, 9 Drawing Sheets psxspsxppdpsxppdpsxppdpsxxpdpsppdpsxppdpsppppdpsp**XsppXpp

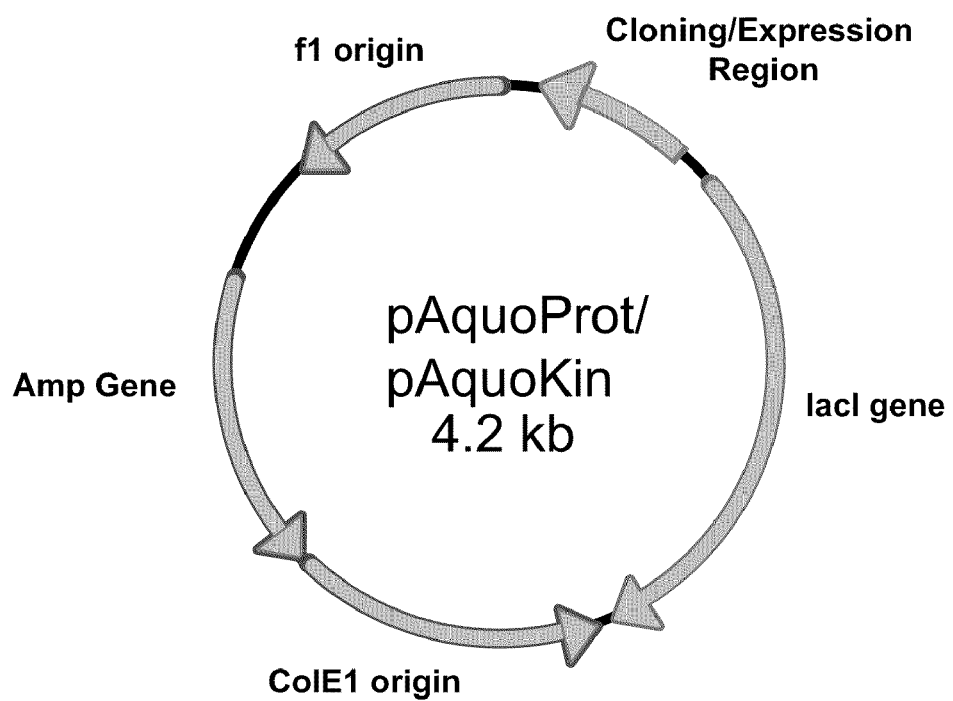
Figure 5: pAquoProt and pAquoKin Vector Map

Figure 6: Cloning and expression region of pAquoProt vector

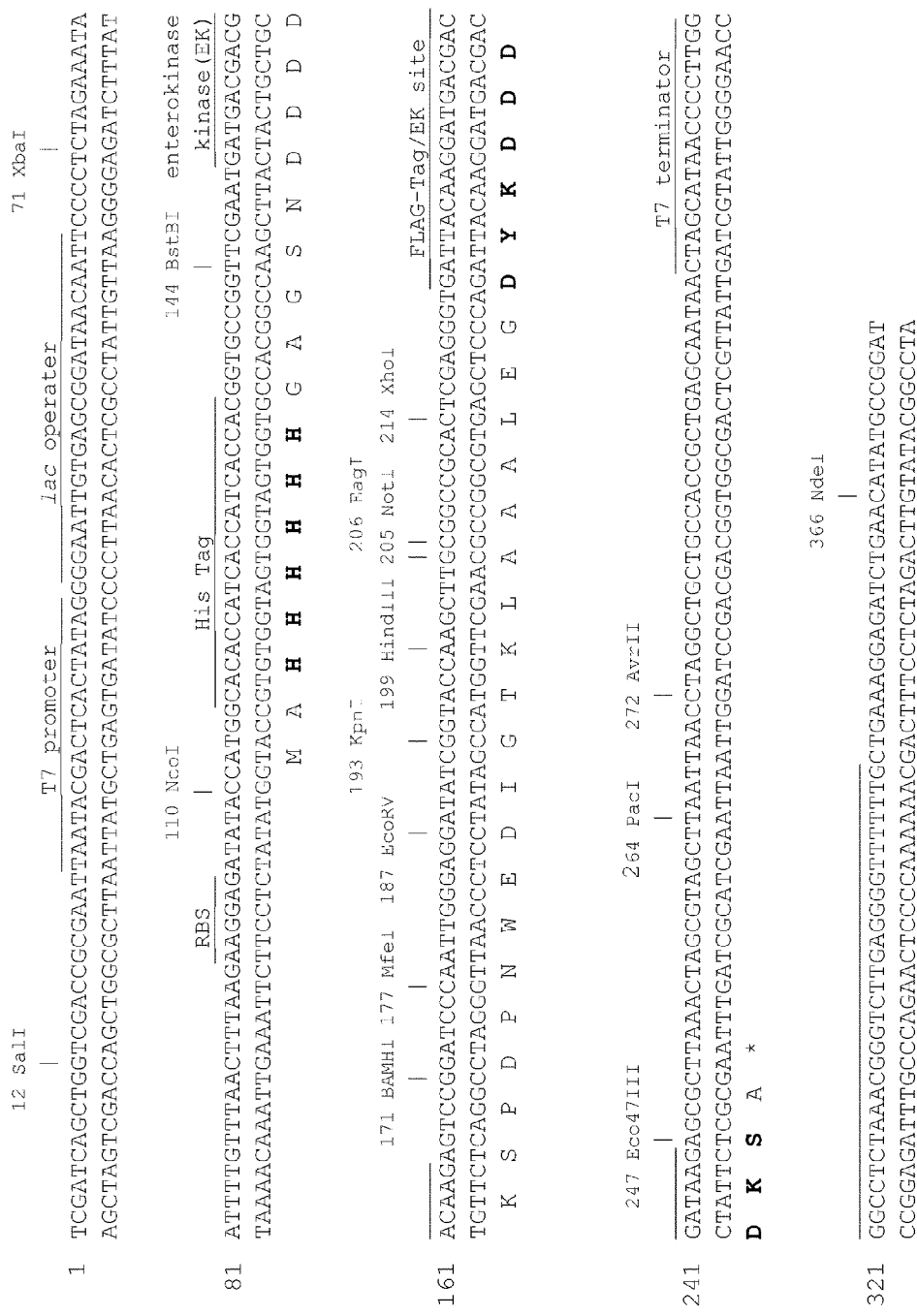
Figure 7: Cloning and expression region of pAquoKin vector

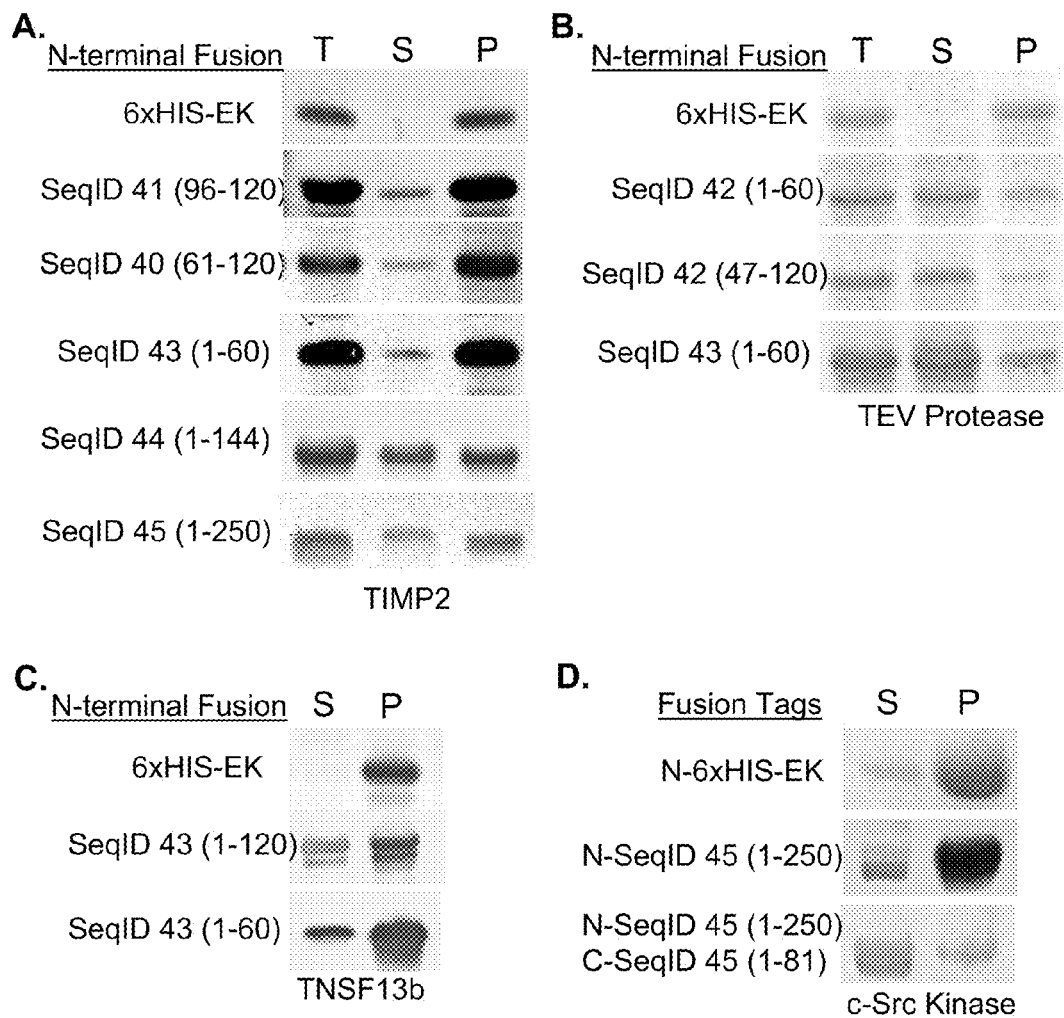
Figure 8: EBD-fusions Promote Target Protein Solubility.

ARTIFICIAL ENTROPIC BRISTLE DOMAIN SEQUENCES AND THEIR USE IN RECOMBINANT PROTEIN PRODUCTION

CROSS-REFERENCE TO RELATED APPLICATION

This application is a continuation-in-part of U.S. patent application Ser. No. 12/272,558, filed Nov. 17, 2008, which application claims the benefit under 35 U.S.C. §119(e) of U.S. Provisional Patent Application No. 60/988,319, filed Nov. 15, 2007; where these applications are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 670098_406C1b SEQUENCE_LISTING.txt. The text file is 173 KB, was created on Jan. 27, 2011 and is being submitted electronically via EFS-Web.

FIELD OF THE INVENTION

The present invention relates generally to compositions and methods for improved recombinant protein production and, more particularly, to fusion polypeptides, polynucleotides encoding fusion polypeptides, expression vectors, kits, and related methods for recombinant protein production.

DETAILED DESCRIPTION OF THE RELATED ART

A large percentage of the proteins identified via the different genome sequencing effort have been difficult to express and/or purify as recombinant proteins using standard methods. For example, a trial study using *Methanobacterium thermoautotrophicum* as a model system identified a number of problems associated with high throughput structure determination (Christendat et al. (2000) *Prog. Biophys. Mol. Biol.* 73(5): 339-345; Christendat et al. (2000) *Nat Struct Biol* 7(10): 903-909). The complete list of genome-encoded proteins was filtered to remove proteins with predicted transmembrane regions or homologues to known structures. When these filtered proteins were taken through the cloning, expression, and structural determination steps of a high throughput process, only about 50% of the selected proteins could be purified in a state suitable for structural studies, with roughly 45% of large expressed proteins and 30% of small expressed proteins failing due to insolubility. The study concluded that considerable effort must be invested in improving the attrition rate due to proteins with poor expression levels and unfavorable biophysical properties. (Christendat et al. (2000) *Prog. Biophys. Mol. Biol.* 73(5): 339-345; Christendat et al. (2000) *Nat Struct Biol* 7(10): 903-909).

Similar results have been observed for other prokaryotic proteomes. One study reported the successful cloning and attempted expression of 1376 (73%) of the predicted 1877 genes of the *Thermotoga maritima* proteome. However, crystallization conditions were able to be determined for only 432 proteins (23%). A significant component of the decrease between the cloned and crystallized success levels was due to poor protein solubility and stability (Kuhn et al. (2002) *Proteins* 49(1): 142-5).

Similarly low success rates have been reported for eukaryotic proteomes. A study of a sample set of human proteins, for example, reported that the failure rate using high-throughput methods for three classes of proteins based on cellular location was 50% for soluble proteins, 70% for extracellular proteins, and more than 80% for membrane proteins (Braun et al. (2002) *Proc Natl Acad Sci USA* 99(5): 2654-9).

Interactions between individual recombinant proteins are responsible for a significant number of the previously mentioned failures. In a high-throughput structural determination study, Christendat and colleagues found that 24 of 32 proteins that were classified by nuclear magnetic resonance as aggregated displayed circular dichroism spectra consistent with stable folded proteins, suggesting that these proteins were folded properly but aggregated due to surface interactions (Christendat et al. (2000) *Prog. Biophys. Mol. Biol.* 73(5): 339-345). One possible explanation for this is that these proteins function in vivo as part of multimeric units but when they are recombinantly expressed, dimerization domains are exposed that mediate protein-protein interactions.

Prior methods used to increase recombinant protein stability include production in *E. coli* strains that are deficient in proteases (Gottesman and Zipser (1978) *J Bacteriol* 133(2): 844-51) and production of fusions of bacterial protein fragments to a recombinant polypeptide/protein of interest (Itakura et al., *Science,* 1977. 198:1056-63; Shen, *Proc Natl Acad Sci USA,* 1984. 81:4627-31). It has also been attempted to stabilize foreign proteins in *E. coli*. In addition, fusing a leader sequence to a recombinant protein may cause a gene product to accumulate in the periplasm or be excreted, which may result in increased recovery of properly folded soluble protein (Nilsson et al., *EMBO J,* 1985. 4:1075-80; Abrahmsen et al., *Nucleic Acids Res,* 1986. 14:7487-500). These strategies have advantages for some proteins but they generally do not succeed when used, for example, with membrane proteins or proteins capable of strong protein-protein interactions.

Fusion polypeptides have also been used as an approach for improving the solubility and folding of recombinant polypeptides/proteins produced in *E. coli* (Zhan et al., Gene, 2001. 281:1-9). Some commonly used fusion partners which have been linked to heterologous protein sequences of interest include calmodulin-binding peptide (CBP) (Vaillancourt et al., *Biotechniques,* 1997. 22:451-3), glutathione-S-transferase (GST) (Smith, *Methods Enzymol,* 2000. 326:254-70), thioredoxin (TRX) (Martin Hammarström et al., *Protein Science,* 2002. 11:313-321), and maltose-binding protein (MBP) (Sachdev et al., *Methods Enzymol,* 2000. 326:312-21). Glutathione-S-transferase and maltose-binding protein have been found to increase the recombinant protein purification success rate when fused to a heterologous sequence in a controlled trial of 32 human test proteins (Braun et al., *Proc Natl Acad Sci USA,* 2002. 99:2654-9). Further, maltose-binding protein domain fusions have been shown to increase the solubility of recombinant proteins (Kapust et al., *Protein Sci,* 1999. 8:1668-74; Braun et al., *Proc Natl Acad Sci USA,* 2002. 99:2654-9; Martin Hammarström et al., *Protein Science,* 2002. 11:313-321). Maltose-binding protein may further benefit recombinant protein solubility and folding in that it may have chaperone-like properties that assist in folding of the fusion partner (Richarme et al., *J Biol Chem,* 1997. 272: 15607-12; Bach et al., *J Mol Biol,* 2001. 312:79-93. However, these fusion approaches used to date have not been amendable to all classes of proteins, and have thus met with only limited success.

Entropic bristles have been used in a variety of polymers to reduce aggregation of small particles such as latex particles in paints and to stabilize a wide variety of other colloidal products (Hoh, *Proteins,* 1998. 32:223-228). Entropic bristles generally comprise amino acid residues that do not have a tendency to form secondary structure and in the process of random motion about their attachment points sweep out a significant region in space and entropically exclude other molecules by their random motion (Hoh, *Proteins,* 1998. 32:223-228). Entropic bristles are singular elements, comprising highly flexible, non-aggregating polymer chains, of which entropic brushes are assembled. In polymer chemistry, entropic bristles have been affixed to the surfaces of particles (e.g. latex beads), thereby forming entropic brushes which, in turn, prevent particle aggregation (*Stabilization by attached polymer: steric stabilization,* in *Polymeric stabilization of colloidal dispersions,* D. H. Napper, Editor. 1983, Academic Press: London. p. 18-30). EBDs can exclude large molecules but do not exclude small molecules such as water, salts, metal ions, or cofactors (Hoh, *Proteins,* 1998. 32:223-228).

EBDs can also function as steric stabilizers and operate through steric hindrance stabilization (*Stabilization by attached polymer: steric stabilization,* in *Polymeric stabilization of colloidal dispersions,* D. H. Napper, Editor. 1983, Academic Press: London. p. 18-30). Naper described characteristics that contribute to steric stabilization functions, including (1) they have an amphipathic sequence; (2) they are attached to the colloidal particle by one end rather than being totally adsorbed; (3) they are soluble in the medium used; (4) they are mutually repulsive; (5) they are thermodynamically stable; and (6) they exhibit stabilizing ability in proportion to their length. Steric stabilizers intended to function in aqueous media extend from the surface of colloidal molecules thus transforming their surfaces from hydrophobic to hydrophilic. The fact that sterically stabilized particles are thermodynamically stable leads them to spontaneously re-disperse when dried residue is reintroduced to solvent. Entropic bristles can adopt random-walk configurations in solution (Milner, *Science,* 1991. 251:905-914). These chains extend from an attachment point because of their affinity for the solvent. This affinity is due in part to the highly charged nature of the entropic bristle sequence.

While naturally-occurring EBDs possess features desirable for use in improving the solubility, folding, etc., of recombinant proteins, prior attempts at using EBD sequences in fusion with heterologous protein sequences have met with limited success, due in part to cellular toxicity associated with the naturally occurring EBDs. Accordingly, there remains a need for new compositions and methods for improving the properties and characteristics of recombinant proteins, e.g., improving solubility, stability, yield and/or folding of recombinant proteins. The present invention addresses these needs and offers other related advantages by providing non-naturally occurring EBD sequences as fusion partners for use in recombinant protein production techniques, as described herein.

SUMMARY OF THE INVENTION

According to a general aspect of the present invention, there are provided isolated fusion polypeptides comprising at least one artificial, non-naturally occurring entropic bristle domain (EBD) sequence and at least one heterologous polypeptide sequence of interest. The fusion polypeptides comprising artificial EBD sequences as described herein offer a number of advantages over prior fusion polypeptides and methods relating thereto. For example, the fusion polypeptides of the invention offer increased solubility relative to the heterologous polypeptide sequence, reduced aggregation relative to the heterologous polypeptide sequence and/or improved folding relative to the heterologous polypeptide sequence.

In one illustrative embodiment, the invention provides fusion polypeptides comprising at least one non-naturally occurring entropic bristle domain (EBD) polypeptide sequence and at least one heterologous polypeptide sequence to be expressed, wherein the EBD polypeptide sequence is about 10-1000 amino acid residues in length, and wherein at least 75% of the residues of the EBD polypeptide sequence are selected from G, D, M, K, R, S, Q, P, and E. In other embodiments, at least 80, 85, 90 or 95% of the residues of the EBD polypeptide sequence are selected from G, D, M, K, R, S, Q, P, and E.

In another illustrative embodiment, the EBD polypeptide sequence is positively charged and the amino acid residues which make up the EBD polypeptide comprise disorder-promoting amino acid residues selected from P, Q, S and K. In a more specific embodiment, the disorder-promoting amino acid residues P, Q, S and K are present in about the following amino acid ratios: K:P:Q:S=1:2:1:1, K:P:Q:S=1:4:1:1, K:P:Q:S=2:2:1:1, K:P:Q:S=3:2:1:1, K:P:Q:S=1:2:1:2, K:P:Q:S=2:2:1:2, K:P:Q:S=3:2:1:2, K:P:Q:S=4:2:1:2, or K:P:Q:S=5:2:1:2. In a more specific embodiment, the EDB polypeptide sequence comprises a sequence set forth in SEQ ID NO: 1, SEQ ID NO: 2, SEQ ID NO: 3, SEQ ID NO: 4, SEQ ID NO: 5, SEQ ID NO: 23, or SEQ ID NO: 24, or a fragment thereof, or a sequence having at least 90% identity thereto.

In another illustrative embodiment, the EBD polypeptide sequence is negatively charged and the amino acid residues are disorder-promoting amino acid residues selected from P, Q, S and E. In a more specific embodiment, the disorder-promoting amino acid residues P, Q, S and E are present in about the following amino acid ratios: E:P:Q:S=1:2:1:1, E:P:Q:S=1:4:1:1, E:P:Q:S=2:2:1:1, E:P:Q:S=3:2:1:1, E:P:Q:S=1:2:1:2, E:P:Q:S=2:2:1:2, E:P:Q:S=3:2:1:2, E:P:Q:S=4:2:1:2, or E:P:Q:S=5:2:1:2. In a more specific embodiment, the EDB polypeptide comprises the sequence set forth in SEQ ID NO: 6, SEQ ID NO: 7, SEQ ID NO: 8, SEQ ID NO: 9, SEQ ID NO: 10, SEQ ID NO: 25, SEQ ID NO: 26, SEQ ID NO: 38, SEQ ID NO: 39, SEQ ID NO: 40, or a fragment thereof, or a sequence having at least 90% identity thereto.

In another illustrative embodiment, the EBD polypeptide sequence is negatively charged and the amino acid residues are disorder-promoting amino acid residues selected from P, Q, G and E. In a more specific embodiment, the disorder-promoting amino acid residues P, Q, G and E are present in about the following amino acid ratios: E:P:Q:G=1:2:1:1, E:P:Q:G=1:4:1:1, E:P:Q:G=2:2:1:1, E:P:Q:G=3:2:1:1, E:P:Q:G=1:2:1:2, E:P:Q:G=2:2:1:2, E:P:Q:G=3:2:1:2, E:P:Q:G=4:2:1:2, or E:P:Q:G=5:2:1:2. In a more specific embodiment, the EDB polypeptide comprises the sequence set forth in SEQ ID NO: 41, SEQ ID NO: 42, SEQ ID NO: 43, or a fragment thereof, or a sequence having at least 90% identity thereto.

In another illustrative embodiment, the EBD polypeptide sequence is negatively charged and the amino acid residues are disorder-promoting amino acid residues selected from P, Q, S, G, D and E. In a more specific embodiment, the disorder-promoting amino acid residues P, Q, S, G, D and E are present in about the following amino acid ratios: D:E:P:Q:S:G=1:2:3:1:2:1. In a more specific embodiment, the EDB polypeptide comprises the sequence set forth in SEQ ID NO: 44, or a fragment thereof, or a sequence having at least 85% identity thereto such as the sequence set forth in SEQ ID NO: 45.

In yet another illustrative embodiment, the EBD polypeptide sequence is neutral and the disorder-promoting residues are selected from P, Q, S and G. In a more particular embodiment, the amino acid residues P, Q, S and G are present in about the amino acid ratio of G:P:Q:S=1:2:1:2. In a more particular embodiment, the EDB polypeptide comprises the sequence set forth in SEQ ID NO: 11, SEQ ID NO: 27, or SEQ ID NO: 28, or a fragment thereof, or a sequence having at least 90% identity thereto.

In another illustrative embodiment, the EBD polypeptide sequence is positively charged and the amino acid residues are disorder-promoting amino acid residues selected from P, Q, S and R. In a more specific embodiment, the amino acid residues R, P, Q and S are present in about the following amino acid ratios: R:P:Q:S=1:2:1:2, R:P:Q:S=2:2:1:2, R:P:Q:S=3:2:1:2, R:P:Q:S=4:2:1:2, or R:P:Q:S=5:2:1:2.

In another illustrative embodiment, the EBD polypeptide sequence is negatively charged and the amino acid residues are disorder-promoting amino acid residues are selected from P, Q, S and D. In a more particular embodiment, the amino acid residues D, P, Q and S are present in about the following amino acid ratios: D:P:Q:S=1:2:1:2, D:P:Q:S=2:2:1:2, D:P:Q:S=3:2:1:2, D:P:Q:S=4:2:1:2, or D:P:Q:S=5:2:1:2.

A fusion polypeptide of the invention, comprising an EBD sequence and a heterologous polypeptide sequence, exhibits improved solubility relative to the corresponding heterologous polypeptide in the absence of the EBD sequence. In a related embodiment, the fusion polypeptide has at least 5% increased solubility relative to the heterologous polypeptide sequence, at least 25% increased solubility relative to the heterologous polypeptide sequence, or at least 50% increased solubility relative to the heterologous polypeptide sequence.

In another embodiment, a fusion polypeptide of the invention exhibits reduced aggregation relative to the level of aggregation of the heterologous polypeptide sequence in the absence of the EBD sequence. For example, a fusion polypeptide of the invention generally exhibits at least 10% reduced aggregation relative to the heterologous polypeptide sequence or at least 25% reduced aggregation relative to the heterologous polypeptide sequence.

In another embodiment, a fusion polypeptide of the invention exhibits improved self-folding relative to the heterologous polypeptide sequence in the absence of the EBD sequence.

In another embodiment of the present invention, an EBD sequence employed in a fusion polypeptide comprises an amino acid sequence that maintains a substantially random coil conformation.

In another embodiment, the EBD sequence of a fusion polypeptide of the invention comprises an amino acid sequence that is substantially mutually repulsive.

In another embodiment, the EBD sequence of a fusion polypeptide of the invention comprises an amino acid sequence that remains in substantially constant motion.

In another embodiment of the present invention, the EBD sequence of a fusion polypeptide of the invention is a random sequence of disorder-promoting amino acid residues.

The EBD sequence of a fusion polypeptide of the invention generally comprises between about 5 to 1000 amino acid residues, 5 to 500 amino acid residues, 5 to 400 amino acid residues, 5 to 300 amino acid residues, 5 to 200 amino acid residues, 5 to 100 amino acid residues, 5 to 80 amino acid residues, 5 to 60 amino acid residues, 5 to 40 amino acid residues, 5 to 30 amino acid residues, 5 to 20 amino acid residues, 10 to 30 amino acid residues, 15 to 25 amino acid residues, 10 to 90 amino acid residues, 20 to 80 amino acid residues, 20 to 40 amino acid residues, 30 to 70 amino acid residues, or 40 to 60 amino acid residues.

In a related embodiment, the disorder-promoting EBD sequence comprises no more than about 20 amino acid residues, 30 amino acid residues, 40 amino acid residues, 50 amino acid residues, 100 amino acid residues, 200 amino acid residues, 300 amino acid residues, 400 amino acid residues, 500 amino acid residues, or 1000 amino acid residues.

In yet another related embodiment, the EBD sequence of a fusion polypeptide of the invention comprises at least 2-100 repeats of an EBD sequence set forth above or described herein, or a combination thereof.

In another embodiment, the EBD sequence of a fusion polypeptide of the invention comprises a combination of any one or more of fragments derived from disorder-promoting EBD sequences that are positively charged, negatively charges, or neutral as set here herein.

In another embodiment, an EBD sequence of a fusion polypeptide of the invention is cleavable, e.g., can be removed and/or separated from the heterologous polypeptide sequence after recombinant expression by, for example, enzymatic or chemical cleavage methods.

In another embodiment, an EBD sequence of a fusion polypeptide of the invention is covalently linked at the N-terminus of the heterologous polypeptide sequence of interest. In another embodiment, an EBD sequence of a fusion polypeptide of the invention is covalently linked at the C-terminus of the heterologous polypeptide sequence of interest. In yet another embodiment, an EBD sequence of a fusion polypeptide of the invention is covalently linked at the N- and C-termini of the heterologous polypeptide sequence of interest.

In another embodiment of the invention, the charge of an EBD sequence of a fusion polypeptide of the invention is modulated by, for example, enzymatic and/or chemical methods, in order to modulate the activity of the EBD sequence. In a particular embodiment, the charge of the EBD sequence is modulated by phosphorylation.

According to another aspect of the invention, an isolated polynucleotide is provided, wherein the polynucleotide encodes a fusion polypeptide as described herein or an artificial EBD sequence as described herein.

According to yet another aspect of the invention, there is provided an expression vector comprising an isolated polynucleotide encoding a fusion polypeptide as described herein or an artificial EBD sequence as described herein. In a related embodiment, an expression vector is provided comprising a polynucleotide encoding an EBD sequence and further comprising a cloning site for insertion of a polynucleotide encoding a heterologous polypeptide of interest.

According to yet another aspect of the invention, there is provided a host cell comprising an expression vector as described herein.

According to yet another aspect of the invention, there is provided a kit comprising an isolated polynucleotide as described herein, an isolated polypeptide as described herein and/or an isolated host cell as described herein.

Yet another aspect of the invention provides a method for producing a recombinant protein comprising the steps of: introducing into a host cell an expression vector comprising a polynucleotide sequence encoding a fusion polypeptide, the fusion polypeptide comprising at least one EBD sequence and at least one polypeptide sequence of interest; and expressing the fusion polypeptide in the host cell. In another embodiment, the method further comprises the step of isolating the fusion polypeptide from the host cell. In another related embodiment, the method further comprises the step of removing the EBD sequence from the fusion polypeptide before or after isolating the fusion polypeptide from the host cell.

These and other aspects of the present invention will become apparent upon reference to the following detailed description. All references disclosed herein and in the enclosed Application Data Sheet are hereby incorporated by reference in their entirety as if each was incorporated individually.

BRIEF DESCRIPTION OF THE DRAWINGS

FIGS. 2A and 2B. Amino acid sequence of the randomly generated artificial EB containing the chosen residues in the following proportion: X:P:Q:S=1:2:1:2 (SEQ ID NO:35); X=K, E or G (2A) and sequences of positive, negative and neutral bristles, indicated as EB. (SEQ ID NO:24), EB. (SEQ ID NO:26) and $EB_0$ (SEQ ID NO:28)(2B), respectively. The actual X:P:Q:S ratios for these sequences was 5:8:6:11, numbers that are close to the 1:2:1:2 used to generate the sequences.

FIG. 5. Vector map of the pAquoProt and pAquoKin *E. coli* expression plasmids that have been created to harbor entropic bristles. The pAquoProt and pAquoKin vectors are identical except within the expression/cloning region.

FIG. 6. Double stranded sequence of the expression/cloning region of the pAquoProt plasmid (SEQ ID NOS: 54 and 55). The expression/cloning region is comprised of the T7 promoter/operator, ribosomal binding site (RBS), coding sequences for a 6× His tag and enterokinase (EK) cleavage site, multicloning site, coding sequences for HA epitope tag, and T7 terminator (SEQ ID NO:56). The restriction enzymes listed are unique sites not present elsewhere in the plasmid. Entropic bristle domain coding sequences are introduced into the expression/cloning region at the BstBl site positioned between the 6× His tag and EK cleavage coding sequences.

FIG. 7. Double stranded sequence of the expression/cloning region of the pAquoKin plasmid (SEQ ID NOS: 57 and 58). The expression/cloning region is comprised of the T7 promoter/operator, ribosomal binding site (RBS), coding sequences for a 6× His tag and enterokinase cleavage site, multicloning site, coding sequences for the FLAG™ epitope tag, and T7 terminator (SEQ ID NO:59). The restriction enzymes listed are unique sites not present elsewhere in the plasmid. Entropic bristle domain coding sequences are introduced into the pAquoKin expression/cloning region at the BstBl site positioned between the 6× His tag and EK cleavage coding sequences and at the Eco47III site following the C-terminal FLAG™ coding sequence.

FIGS. 8A, 8B, 8C, and 8D. Expression and solubility of TIMP2 with a variety of N-terminal entropic bristles ranging in length from 24 to 250 amino acids or 6× His-EK control fusion (8A). Expression and solubility of TEV protease fused with 3 EBDs that are comprised of the same amino acids but have distinct primary amino acid sequences (8B). Expression and solubility of TNSF13b fused with a 120 amino acid EBD or a 60 amino acid fragment (8C). Expression and solubility of c-Src kinase with an N-terminal fusion or N- and C-terminal EBD fusions. c-Src with entropic bristles fused to both termini is more soluble than N-terminal c-Src fusions (8D). Abbreviations: T, total protein, S, soluble protein, P, insoluble pellet protein. IDs of solubilized proteins are shown below each set of blots.

BRIEF DESCRIPTION OF THE SEQUENCE IDENTIFIERS

Figure 1:
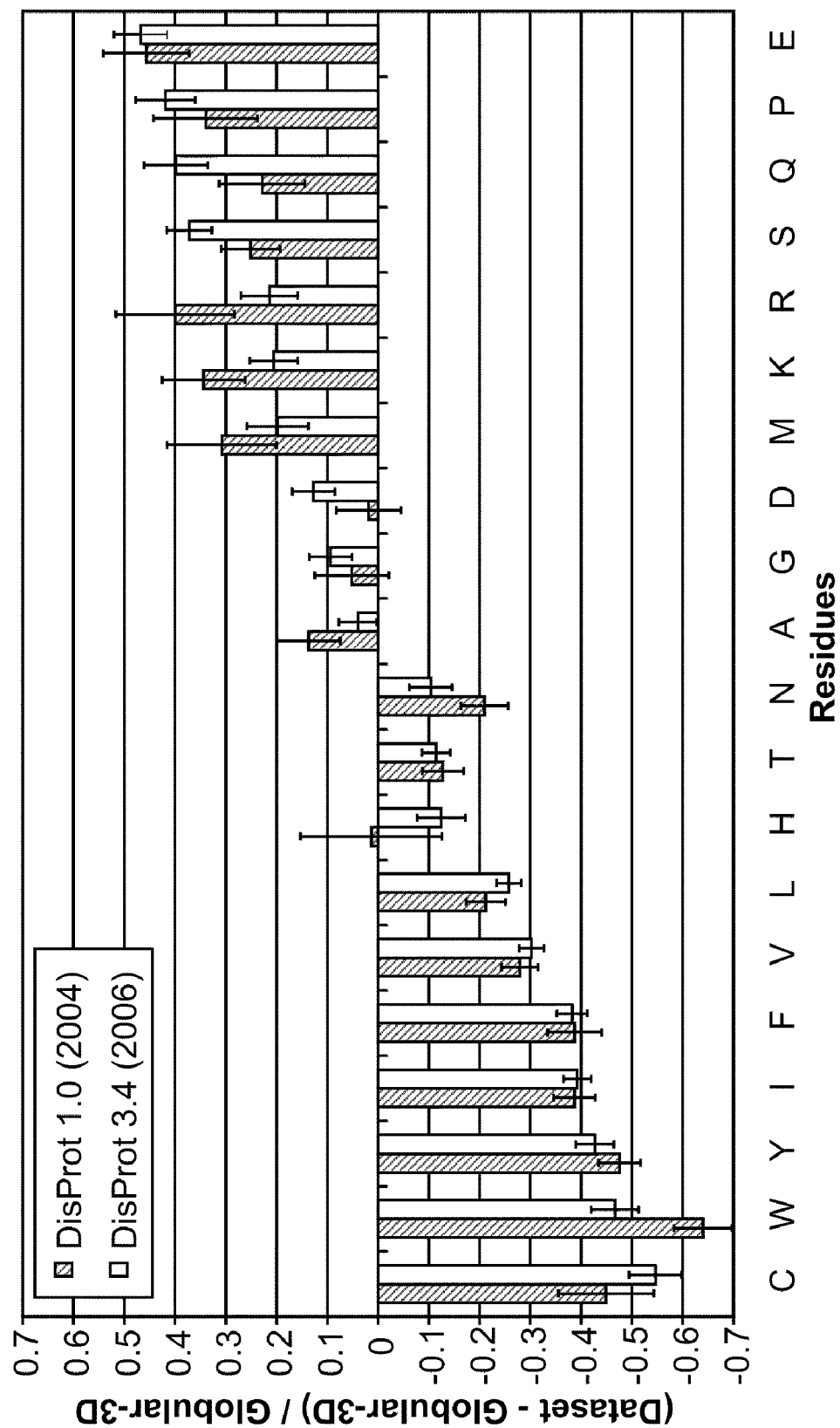
FIG. 1. Amino acid composition, relative to the set of globular proteins Globular-3D, of intrinsically disordered regions 10 residues or longer from the DisProt database. Slanted hash marks indicate DisProt 1.0 (152 proteins), while white indicates DisProt 3.4 (460 proteins). Amino acid compositions were calculated per disordered regions and then averaged. The arrangement of the amino acids is by peak height for the DisProt 3.4 release. Confidence intervals were estimated using per-protein bootstrapping with 10,000 iterations.

SEQ ID NO: 1 is the amino acid sequence of a positively charged EBD domain, EBD(+), which is a random sequence containing disorder-promoting residues P, Q, S and K in about the following amino acid ratios: K:P:Q:S=1:2:1:2. The sequence was produced using the random sequence generator tool located at the Swiss-Prot website: au.expasy.org/tools/randseq.html.

SEQ ID NO: 2 is the amino acid sequence of a positively charged EBD domain, EBD(++), which is a random sequence containing disorder-promoting residues P, Q, S and K in about the following amino acid ratios: K:P:Q:S=2:2:1:2. The sequence was produced using the random sequence generator tool located at the Swiss-Prot website: au.expasy.org/tools/randseq.html.

SEQ ID NO: 3 is the amino acid sequence of a positively charged EBD domain, EBD(+++), which is a random sequence containing disorder-promoting residues P, Q, S and K in about the following amino acid ratios: K:P:Q:S=3:2:1:2. The sequence was produced using the random sequence generator tool located at the Swiss-Prot website: au.expasy.org/tools/randseq.html.

SEQ ID NO: 4 is the amino acid sequence of a positively charged EBD domain, EBD(++++), which is a random sequence containing disorder-promoting residues P, Q, S and K in about the following amino acid ratios: K:P:Q:S=4:2:1:2. The sequence was produced using the random sequence generator tool located at the Swiss-Prot website: au.expasy.org/tools/randseq.html.

SEQ ID NO: 5 is the amino acid sequence of a positively charged EBD domain, EBD(+++++), which is a random sequence containing disorder-promoting residues P, Q, S and K in about the following amino acid ratios: K:P:Q:S=5:2:1:2. The sequence was produced using the random sequence generator tool located at the Swiss-Prot website: au.expasy.org/tools/randseq.html.

SEQ ID NO: 6 is the amino acid sequence of a negatively charged EBD domain, EBD(-), which is a random sequence containing disorder-promoting residues P, Q, S and E in about the following amino acid ratios: E:P:Q:S=1:2:1:2. The sequence was produced using the random sequence generator tool located at the Swiss-Prot website: au.expasy.org/tools/randseq.html.

SEQ ID NO: 7 is the amino acid sequence of a negatively charged EBD domain, EBD(--), which is a random sequence containing disorder-promoting residues P, Q, S and E in about the following amino acid ratios: E:P:Q:S=2:2:1:2. The sequence was produced using the random sequence generator tool located at the Swiss-Prot website: au.expasy.org/tools/randseq.html.

SEQ ID NO: 8 is the amino acid sequence of a negatively charged EBD domain, EBD(---), which is a random sequence containing disorder-promoting residues P, Q, S and E in about the following amino acid ratios: E:P:Q:S=3:2:1:2. The sequence was produced using the random sequence generator tool located at the Swiss-Prot website: au.expasy.org/tools/randseq.html.

SEQ ID NO: 9 is the amino acid sequence of a negatively charged EBD domain, EBD(----), which is a random sequence containing disorder-promoting residues P, Q, S and E in about the following amino acid ratios: E:P:Q:S=4:2:1:2. The sequence was produced using the random sequence generator tool located at the Swiss-Prot website: au.expasy.org/tools/randseq.html.

SEQ ID NO: 10 is the amino acid sequence of a negatively charged EBD domain, EBD(-----) which is a random sequence containing disorder-promoting residues P, Q, S and E in about the following amino acid ratios: E:P:Q:S=5:2:1:2. The sequence was produced using the random sequence generator tool located at the Swiss-Prot website: http://au.expasy.org/tools/randseq.html.

SEQ ID NO: 11 is the amino acid sequence of a neutral EBD domain, EBD(0), which is a random sequence containing disorder-promoting residues P, Q, S and G in about the following amino acid ratios: G:P:Q:S=1:2:1:2. The sequence was produced using the random sequence generator tool located at the Swiss-Prot website: http://au.expasy.org/tools/randseq.html.

SEQ ID NO: 12 is a polynucleotide sequence encoding the amino acid sequence of SEQ ID NO: 1. Sequence was produced using the reverse translation tool located at: www.vivo.colostate.edu/molkit/rtranslate/index.html.

SEQ ID NO: 13 is a polynucleotide sequence encoding the amino acid sequence of SEQ ID NO: 2. Sequence was produced using the reverse translation tool located at: www.vivo.colostate.edu/molkit/rtranslate/index.html.

SEQ ID NO: 14 is a polynucleotide sequence encoding the amino acid sequence of SEQ ID NO: 3. Sequence was produced using the reverse translation tool located at: www.vivo.colostate.edu/molkit/rtranslate/index.html.

SEQ ID NO: 15 is a polynucleotide sequence encoding the amino acid sequence of SEQ ID NO: 4. Sequence was produced using the reverse translation tool located at: www.vivo.colostate.edu/molkit/rtranslate/index.html.

SEQ ID NO: 16 is a polynucleotide sequence encoding the amino acid sequence of SEQ ID NO: 5. Sequence was produced using the reverse translation tool located at: www.vivo.colostate.edu/molkit/rtranslate/index.html.

SEQ ID NO: 17 is a polynucleotide sequence encoding the amino acid sequence of SEQ ID NO: 6. Sequence was produced using the reverse translation tool located at: www.vivo.colostate.edu/molkit/rtranslate/index.html.

SEQ ID NO: 18 is a polynucleotide sequence encoding the amino acid sequence of SEQ ID NO: 7. Sequence was produced using the reverse translation tool located at: www.vivo.colostate.edu/molkit/rtranslate/index.html.

SEQ ID NO: 19 is a polynucleotide sequence encoding the amino acid sequence of SEQ ID NO: 8. Sequence was produced using the reverse translation tool located at: www.vivo.colostate.edu/molkit/rtranslate/index.html.

SEQ ID NO: 20 is a polynucleotide sequence encoding the amino acid sequence of SEQ ID NO: 9. Sequence was produced using the reverse translation tool located at: www.vivo.colostate.edu/molkit/rtranslate/index.html.

SEQ ID NO: 21 is a polynucleotide sequence encoding the amino acid sequence of SEQ ID NO: 10. Sequence was produced using the reverse translation tool located at: www.vivo.colostate.edu/molkit/rtranslate/index.html.

SEQ ID NO: 22 is a polynucleotide sequence encoding the amino acid sequence of SEQ ID NO: 11. Sequence was produced using the reverse translation tool located at: www.vivo.colostate.edu/molkit/rtranslate/index.html.

SEQ ID NO: 23 is the amino acid sequence of a positively charged EBD domain, EBD(+), which is a random sequence containing disorder-promoting residues P, Q, S and K in about the following amino acid ratios: K:P:Q:S=1:2:1:2. The sequence was produced using the random sequence generator tool located at the Swiss-Prot website: http://au.expasy.org/tools/randseq.html.

SEQ ID NO: 24 is the amino acid sequence of a positively charged EBD domain of SEQ ID NO: 23.

SEQ ID NO: 25 is the amino acid sequence of a negatively charged EBD domain, EBD(-), which is a random sequence containing disorder-promoting residues P, Q, S and E in about the following amino acid ratios: E:P:Q:S=1:2:1:2. The sequence was produced using the random sequence generator tool located at the Swiss-Prot website: http://au.expasy.org/tools/randseq.html.

SEQ ID NO: 26 is the amino acid sequence of a negatively charged EBD domain of SEQ ID NO: 25.

SEQ ID NO: 27 is the amino acid sequence of a neutral EBD domain, EBD(0), which is a random sequence containing disorder-promoting residues P, Q, S and G in about the following amino acid ratios: G:P:Q:S=1:2:1:2. The sequence was produced using the random sequence generator tool located at the Swiss-Prot website: http://au.expasy.org/tools/randseq.html.

SEQ ID NO: 28 is the amino acid sequence of a neutral EBD domain of SEQ ID NO: 27.

SEQ ID NO: 29 is a polynucleotide sequence encoding the amino acid sequence of SEQ ID NO: 23. The sequence was produced using the reverse translation tool located at: www.vivo.colostate.edu/molkit/rtranslate/index.html.

SEQ ID NO: 30 is a polynucleotide sequence encoding the amino acid sequence of SEQ ID NO: 24. The sequence was produced using the reverse translation tool located at: www.vivo.colostate.edu/molkit/rtranslate/index.html.

SEQ ID NO: 31 is a polynucleotide sequence encoding the amino acid sequence of SEQ ID NO: 25. The sequence was produced using the reverse translation tool located at: www.vivo.colostate.edu/molkit/rtranslate/index.html.

SEQ ID NO: 32 is a polynucleotide sequence encoding the amino acid sequence of SEQ ID NO: 26. The sequence was produced using the reverse translation tool located at: www.vivo.colostate.edu/molkit/rtranslate/index.html.

SEQ ID NO: 33 is a polynucleotide sequence encoding the amino acid sequence of SEQ ID NO: 27. The sequence was produced using the reverse translation tool located at: www.vivo.colostate.edu/molkit/rtranslate/index.html.

SEQ ID NO: 34 is a polynucleotide sequence encoding the amino acid sequence of SEQ ID NO: 28. The sequence was produced using the reverse translation tool located at: www.vivo.colostate.edu/molkit/rtranslate/index.html.

SEQ ID NO: 35 is the polypeptide sequence of an artificial EBD designed to contain amino acids X:P:Q:S in the following ratio 1:2:1:2, where X is a variable position to generate positive, negative or neutral bristles, and corresponds to one of K, E, or G respectively.

SEQ ID NO: 36 is the polynucleotide sequence of the pAquoProt expression vector backbone. The pAquoProt vector was built by adding the F1 origin of replication, LacI gene, and customized expression/cloning region to an existing pUC19 plasmid.

SEQ ID NO: 37 is the polynucleotide sequence of the pAquoKin expression vector backbone. The pAquoProt vector was built by adding the F1 origin of replication, LacI gene, and customized expression/cloning region to an existing pUC19 plasmid.

SEQ ID NO: 38 is the amino acid sequence of a negatively charged EBD domain, which is a random sequence containing disorder-promoting residues P, Q, S and E in about the following amino acid ratios: E:P:Q:S=1:2:1:1. The sequence was produced using the random sequence generator tool located at the Swiss-Prot website: http://au.expasy.org/tools/randseq.html.

SEQ ID NO: 39 is the amino acid sequence of a negatively charged EBD domain, which is a random sequence containing disorder-promoting residues P, Q, S and E in about the following amino acid ratios: E:P:Q:S=1:4:1:1. The sequence was produced using the random sequence generator tool located at the Swiss-Prot website: http://au.expasy.org/tools/randseq.html.

SEQ ID NO: 40 is the amino acid sequence of a negatively charged EBD domain, which is a random sequence containing disorder-promoting residues P, Q, S and E in about the following amino acid ratios: E:P:Q:S=2:2:1:1. The sequence was produced using the random sequence generator tool located at the Swiss-Prot website: http://au.expasy.org/tools/randseq.html.

SEQ ID NO: 41 is the amino acid sequence of a negatively charged EBD domain, which is a random sequence containing disorder-promoting residues P, Q, G and E in about the following amino acid ratios: E:P:Q:G=1:4:1:1. The sequence was produced using the random sequence generator tool located at the Swiss-Prot website: http://au.expasy.org/tools/randseq.html.

SEQ ID NO: 42 is the amino acid sequence of a negatively charged EBD domain, which is a random sequence containing disorder-promoting residues P, Q, G and E in about the following amino acid ratios: E:P:Q:G=2:2:1:1. The sequence was produced using the random sequence generator tool located at the Swiss-Prot website: http://au.expasy.org/tools/randseq.html.

SEQ ID NO: 43 is the amino acid sequence of a negatively charged EBD domain, which is a random sequence containing disorder-promoting residues P, Q, G and E in about the following amino acid ratios: E:P:Q:G=3:2:1:1. The sequence was produced using the random sequence generator tool located at the Swiss-Prot website: http://au.expasy.org/tools/randseq.html.

SEQ ID NO: 44 is the amino acid sequence of a negatively charged EBD domain, which is a random sequence containing disorder-promoting residues P, Q, S, G, D and E in about the following amino acid ratios: D:E:P:Q:S:G=1:2:3:1:2:1. The sequence was produced using the random sequence generator tool located at the Swiss-Prot website: http://au.expasy.org/tools/randseq.html.

SEQ ID NO: 45 is the amino acid sequence of a negatively charged EBD domain, in which certain amino acids in SEQ ID NO: 44 were substituted with the hydrophobic amino acids I, L, M, F, and V. The hydrophobic amino acid substitutions comprise approximately 12% of the residues.

SEQ ID NO: 46 is a polynucleotide sequence encoding the amino acid sequence of SEQ ID NO: 38. The sequence was produced using the reverse translation tool located at: www.vivo.colostate.edu/molkit/rtranslate/index.html.

SEQ ID NO: 47 is a polynucleotide sequence encoding the amino acid sequence of SEQ ID NO: 39. The sequence was produced using the reverse translation tool located at: www.vivo.colostate.edu/molkit/rtranslate/index.html.

SEQ ID NO: 48 is a polynucleotide sequence encoding the amino acid sequence of SEQ ID NO: 40. The sequence was produced using the reverse translation tool located at: www.vivo.colostate.edu/molkit/rtranslate/index.html.

SEQ ID NO: 49 is a polynucleotide sequence encoding the amino acid sequence of SEQ ID NO: 41. The sequence was produced using the reverse translation tool located at: www.vivo.colostate.edu/molkit/rtranslate/index.html.

SEQ ID NO: 50 is a polynucleotide sequence encoding the amino acid sequence of SEQ ID NO: 42. The sequence was produced using the reverse translation tool located at: www.vivo.colostate.edu/molkit/rtranslate/index.html.

SEQ ID NO: 51 is a polynucleotide sequence encoding the amino acid sequence of SEQ ID NO: 43. The sequence was produced using the reverse translation tool located at: www.vivo.colostate.edu/molkit/rtranslate/index.html.

SEQ ID NO: 52 is a polynucleotide sequence encoding the amino acid sequence of SEQ ID NO: 44. The sequence was produced using the reverse translation tool located at: www.vivo.colostate.edu/molkit/rtranslate/index.html.

SEQ ID NO: 53 is a polynucleotide sequence encoding the amino acid sequence of SEQ ID NO: 45. The sequence was produced using the reverse translation tool located at: www.vivo.colostate.edu/molkit/rtranslate/index.html.

DETAILED DESCRIPTION OF THE INVENTION

Artificial EBD fusion polynucleotides, polypeptides and vectors are provided by the present invention which offers significant advantages in the context of recombinant polypeptide production, particularly where it is desired to achieve, for example, improved solubility, improved yield, improved folding and/or reduced aggregation of a recombinant polypeptide of interest.

Artificial EBDs take advantage of the unique features of different classes of amino acids that are found within regions of order and disorder. The amino acids compositions of disordered and ordered regions in proteins are significantly different. Based on the analysis of intrinsically disordered proteins and regions within proteins, amino acids can be grouped into 3 categories: 1) order-promoting, 2) disorder-promoting, and 3) neutral (Dunker et al., Intrinsically disordered protein. *J Mol Graph Model*, 2001. 19(1): p. 26-59).

The advantages of the present invention are made possible by proper selection of disorder-promoting residues, order-promoting residues and/or neutral residues, as well as their respective proportions, within an artificial EBD sequence, as described herein. Proteins which have proven difficult to produce by conventional recombinant methodologies can be successfully produced when employing the artificial EBD sequences of the present invention.

The term "disorder-promoting amino acid residue" means an amino acid residue that promotes the disorder of stable tertiary and/or secondary structure within a polypeptide in solution. Disorder-promoting residues include D, M, K, R, S, Q, P, E and G.

The term "order-promoting amino acid residue" means an amino acid residue that promotes stable tertiary and/or secondary structure within a polypeptide in solution. Order-promoting amino acid residues include C, W, Y, I, F, V, L, H, T and N.

Neutral amino acid residues include A. The class of neutral amino acids can also include H, T, N, G, and D, as these amino acids tend to influence the tertiary and/or secondary structures within a protein or polypeptide to a relatively lesser extent then the other amino acids residues in above-defined classes (FIG. 1).

The phrases "about the ratio" and "in about the following amino acid ratio" means a group of amino acids as described herein, wherein the range "about" is determined by the actual ratio of said group of amino acids, first normalized by the lowest integer value within said group and then rounded to the nearest integer value. The resulting ratio if identical to the claimed ratio is then said to be "about" the claimed ratio of the group of amino acids. For example, consider a 100 AA EBD sequence of a fusion polypeptide which has the actual amino acid ratio of X:P:Q:S of 30:26:14:32. The actual amino acid ratio is normalized to 14, the lowest integer value, to yield a ratio of 2.1:1.9:1:2.3, which rounded to the nearest integer value is the ratio 2:2:1:2. Thus, a 100 AA EBD domain with an actual ratio of 30:26:14:32 has about the following amino acid ratio X:P:Q:S=2:2:1:2.

As used herein, the terms "polypeptide" and "protein" are used interchangeably, unless specified to the contrary, and according to conventional meaning, i.e., as a sequence of amino acids. Polypeptides are not limited to a specific length, e.g., they may comprise a full length protein sequence or a fragment of a full length protein, and may include post-translational modifications of the polypeptide, for example, glycosylations, acetylations, phosphorylations and the like, as well as other modifications known in the art, both naturally occurring and non-naturally occurring. Polypeptides of the invention may be prepared using any of a variety of well known recombinant and/or synthetic techniques, illustrative examples of which are further discussed below.

The practice of the present invention will employ, unless indicated specifically to the contrary, conventional methods of molecular biology and recombinant DNA techniques within the skill of the art, many of which are described below for the purpose of illustration. Such techniques are explained fully in the literature. See, e.g., Sambrook, et al., *Molecular Cloning: A Laboratory Manual* (2nd Edition, 1989); Maniatis et al., *Molecular Cloning: A Laboratory Manual* (1982); *DNA Cloning: A Practical Approach*, vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); *A Practical Guide to Molecular Cloning* (B. Perbal, ed., 1984).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

Fusion polypeptides comprising an EBD sequence and a heterologous polypeptide exhibit improved solubility relative to the corresponding heterologous polypeptide in the absence of the EBD sequence. In one embodiment, for example, the fusion polypeptide has at least 5% increased solubility relative to the heterologous polypeptide sequence alone. In another related embodiment, the fusion polypeptide has at least 25% increased solubility relative to the heterologous polypeptide sequence. In yet another related embodiment, the fusion polypeptide has at least 50% increased solubility relative to the heterologous polypeptide sequence.

The extent of improved solubility provided by an EBD sequence described herein can be determined using any of a number of available approaches (see for example, Kapust, R. B. and D. S. Waugh, *Escherichia coli* maltose-binding protein is uncommonly effective at promoting the solubility of polypeptides to which it is fused. *Protein Sci*, 1999. 8:1668-74; Fox, J. D., et al., Maltodextrin-binding proteins from diverse bacteria and archaea are potent solubility enhancers. *FEBS Lett*, 2003. 537:53-7; Dyson M R, Shadbolt S P, Vincent K J, Perera R L, McCafferty J. Production of soluble mammalian proteins in *Escherichia coli*: identification of protein features that correlate with successful expression. *BMC Biotechnol*. 2004 Dec. 14; 4(1):32).

Cells from single, drug resistant colony of *E. coli* overproducing the fusion polypeptide are grown to saturation in LB broth (Miller J H. 1972. *Experiments in molecular genetics*. Cold Spring Harbor, New York: Cold Spring Harbor Press. p 433) supplemented with 100 mg/mL ampicillin and 30 mg/mL chloramphenicol at 37° C. The saturated cultures are diluted 50-fold in the same medium and grown in shake-flasks to mid-log phase ($A_{600}$~0.5-0.7), at which time IPTG is added to a final concentration of 1 mM. After 3 h, the cells are recovered by centrifugation. The cell pellets are resuspended in 0.1 culture volumes of lysis buffer (50 mM Tris-HCl (pH 8.0), 150 mM NaCl, 1 mM EDTA), and disrupted by sonication. A total protein sample is collected from the cell suspension after sonication, and a soluble protein sample is collected from the supernatant after the insoluble debris is pelleted by centrifugation (20,000×g). These samples are subjected to SDS-PAGE and proteins are visualized by staining with Coomassie Brilliant Blue. At least three independent experiments are typically performed to obtain numerical estimates of the solubility of each fusion protein in *E. coli*. Coomassie-stained gels will be scanned with a gel-scanning densitometer and the pixel densities of the bands corresponding to the fusion proteins are obtained directly by volumetric integration. In each lane, the collective density of all *E. coli* proteins that are larger than the largest fusion protein are also determined by volumetric integration and used to normalize the values in each lane relative to the others. The percent solubility of each fusion protein is calculated by dividing the amount of soluble fusion protein by the total amount of fusion protein in the cells, after first subtracting the normalized background values obtained from negative control lanes (cells containing no expression vector). Descriptive statistical data (e.g., the mean and standard deviation) is then generated using standard methods.

The presence of an EBD sequence in fusion polypeptides of the present invention can also serve to reduce the extent of aggregation of a heterologous polypeptide sequence. In one embodiment, for example, the fusion polypeptide exhibits at least 10% reduced aggregation relative to the heterologous polypeptide. In another embodiment, the fusion polypeptide has at least 25% reduced aggregation relative to the heterologous polypeptide.

The extent of reduced aggregation provided by the fusion polypeptides of the present invention can be determined using any of a number of available techniques (see for example, Kapust, R. B. and D. S. Waugh, *Escherichia coli* maltose-binding protein is uncommonly effective at promoting the solubility of polypeptides to which it is fused. *Protein Sci*, 1999. 8:1668-74; Fox, J. D., et al., Maltodextrin-binding proteins from diverse bacteria and archaea are potent solubility enhancers. *FEBS Lett*, 2003. 537:53-7).

Cells from single, drug resistant colony of *E. coli* overproducing the fusion polypeptide are grown to saturation in LB broth (Miller J H. 1972. *Experiments in molecular genetics*. Cold Spring Harbor, New York: Cold Spring Harbor Press. p 433) supplemented with 100 mg/mL ampicillin and 30 mg/mL chloramphenicol at 37° C. The saturated cultures are diluted 50-fold in the same medium and grown in shake-flasks to mid-log phase ($A_{600}$~0.5-0.7), at which time IPTG is added to a final concentration of 1 mM. After 3 h, the cells are recovered by centrifugation. The cell pellets are resuspended in 0.1 culture volumes of lysis buffer (50 mM Tris-HCl (pH 8.0), 150 mM NaCl, 1 mM EDTA), and disrupted by sonication. A total protein sample is collected from the cell suspension after sonication, and an insoluble protein sample is collected from the pellet after the centrifugation (20,000×g). These samples are subjected to SDS-PAGE and proteins are visualized by staining with Coomassie Brilliant Blue. At least three independent experiments are typically performed to obtain numerical estimates of the solubility of each fusion protein in *E. coli*. Coomassie-stained gels are scanned with a gel-scanning densitometer and the pixel densities of the bands corresponding to the fusion proteins are obtained directly by volumetric integration. In each lane, the collective density of all insoluble *E. coli* proteins that are larger than the largest fusion protein is also determined by volumetric integration and used to normalize the values in each lane relative to the others. The percent insolubility of each fusion protein is calculated by dividing the amount of insoluble fusion protein by the total amount of fusion protein in the cells, after first subtracting the normalized background values obtained from negative control lanes (cells containing no expression vector). Descriptive statistical data (e.g., the mean and standard deviation) is generated by standard methods.

The presence of an EBD sequence in the fusion polypeptides of the present invention can also serve to improve the folding characteristics of the fusion polypeptides relative to the corresponding heterologous polypeptide, e.g., by minimizing interference caused by interaction with other proteins.

Assays for evaluating the folding characteristics of a fusion polypeptide of the invention can be carried out using conventional techniques, such as circular dichroism spectroscopy in far ultra-violet region, circular dichroism in near ultra-violet region, nuclear magnetic resonance spectroscopy, infra-red spectroscopy, Raman spectroscopy, intrinsic fluorescence spectroscopy, extrinsic fluorescence spectroscopy, fluorescence resonance energy transfer, fluorescence anisotropy and polarization, steady-state fluorescence, time-domain fluorescence, numerous hydrodynamic techniques including gel-filtration, viscometry, small-angle X-ray scattering, small angle neutron scattering, dynamic light scattering, static light scattering, scanning microcalorimetry, and limited proteolysis.

In another embodiment of the invention, an EBD comprises an amino acid sequence that maintains a substantially random coil conformation. Whether a given amino acid sequence maintains a substantially random coil conformation can be determined by circular dichroism spectroscopy in far ultra-violet region, nuclear magnetic resonance spectroscopy, infra-red spectroscopy, Raman spectroscopy, fluorescence spectroscopy, numerous hydrodynamic techniques including gel-filtration, viscometry, small-angle X-ray scattering, small angle neutron scattering, dynamic light scattering, static light scattering, scanning microcalorimetry, and limited proteolysis.

In another embodiment of the invention, an EBD sequence comprises an amino acid sequence that is substantially mutually repulsive. This property of being mutually repulsive can be determined by simple calculations of charge distribution within the polypeptide sequence.

In yet another embodiment of the invention, an EBD sequence comprises an amino acid sequence that remains in substantially constant motion, particularly in an aqueous environment. The property of being in substantially constant motion can be determined by nuclear magnetic resonance spectroscopy, small-angle X-ray scattering, small angle neutron scattering, dynamic light scattering, intrinsic fluorescence spectroscopy, extrinsic fluorescence spectroscopy, fluorescence resonance energy transfer, fluorescence anisotropy and polarization, steady-state fluorescence, time-domain fluorescence.

In another embodiment, the fusion polypeptides of the invention further comprise independent cleavable linkers, which allow an EBD sequence, for example at either the N or C terminus, to be easily cleaved from a heterologous polypeptide sequence of interest. Such cleavable linkers are known and available in the art. This embodiment thus provides improved isolation and purification of a heterologous polypeptide sequence and facilitates downstream high-throughput processes.

The present invention also provides polypeptide fragments of an EBD polypeptide sequence described herein, wherein the fragment comprises at least about 5, 10, 15, 20, 25, 50, or 100 contiguous amino acids, or more, including all intermediate lengths, of an EBD polypeptide sequence set forth herein, or those encoded by a polynucleotide sequence set forth herein. In a preferred embodiment, an EBD fragment provides similar or improved activity relative to the activity of the EBD sequence from which it is derived (wherein the activity includes, for example, one or more of improved solubility, improved folding, reduced aggregation and/or improved yield, when in fusion with a heterologous polypeptide sequence of interest.

In another aspect, the present invention provides variants of an EBD polypeptide sequence described herein. EBD polypeptide variants will typically exhibit at least about 70%, 75%, 80%, 85%, 90%, 91%, 92%, 93%, 94%, 95%, 96%, 97%, 98%, or 99% or more identity (e.g., determined as described below), along its length, to an EBD polypeptide sequence set forth herein. Preferably the EBD variant provides similar or improved activity relative to the activity of the EBD sequence from which the variant was derived (wherein the activity includes one or more of improved solubility, improved folding, reduced aggregation and/or improved yield, when in fusion with a heterologous polypeptide sequence of interest.

An EBD polypeptide variant thus refers to a polypeptide that differs from an EBD polypeptide sequence disclosed herein in one or more substitutions, deletions, additions and/or insertions. Such variants may be naturally occurring or may be synthetically generated, for example, by modifying one or more of the EBD polypeptide sequences of the invention and evaluating their activity as described herein and/or using any of a number of techniques well known in the art.

In certain instances, a variant will contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. As described above, modifications may be made in the structure of the EBD polynucleotides and polypeptides of the present invention and still obtain a functional molecule that encodes a variant or derivative polypeptide with desirable activity. When it is desired to alter the amino acid sequence of an EBD polypeptide to create an equivalent or an improved EBD variant or EBD fragment, one skilled in the art can readily change one or more of the codons of the encoding DNA sequence, for example according to Table 1.

For example, certain amino acids may be substituted for other amino acids in a protein structure without appreciable loss of desired activity. It is thus contemplated that various changes may be made in the EBD polypeptide sequences of the invention, or corresponding DNA sequences which encode said EBD polypeptide sequences, without appreciable loss of their desired activity.

TABLE 1

| Amino Acids | | | Codons | | | | |
|---|---|---|---|---|---|---|---|
| Alanine | Ala | A | GCA | GCC | GCG | | GCU |
| Cysteine | Cys | C | UGC | | | | UGU |
| Aspartic acid | Asp | D | GAC | | | | GAU |
| Glutamic acid | Glu | E | GAA | | | | GAG |
| Phenylalanine | Phe | F | UUC | | | | UUU |
| Glycine | Gly | G | GGA | GGC | GGG | | GGU |
| Histidine | His | H | CAC | | | | CAU |
| Isoleucine | Ile | I | AUA | AUC | | | AUU |
| Lysine | Lys | K | AAA | | | | AAG |
| Leucine | Leu | L | UUA | UUG | CUA | CUC | CUG | CUU |
| Methionine | Met | M | | AUG | | | |
| Asparagine | Asn | N | AAC | | | | AAU |
| Proline | Pro | P | CCA | CCC | CCG | | CCU |
| Glutamine | Gln | Q | CAA | | | | CAG |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | | ACU |
| Valine | Val | V | GUA | GUC | GUG | | GUU |
| Tryptophan | Trp | W | | UGG | | | |
| Tyrosine | Tyr | Y | UAC | | | | UAU |

In making such changes, the hydropathic index of amino acids may also be considered. The importance of the hydropathic amino acid index in conferring interactive biologic function on a protein is generally understood in the art (Kyte and Doolittle, 1982, incorporated herein by reference). It is accepted that the relative hydropathic character of the amino acid contributes to the secondary structure of the resultant protein, which in turn has potential bearing on the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

Therefore, according to certain embodiments, amino acids within an EBD sequence of the invention may be substituted by other amino acids having a similar hydropathic index or score. Preferably, any such changes result in an EBD sequence with a similar level of activity as the unmodified EBD sequence. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Thus, an amino acid can be substituted for another having a similar hydrophilicity value and in many cases still retain a desired level of activity. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like.

Amino acid substitutions within an EBD sequence of the invention may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes.

In an illustrative embodiment, a variant EBD polypeptide differs from the corresponding unmodified EBD sequence by substitution, deletion or addition of five percent of the original amino acids or fewer. Variants may also (or alternatively) be modified by, for example, the deletion or addition of amino acids that have minimal influence on the desired activity.

A polypeptide of the invention may further comprise a signal (or leader) sequence at the N-terminal end of the polypeptide, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support.

As noted above, the present invention provides EBD polypeptide variant sequences which share some degree of sequence identity with an EBD polypeptide specifically described herein, such as those having at least 40%, 50%, 60%, 70%, 80%, 90% or 95% identity with an EBD polypeptide sequence described herein. When comparing polypeptide sequences to evaluate their extent of shared sequence identity, two sequences are said to be "identical" if the sequence of amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O., (1978) *A model of evolutionary change in proteins—Matrices for detecting distant relationships*. In Dayhoff, M. O. (ed.) *Atlas of Protein Sequence and Structure*, National Biomedical Research Foundation, Washington DC Vol. 5, Suppl. 3, pp. 345-358; Hein J. (1990) Unified Approach to Alignment and Phylogenes, pp. 626-645 *Methods in Enzymology* vol. 183, Academic Press, Inc., San Diego, Calif.; Higgins, D. G. and Sharp, P. M., *CABIOS* 5:151-153 (1989); Myers, E. W. and Muller W., *CABIOS* 4:11-17 (1988); Robinson, E. D., *Comb. Theor* 11:105 (1971); Saitou, N. Nei, M., *Mol. Biol. Evol.* 4:406-425 (1987); Sneath, P. H. A. and Sokal, R. R., *Numerical Taxonomy—the Principles and Practice of Numerical Taxonomy*, Freeman Press, San Francisco, Calif. (1973); Wilbur, W. J. and Lipman, D. J., *Proc. Natl. Acad., Sci. USA* 80:726-730 (1983).

Alternatively, optimal alignment of sequences for comparison may be conducted by the local identity algorithm of Smith and Waterman, *Add. APL. Math* 2:482 (1981), by the identity alignment algorithm of Needleman and Wunsch, *J. Mol. Biol.* 48:443 (1970), by the search for similarity methods of Pearson and Lipman, *Proc. Natl. Acad. Sci. USA* 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al., *Nucl. Acids Res.* 25:3389-3402 (1977), and Altschul et al., *J. Mol. Biol.* 215:403-410 (1990), respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one preferred approach, the "percentage of sequence identity" is determined by comparing two optimally aligned sequences over a window of comparison of at least 20 positions, wherein the portion of the polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the reference sequence (i.e., the window size) and multiplying the results by 100 to yield the percentage of sequence identity.

In another aspect of the invention, there is provided an isolated polynucleotide sequence encoding a fusion polypeptide, the fusion polypeptide comprising at least one EBD sequence and at least one heterologous polypeptide sequence of interest. In a related aspect, the invention provides expression vectors comprising a polynucleotide encoding an EBD fusion polypeptide of the invention. In another related aspect, an expression vector of the invention comprises a polynucleotide encoding one or more EBD sequence and further comprises a multiple cloning site for the insertion of a polynucleotide encoding a heterologous polypeptide sequence of interest.

Polynucleotides compositions of the present invention may be identified, prepared and/or manipulated using any of a variety of well established techniques (see generally, Sambrook et al., *Molecular Cloning: A Laboratory Manual*, Cold Spring Harbor Laboratories, Cold Spring Harbor, N.Y., 1989, and other like references).

In addition, any polynucleotide of the invention, such as a polynucleotide encoding an EBD polypeptide sequence, or a vector comprising a polynucleotide encoding an EBD polypeptide sequence, may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl-methyl-, thio- and other modified forms of adenine, cytidine, guanine, thymine and uridine.

The terms "DNA" and "polynucleotide" are used essentially interchangeably herein to refer to a DNA molecule that has been isolated free of total genomic DNA of a particular species. "Isolated", as used herein, means that a polynucleotide is substantially away from other coding sequences, and that the DNA molecule does not contain large portions of unrelated coding DNA, such as large chromosomal fragments or other functional genes or polypeptide coding regions. Of course, this refers to the DNA molecule as originally isolated, and does not exclude genes or coding regions later added to the segment by the hand of man.

As will be understood by those skilled in the art, the polynucleotide compositions of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

As will also be recognized, polynucleotides of the invention may be single-stranded (coding or antisense) or double-stranded, and may be DNA (genomic, cDNA or synthetic) or RNA molecules. RNA molecules may include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

In addition to the EBD polynucleotide sequences set forth herein, the present invention also provides EBD polynucleotide variants having substantial identity to an EBD polynucleotide sequence disclosed herein, for example those comprising at least 50% sequence identity, preferably at least 55%, 60%, 65%, 70%, 75%, 80%, 85%, 90%, 95%, 96%, 97%, 98%, or 99% or higher, sequence identity compared to an EBD polynucleotide sequence of this invention using the methods described herein, (e.g., BLAST analysis using standard parameters, as described below). One skilled in this art will recognize that these values can be appropriately adjusted to determine corresponding identity of polypeptides encoded by two polynucleotide sequences by taking into account codon degeneracy, amino acid similarity, reading frame positioning and the like.

Typically, EBD polynucleotide variants will contain one or more substitutions, additions, deletions and/or insertions, preferably such that the activity (e.g., improved folding, reduced aggregation and/or improved yield, when in fusion with a heterologous sequence of interest) of the polypeptide encoded by the variant polynucleotide is not substantially diminished relative to the corresponding unmodified polynucleotide sequence.

In additional embodiments, the present invention provides polynucleotide fragments comprising or consisting of various lengths of contiguous stretches of sequence identical to or complementary to one or more of the EBD polynucleotide sequences disclosed herein. For example, polynucleotides are provided by this invention that comprise or consist of at least about 15, 20, 30, 40, 50, 75, 100, 150, 200, 300, 400, 500 or 1000 or more contiguous nucleotides of one or more of the sequences disclosed herein as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000, and the like. A polynucleotide sequence as described here may be extended at one or both ends by additional nucleotides not found in the native sequence. This additional sequence may consist of 1, 2, 3, 4, 5, 6, 7, 8, 9, 10, 11, 12, 13, 14, 15, 16, 17, 18, 19, or 20 nucleotides at either end of the disclosed sequence or at both ends of the disclosed sequence. Preferably, an EBD polynucleotide fragment of the invention encodes a fusion polypeptide that retains one or more desired activities, e.g., improved folding, reduced aggregation and/or improved yield, when in fusion with a heterologous sequence of interest.

The EBD polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative polynucleotide segments with total lengths of about 10,000, about 5000, about 3000, about 2,000, about 1,000, about 500, about 200, about 100, about 50 base pairs in length, and the like, (including all intermediate lengths) are contemplated to be useful in many implementations of this invention.

It will be appreciated by those of ordinary skill in the art that, as a result of the degeneracy of the genetic code, there are many nucleotide sequences that will encode a polypeptide as described herein. Some of these polynucleotides bear minimal homology to the native polynucleotide sequence. Nonetheless, polynucleotides that vary due to differences in codon usage are specifically contemplated by the present invention. Further, different alleles of an EBD polynucleotide sequence provided herein are within the scope of the present invention.

Alleles are endogenous sequences that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

In another embodiment of the invention, a mutagenesis approach, such as site-specific mutagenesis, may be employed for the preparation of variants and/or derivatives of the EBD polynucleotides and polypeptides described herein. By this approach, for example, specific modifications in a polypeptide sequence can be made through mutagenesis of the underlying polynucleotides that encode them. These techniques provides a straightforward approach to prepare and test sequence variants, for example, incorporating one or more of the foregoing considerations, by introducing one or more nucleotide sequence changes into the polynucleotide.

Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

In certain embodiments, the present invention contemplates the mutagenesis of the disclosed polynucleotide sequences to alter one or more activities/properties of the encoded polypeptide. The techniques of site-specific mutagenesis are well-known in the art, and are widely used to create variants of both polypeptides and polynucleotides. For example, site-specific mutagenesis is often used to alter a specific portion of a DNA molecule. In such embodiments, a primer comprising typically about 14 to about 25 nucleotides or so in length may be employed, in about 5 to about 10 residues on both sides of the junction of the sequence being altered.

As will be appreciated by those of skill in the art, site-specific mutagenesis techniques have often employed a phage vector that exists in both a single stranded and double stranded form. Typical vectors useful in site-directed mutagenesis include vectors such as the M13 phage. These phage are readily commercially-available and their use is generally well-known to those skilled in the art. Double-stranded plasmids are also routinely employed in site directed mutagenesis that eliminates the step of transferring the gene of interest from a plasmid to a phage.

In general, site-directed mutagenesis in accordance herewith is performed by first obtaining a single-stranded vector or melting apart of two strands of a double-stranded vector that includes within its sequence a DNA sequence that encodes the desired peptide. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected peptide-encoding DNA segments using site-directed mutagenesis provides a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al., 1994; Segal, 1976; Prokop and Bajpai, 1991; Kuby, 1994; and Maniatis et al., 1982, each incorporated herein by reference, for that purpose.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

In another approach for the production of polypeptide variants of the present invention, recursive sequence recombination, as described in U.S. Pat. No. 5,837,458, may be employed. In this approach, iterative cycles of recombination and screening or selection are performed to "evolve" individual polynucleotide variants of the invention wherein one or more desired activities is improved or modified.

In other embodiments of the present invention, the polynucleotide sequences provided herein can be advantageously used as probes or primers for nucleic acid hybridization. As such, it is contemplated that nucleic acid segments that comprise or consist of a sequence region of at least about a 15 nucleotide long contiguous sequence that has the same sequence as, or is complementary to, a 15 nucleotide long contiguous sequence disclosed herein may be used. Longer contiguous identical or complementary sequences, e.g., those of about 20, 30, 40, 50, 100, 200, 500, 1000 (including all intermediate lengths) and even up to full length sequences will also be of use in certain embodiments.

Many template dependent processes are available to amplify a target sequence of interest present in a sample. One of the best known amplification methods is the polymerase chain reaction (PCR™) which is described in detail in U.S. Pat. Nos. 4,683,195, 4,683,202 and 4,800,159, each of which is incorporated herein by reference in its entirety. Briefly, in PCR™, two primer sequences are prepared which are complementary to regions on opposite complementary strands of the target sequence. An excess of deoxynucleoside triphosphates is added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction product and the process is repeated. Preferably reverse transcription and PCR™ amplification procedure may be performed in order to quantify the amount of mRNA amplified. Polymerase chain reaction methodologies are well known in the art.

Any of a number of other template dependent processes, many of which are variations of the PCR™ amplification technique, are readily known and available in the art. Illustratively, some such methods include the ligase chain reaction (referred to as LCR), described, for example, in Eur. Pat. Appl. Publ. No. 320,308 and U.S. Pat. No. 4,883,750; Qbeta Replicase, described in PCT Intl. Pat. Appl. Publ. No. PCT/US87/00880; Strand Displacement Amplification (SDA) and Repair Chain Reaction (RCR). Still other amplification methods are described in Great Britain Pat. Appl. No. 2 202 328, and in PCT Intl. Pat. Appl. Publ. No. PCT/US89/01025. Other nucleic acid amplification procedures include transcription-based amplification systems (TAS) (PCT Intl. Pat. Appl. Publ. No. WO 88/10315), including nucleic acid sequence based amplification (NASBA) and 3SR. Eur. Pat. Appl. Publ. No. 329,822 describes a nucleic acid amplification process involving cyclically synthesizing single-stranded RNA ("ssRNA"), ssDNA, and double-stranded DNA (dsDNA). PCT Intl. Pat. Appl. Publ. No. WO 89/06700 describes a nucleic acid sequence amplification scheme based on the hybridization of a promoter/primer sequence to a target single-stranded DNA ("ssDNA") followed by transcription of many RNA copies of the sequence. Other amplification methods such as "RACE" (Frohman, 1990), and "one-sided PCR" (Ohara, 1989) are also well-known to those of skill in the art.

As noted, the EBD fusion polynucleotides, polypeptides and vectors of the present invention are advantageous in the context of recombinant polypeptide production, particularly where it is desired to achieve, for example, improved solubility, improved yield, improved folding and/or reduced aggregation of a heterologous polypeptide to which an EBD polypeptide sequence has been operably fused. Therefore, another aspect of the invention provides methods for producing a recombinant protein, for example by introducing into a host cell an expression vector comprising a polynucleotide sequence encoding a fusion polypeptide as described herein, e.g., a fusion polypeptide comprising at least one EBD sequence and at least one heterologous polypeptide sequence of interest; and expressing the fusion polypeptide in the host cell. In a related embodiment, the method further comprises the step of isolating the fusion polypeptide from the host cell. In another embodiment, the method further comprises the step of removing an EBD sequence from the fusion polypeptide before or after isolating the fusion polypeptide from the host cell.

For recombinant production of a fusion polypeptide of the invention, DNA sequences encoding the polypeptide components of a fusion polypeptide (e.g., one or more EBD sequences and a heterologous polypeptide sequence of interest) may be assembled using conventional methodologies. In one example, the components may be assembled separately and ligated into an appropriate expression vector. For example, the 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion polypeptide that retains the activities of both component polypeptides.

A peptide linker sequence may be employed to separate an EBD polypeptide sequence from a heterologous polypeptide sequence by some defined distance, for example a distance sufficient to ensure that the advantages of the invention are achieved, e.g., advantages such as improved folding, reduced aggregation and/or improved yield. Such a peptide linker sequence may be incorporated into the fusion polypeptide using standard techniques well known in the art. Suitable peptide linker sequences may be chosen based, for example, on the factors such as: (1) their ability to adopt a flexible extended conformation; and (2) their inability to adopt a secondary structure that could interfere with the activity of the EBD sequence. Illustrative peptide linker sequences, for example, may contain Gly, Asn and Ser residues. Other near neutral amino acids, such as Thr and Ala may also be used in the linker sequence. Amino acid sequences which may be usefully employed as linkers include those disclosed in Maratea et al., Gene 40:39-46, 1985; Murphy et al., Proc. Natl. Acad. Sci. USA 83:8258-8262, 1986; U.S. Pat. No. 4,935,233 and U.S. Pat. No. 4,751,180. The linker sequence may generally be from 1 to about 50 amino acids in length, for example.

The ligated DNA sequences of a fusion polynucleotide are operably linked to suitable transcriptional and/or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

The EBD and heterologous polynucleotide sequences may comprise a sequence as described herein, or may comprise a sequence that has been modified to facilitate recombinant polypeptide production. As will be understood by those of skill in the art, it may be advantageous in some instances to produce polypeptide-encoding polynucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences of the present invention can be engineered using methods generally known in the art in order to alter polypeptide encoding sequences for a variety of reasons, including but not limited to, alterations which modify the cloning, processing, and/or expression of the gene product. For example, DNA shuffling by random fragmentation and PCR reassembly of gene fragments and synthetic oligonucleotides may be used to engineer the nucleotide sequences. In addition, site-directed mutagenesis may be used to insert new restriction sites, alter glycosylation patterns, change codon preference, produce splice variants, or introduce mutations, and so forth.

In a particular embodiment, a fusion polynucleotide is engineered to further comprise a cleavage site located between the EBD polypeptide-encoding sequence and the heterologous polypeptide sequence, so that the hetereolous polypeptide may be cleaved and purified away from an EBD polypeptide sequence at any desired stage following expression of the fusion polypeptide. Illustratively, a fusion polynucleotide of the invention may be designed to include heparin, thrombin, or factor Xa protease cleavage sites.

In order to express a desired polypeptide, the nucleotide sequences encoding the polypeptide, or functional equivalents, may be inserted into appropriate expression vector, i.e., a vector which contains the necessary elements for the transcription and translation of an inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described, for example, in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York. N.Y.

A variety of expression vector/host systems may be utilized to contain and express polynucleotide sequences of the present invention. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the pBLUESCRIPT phagemid (Stratagene, La Jolla, Calif.) or pSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, any of a number of expression vectors may be selected depending upon the use intended for the expressed polypeptide. For example, when large quantities are needed, for example for the induction of antibodies, vectors which direct high level expression of fusion proteins that are readily purified may be used. Such vectors include, but are not limited to, the multifunctional *E. coli* cloning and expression vectors such as pBLUESCRIPT (Stratagene), in which the sequence encoding the polypeptide of interest may be ligated into the vector in frame with sequences for the amino-terminal Met and the subsequent 7 residues of β-galactosidase so that a hybrid protein is produced; pIN vectors (Van Heeke, G. and S. M. Schuster (1989) *J. Biol. Chem.* 264: 5503-5509); and the like. Proteins made in such systems may be designed to include heparin, thrombin, or factor Xa protease cleavage sites so that the cloned polypeptide of interest can be released from the EBD moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) *Methods Enzymol.* 153:516-544.

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, N. (1987) *EMBO J.* 6:307-311. Alternatively, plant promoters such as the small subunit of RUBISCO or heat shock promoters may be used (Coruzzi, G. et al. (1984) *EMBO J.* 3:1.671-1680; Broglie, R. et al. (1984) *Science* 224:838-843; and Winter, J. et al. (1991) *Results Probl. Cell Differ.* 17:85-105). These constructs can be introduced into plant cells by direct DNA transformation or pathogen-mediated transfection. Such techniques are described in a number of generally available reviews (see, for example, Hobbs, S. or Murry, L. E. in McGraw Hill Yearbook of Science and Technology (1992) McGraw Hill, New York, N.Y.; pp. 191-196).

An insect system may also be used to express a polypeptide of interest. For example, in one such system, *Autographa californica* nuclear polyhedrosis virus (AcNPV) is used as a vector to express foreign genes in *Spodoptera frugiperda* cells or in *Trichoplusia* larvae. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or *Trichoplusia* larvae in which the polypeptide of interest may be expressed (Engelhard, E. K. et al. (1994) *Proc. Natl. Acad. Sci.* 91:3224-3227).

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan, J. and Shenk, T. (1984) *Proc. Natl. Acad. Sci.* 81:3655-3659). In addition, transcription enhancers, such as the Rous sarcoma virus (RSV) enhancer, may be used to increase expression in mammalian host cells.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) *Results Probl. Cell Differ.* 20:125-162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, COS, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) *Cell* 11:223-32) and adenine phosphoribosyltransferase (Lowy, I. et al. (1990) *Cell* 22:817-23) genes which can be employed in tk.sup.- or aprt.sup.-cells, respectively. Also, antimetabolite, antibiotic or herbicide resistance can be used as the basis for selection; for example, dhfr which confers resistance to methotrexate (Wigler, M. et al. (1980) *Proc. Natl. Acad. Sci.* 77:3567-70); npt, which confers resistance to the aminoglycosides, neomycin and G-418 (Colbere-Garapin, F. et al (1981) *J. Mol. Biol.* 150:1-14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) *Proc. Natl. Acad. Sci.* 85:8047-51). The use of visible markers has gained popularity with such markers as anthocyanins, β-glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) *Methods Mol. Biol.* 55:121-131).

Although the presence/absence of marker gene expression suggests that the gene of interest is also present, its presence and expression may need to be confirmed. For example, if the sequence encoding a polypeptide is inserted within a marker gene sequence, recombinant cells containing sequences can be identified by the absence of marker gene function. Alternatively, a marker gene can be placed in tandem with a polypeptide-encoding sequence under the control of a single promoter. Expression of the marker gene in response to induction or selection usually indicates expression of the tandem gene as well.

Alternatively, host cells that contain and express a desired polynucleotide sequence may be identified by a variety of procedures known to those of skill in the art. These procedures include, but are not limited to, DNA-DNA or DNA-RNA hybridizations and protein bioassay or immunoassay techniques which include, for example, membrane, solution, or chip based technologies for the detection and/or quantification of nucleic acid or protein.

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide may be preferred for some applications, but a competitive binding assay may also be employed. These and other assays are described, among other places, in Hampton, R. et al. (1990; Serological Methods, a Laboratory Manual, APS Press, St Paul. Minn.) and Maddox, D. E. et al. (1983; *J. Exp. Med.* 158:1211-1216).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the polypeptide from cell culture. The polypeptide produced by a recombinant cell may be secreted or contained intracellularly depending on the sequence and/or the vector used. As will be understood by those of skill in the art, expression vectors containing polynucleotides of the invention may be designed to contain signal sequences which direct secretion of the encoded polypeptide through a prokaryotic or eukaryotic cell membrane. Other recombinant constructions may be used to join sequences encoding a polypeptide of interest to polynucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor Xa or enterokinase (Invitrogen. San Diego, Calif.) between the purification domain and the encoded polypeptide may be used to facilitate purification. One such expression vector provides for expression of a fusion protein containing a polypeptide of interest and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, *Prot. Exp. Purif.* 3:263-281) while the enterokinase cleavage site provides a means for purifying the desired polypeptide from the fusion protein. Further discussion of vectors which comprise fusion proteins can be found in Kroll, D. J. et al. (1993; *DNA Cell Biol.* 12:441-453).

In addition to recombinant production methods, polypeptides of the invention, and fragments thereof, may be produced by direct peptide synthesis using solid-phase techniques (Merrifield J. (1963) *J. Am. Chem. Soc.* 85:2149-2154). Polypeptide synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the full length molecule.

According to another aspect, the present invention further provides binding agents, such as antibodies and antigen-binding fragments thereof, that specifically bind to an EBD sequence according to the present invention, or to a portion, variant or derivative thereof. Such binding agents may be used, for example, to detect the presence of a polypeptide comprising an EBD sequence, to facilitate purification of a polypeptide comprising an EBD sequence, and the like. An antibody, or antigen-binding fragment thereof, is said to "specifically bind" to a polypeptide if it reacts at a detectable level (within, for example, an ELISA assay) with the polypeptide, and does not react detectably with unrelated polypeptides under similar conditions.

Antibodies and other binding agents can be prepared using conventional methodologies. For example, monoclonal antibodies specific for a polypeptide of interest may be prepared using the technique of Kohler and Milstein, *Eur. J. Immunol.* 6:511-519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

A number of "humanized" antibody molecules comprising an antigen-binding site derived from a non-human immunoglobulin have been described, including chimeric antibodies having rodent V regions and their associated CDRs fused to human constant domains (Winter et al. (1991) *Nature* 349: 293-299; Lobuglio et al. (1989) *Proc. Nat. Acad. Sci. USA* 86:4220-4224; Shaw et al. (1987) *J Immunol.* 138:4534-4538; and Brown et al. (1987) *Cancer Res.* 47:3577-3583), rodent CDRs grafted into a human supporting FR prior to fusion with an appropriate human antibody constant domain (Riechmann et al. (1988) *Nature* 332:323-327; Verhoeyen et al. (1988) *Science* 239:1534-1536; and Jones et al. (1986) *Nature* 321:522-525), and rodent CDRs supported by recombinantly veneered rodent FRs (European Patent Publication No. 519,596, published Dec. 23, 1992). These "humanized" molecules are designed to minimize unwanted immunological response toward rodent antihuman antibody molecules which limits the duration and effectiveness of therapeutic applications of those moieties in human recipients.

Yet another aspect of the invention provides kits comprising one or more compositions described herein, e.g., an isolated EBD polynucleotide, polypeptide, antibody, vector, host cell, etc. In a particular embodiment, the invention provides a kit containing an expression vector comprising a polynucleotide sequence encoding an EBD polypeptide sequence and a multiple cloning site for easily introducing into the vector a polynucleotide sequence encoding a heterologous polypeptide sequence of interest. In another embodiment, the expression vector further comprises an engineered cleavage site to facilitate separation of the EBD polypeptide sequence from the heterologous polypeptide sequence of interest following recombinant production.

The following Examples are offered by way of illustration and not by way of limitation.

EXAMPLES

Example 1

Artificial EBDs Effectively Solubilize Insoluble Proteins

To address host cell toxicity problems associated with the use of certain naturally-occurring EBD sequences in fusion with heterologous proteins, artificial sequences were designed. Our knowledge of the intrinsic protein disorder phenomenon allowed us to design highly disordered artificial EBD sequences with desirable charge properties. Further, the likelihood that a completely artificial sequence would possess cytotoxicity due to the specific interaction with cellular components seemed to be minimal.

Designing the Artificial Entropic Bristles

In order to serve as an artificial EBD, a polypeptide chain should be highly flexible and disordered. Statistical comparisons of amino acid compositions indicated that disordered and ordered regions in proteins are different to a significant degree. Based on the analysis of intrinsically disordered (ID) proteins and disordered regions within proteins, amino acid residues were categorized as (1) order-promoting, (2) disorder-promoting and (3) neutral (Dunker, et al., *J Mol Graph Model*, 2001. 19(1): p. 26-59). FIG. 1 presents relative amino acid compositions of ID regions available in the DisProt database (Sickmeier et al. *Bioinformatics*, 2005. 21(1): p. 137-40). The amino acid compositions were compared using a profiling approach (Dunker, et al., *J Mol Graph Model*, 2001. 19(1): p. 26-59). FIG. 1 shows that certain order-promoting residues include C, W, Y, I, F, V, L, H, T, and N, disorder-promoting residues include D, M, K, R, S, Q, P, E, and G, while neutral residues include A. It is notable that H, T, N, G, and D are borderline by the 0.1 fractional difference criterion, and so these residues could also be considered neutral in certain contexts.

The right-most bars representing the most disorder-promoting residues (E, P, Q, S, and K) together with the disorder-neutral residue G were chosen as basis for the de novo design of artificial EBDs. An artificial EBD was designed to contain the chosen residues in about the following amino acid ratios: X:P:Q:S=1:2:1:2, where X is a variable position to generate positive, negative or neutral bristles, and corresponds to one of K, E, or G, respectively.

The 1:2:1:2 proportions for X:P:Q:S were based on the following observations. Proline disrupts secondary structure (except for polyproline II helix) and contains hydrophobic surfaces for weak binding to possible aggregation patches, so a high proportion of P was chosen. PolyQ spontaneously aggregates, so a low proportion of Q was chosen to avoid aggregation-prone continuous stretches of Q. The side chain of serine is hydrophilic, but its ability to hydrogen bond with the backbone leads to very high conformational variability, so a high proportion of S was chosen. Since structured regions of proteins never contain long regions of very low complexity (Romero et al., *Proteins*. 2001. 42(1): p. 38-48), a small number of different amino acids (e.g., a low complexity bristle) reduces the chance of accidental formation of stable tertiary structure by stable interactions with other parts of the protein.

Based on these prerequisites, a 100 residue long random sequence was generated. The resulting sequence is shown in FIG. 2. Then, a fragment of this sequence, underlined sequence in FIG. 2A, was chosen to serve as the de novo EBD. This general sequence was used to generate EBDs that were positive (EB+), negative (EB−) and neutral (EB0) (FIG. 2B).

Target Protein Selection

Thirteen proteins previously shown to be insoluble without fusions or shown to be insoluble even when fused to maltose-binding protein (MBP) were selected (Kapust et al., Protein Sci, 1999. 8(8): p. 1668-74; Kataeva et al., *J Proteome Res*, 2005. 4(6): p. 1942-51). Nine of these proteins were insoluble even at 30° C. of induction (Kataeva et al., *J Proteome Res*, 2005. 4(6): p. 1942-51). The proteins had molecular masses from 8.4 to 28.3 kDa; isoelectric points (pI) from 3.55 to 10.9, and net charges from +20 to −17. These proteins and some of their properties are listed in Table 2.

Cloning Methods

To attach EBDs to N-termini of target proteins, the Gateway Cloning Technique (Invitrogen) based on a specific recombination of homologous DNA sequences was used. For polymerase chain reaction (PCR) accuracy, the high fidelity and specificity AccuPrime Pfx DNA polymerase (Invitrogen) was used (Takagi et al., *Appl Environ Microbiol*, 1997. 63(11): p. 4504-10). Primers were designed and optimized using XPression Primer 3.0 software. PCR products were purified using Wizard SV Gel and PCR Clean-Up System (Promega) or by mini-dialysis using Millipore. To generate entry clones, pDONR221 (Invitrogen) was used as an entry vector. All entry clones have been verified by sequencing. For the creation of expression clones, pDEST-42 destination vector (Gateway) was used. A point point mutation in pDEST-42 was done using QuickChange II XL Site-Directed Mutagenesis Kit (Stratagene). One Shot TOP10 and BL21 Star (DE3) One Shot competent cells (Invitrogen) were commonly used for transformation with BP and LR reactions, respectively. Plasmid DNAs were purified using Wizard Plus SV Mini-preps DNA Purufication System (Promega). To create maltose-binding protein (MBP) fusions the target genes were amplified by PCR using forward and reverse primers flanked by attB1 and attB2 sites, respectively, and cloned into entry vector as described above. To create expression clones, pDEST-544 vector (Invitrogen) was used. Proteins expressed from this vector had an MBP at their N-termini.

Cell Growth and Lysis

Cultures were grown in an LB medium supplied with 100 μg/mL ampicillin at 37° C. overnight and used next morning to start new 1 ml cultures. The tubes were incubated with shaking at 37° C. for 4 hours. Then IPTG was added to a final concentration of 1 mM and the tubes were shaken for additional 4 h at either 37° C. or 30° C. The cells were collected by centrifugation and lysed chemically using the combination of mild nonionic detergent and a lysozyme (B-PER Reagent, Thermo). The suspensions were stirred for 30 min at room temperature. The lysed solution was designated as a "whole fraction". The "soluble fraction" was obtained by removal of insoluble fraction by centrifugation. The whole and the soluble fractions were used for the detection of protein expression and solubility, respectively.

Design of Cloning Strategy

Figure 3:
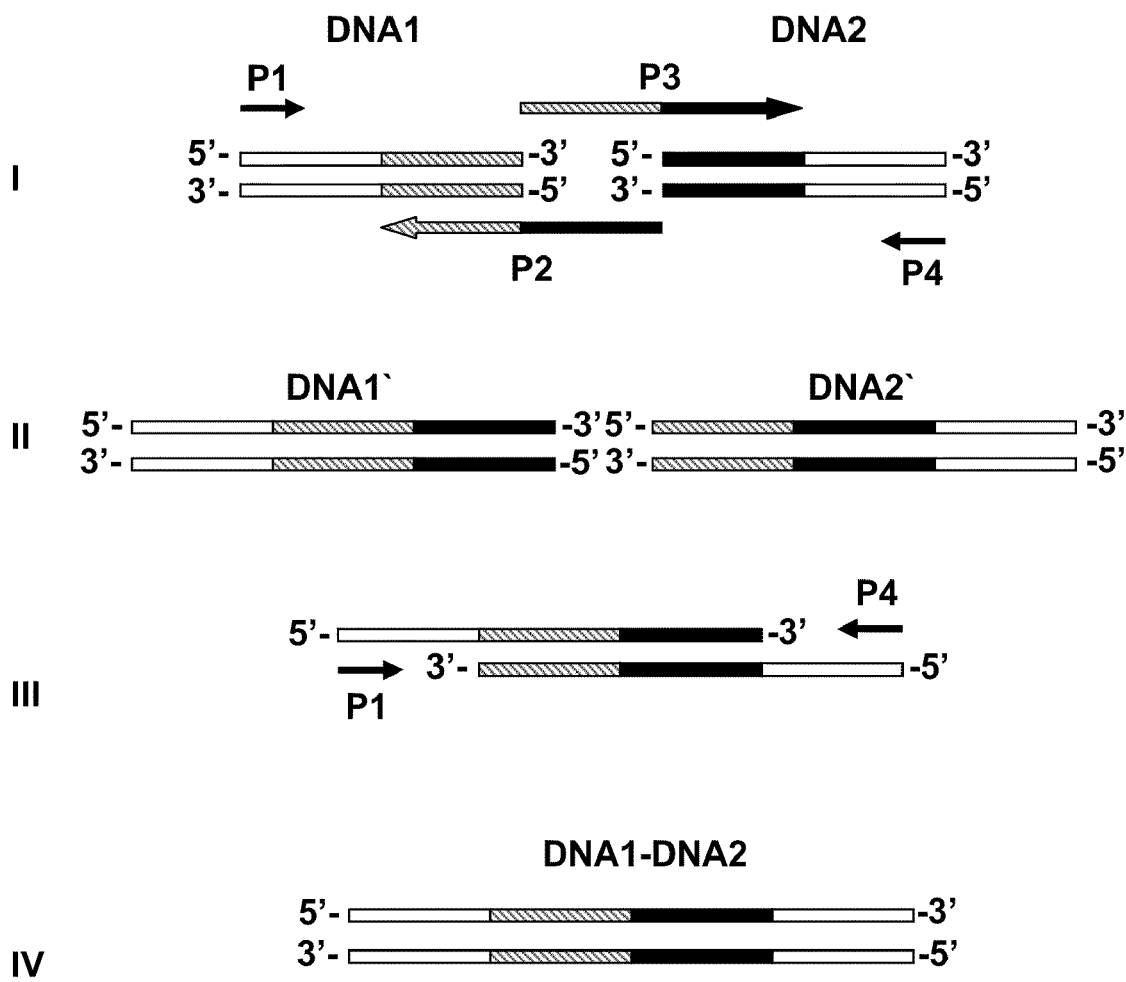
FIG. 3. Ligation of two DNA sequences via PCR. I, amplification of DNA1 and DNA2 sequences using reversed DNA1 overlapping primer P2 and DNA2 forward overlapping primer P3. II, Products of the PCR1 bearing overlapping fragments. III, PCR2 annealing step. IV. Final product composed of DNA1+DNA2.

To avoid translation of the eleven amino acid residues attB1 recombination site, (i.e. for native protein expression), its start codon (ATG) was mutated to ATA encoding isoleucine. For the same reason, Shine-Dalgarno (SD) sequence followed by a linker (L) and a start codon were inserted between the attB1 site and the entropic bristle sequence. Original reversed transcripts of 30 amino acid residues of the designed artificial EBDs were 90 bases long. After addition of a 5'-fragment (the attB1 site, the Shine Dalgarno, the linker, and the start codon), the resulted DNA fragment to be synthesized was over 140 bases long. To minimize mistakes upon synthesis of such a large DNA fragment, the putative DNA sequence of each EBD was divided into three pieces. Each piece was amplified and linked to the next one using set of PCRs and overlapping primers (see FIG. 3) (Kataeva et al., J Proteome Res, 2005. 4(6): p. 1942-51). After generating of EBD DNA fragments, target genes with a stop codons at their 3'-termini were amplified by PCR and linked to the 3'-terminus of each entropic bristle using the above principle (FIG. 3). Thus, each final PCR product had the following composition: attB1-SD-L-EBD-Target Gene-stop-attB2. The constructs were inserted into cloning vector. Plasmid DNAs of the clones were isolated and verified by sequencing. The "right" clones were used (1) as sources of DNA sequences encoding EBDs and (2) to make expression clones in LR reaction.

Expression and Solubility Test

To evaluate protein expression and solubility, the proteins of the whole and soluble fractions were separated by SDS-PAGE using NuPAGE 4-12% Bis-Tris Gels and the supplied reagents (Invitrogen). Gels were stained with Coomassie Blue Reagent.

Figure 4A:
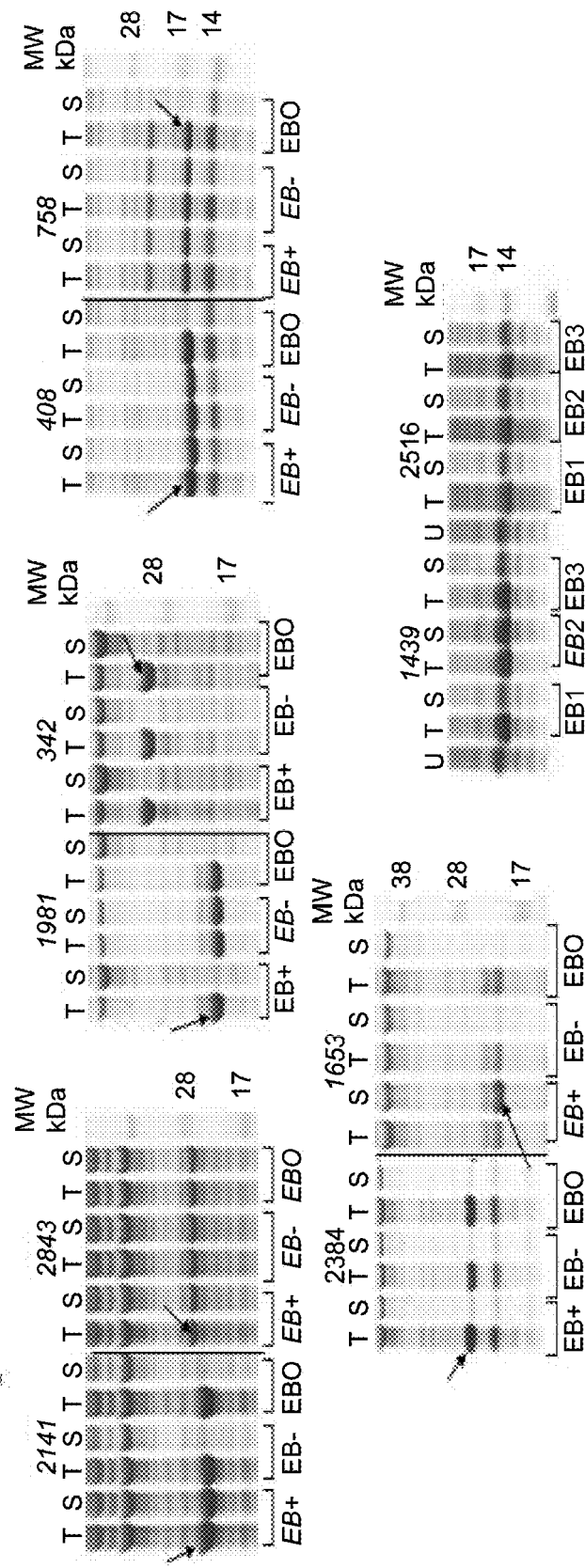
FIGS. 4A and 4B. Expression and solubility of ten *C. thermocellum* proteins with N-terminal entropic bristles induced at 37° C. (4A), or MBP-fusions induced at 37° C. and 30° C. (4B). Abbreviations: T, total protein, S, soluble protein, U, uninduced cells. IDs of solubilized proteins and the corresponding EBDs are shown initalics.
Figure 4B:
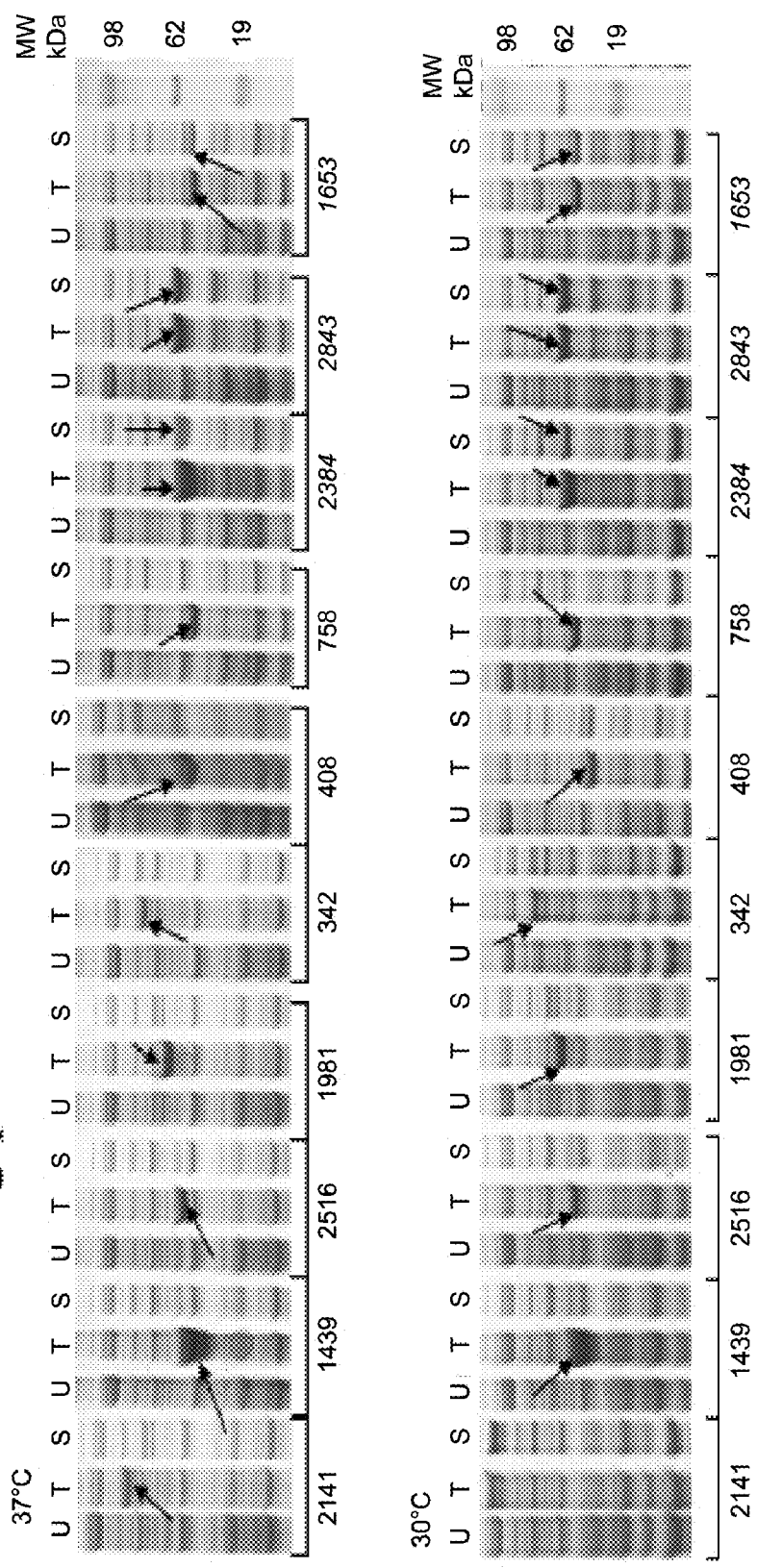

Results: Expression and Solubility of Fusion Proteins Comprising Artificial EBDs FIG. 4 and Table 2 show that artificial EBDs fused to the N-termini of target proteins was highly effective. Eleven out of thirteen insoluble proteins were solubilized by this approach (Highlighted portions of Table 2 represent the proteins that were solubilized by fusion to artificial EBDs or to MBP). The level of expression of all EBD-fusions was good. At 37° C. of induction, neutral EB0 solubilized 1 protein. Charged EB+ and EB− solubilized 5 and 6 proteins, respectively. Decreasing induction temperature improved soluble protein expression (Kataeva et al., J Proteome Res, 2005. 4(6): p. 1942-51). Induction at 30° C. did not change solubility of EBD0 fusions but resulted in 4 and 1 more soluble EBD+ and EBD− fusion proteins, respectively. FIG. 4 illustrates expression and solubility of 10 bacterial proteins fused either to artificial EBDs (FIG. 4A) or to maltose-binding protein (FIG. 4B), whereas Table 2 summarizes the results of the solubility studies.

TABLE 2

| Protein | MW (kDa) | pI | Charge | 37° C. EBD+ E | S | EBD− E | S | EBD₀ E | S | 30° C. EBD+ E | S | EBD− E | S | EBD₀ E | S | 37° C. MBP fusion E | S | 30° C. MBP fusion E | S |
|---|---|---|---|---|---|---|---|---|---|---|---|---|---|---|---|---|---|---|---|
| 342-Transposase_mut | 23.3 | 10.9 | 20 | 1 | 0 | 1 | 0 | 1 | 0 | 1 | 0 | 1 | 0 | 1 | 0 | 1 | 0 | 1 | 0 |
| 1981-IF-2B | 17.1 | 10 | 6.5 | 1 | 0 | 1 | 1 | 1 | 0 | 1 | 0 | 1 | 1 | 1 | 0 | 1 | 0 | 1 | 0 |
| 2516-DUF199 | 9.2 | 9.55 | 3 | 1 | 0 | 1 | 0 | 1 | 0 | 1 | 0 | 1 | 0 | 1 | 0 | 1 | 0 | 1 | 0 |
| 758-DUF111 | 12.5 | 7.3 | 5 | 1 | 1 | 1 | 1 | 1 | 0 | 1 | 1 | 1 | 1 | 1 | 0 | 1 | 0 | 1 | 0 |
| 2843-Cons_hypoth95 | 21.7 | 6.8 | 0.5 | 1 | 1 | 1 | 1 | 1 | 1 | 1 | 1 | 1 | 1 | 1 | 1 | 1 | 1 | 1 | 1 |
| 408-UbiA | 12.4 | 5.8 | -0.5 | 1 | 1 | 1 | 1 | 1 | 0 | 1 | 1 | 1 | 1 | 1 | 0 | 1 | 0 | 1 | 0 |
| 2384-HD | 21.1 | 5.5 | -1.5 | 1 | 0 | 1 | 0 | 1 | 0 | 1 | 1 | 1 | 1 | 1 | 0 | 1 | 1 | 1 | 1 |
| CATA9 | 26.7 | 5.2 | -14 | 1 | 0 | 1 | 1 | 0 | 0 | 1 | 1 | 1 | 0 | 0 | 0 | 1 | 0 | 1 | 0 |
| 2141-DNA_gyraseB_C | 23.2 | 5.2 | -3 | 1 | 1 | 1 | 0 | 1 | 0 | 1 | 1 | 1 | 0 | 1 | 0 | 0 | 0 | 0 | 0 |
| GFP | 28.3 | 5.13 | -14 | 1 | 0 | 1 | 0 | 1 | 0 | 1 | 1 | 1 | 1 | 0 | 0 | 1 | 1 | 1 | 1 |
| p16 | 17.7 | 4.94 | -5 | 1 | 0 | 1 | 0 | 1 | 0 | 1 | 1 | 1 | 0 | 0 | 0 | 1 | 0 | 1 | 0 |
| 1653-UPF0004 | 17.1 | 4.4 | -8.5 | 1 | 1 | 1 | 0 | 1 | 0 | 1 | 1 | 1 | 0 | 1 | 0 | 1 | 1 | 1 | 1 |
| 1439-AAA_div | 8.4 | 3.55 | -17 | 1 | 0 | 1 | 1 | 1 | 0 | 1 | 0 | 1 | 1 | 1 | 0 | 1 | 0 | 1 | 0 |

E = expression; S = solubilization; 1 = soluble; 0 = insoluble

In summary, fusion of MBP significantly increased the solubility of just 4 of 13 proteins, at 37° C. or at 30° C., whereas the artificial EBD of the present invention increased the solubility for 11 of the 13 previously insoluble proteins.

Example 2

Development of Novel EBD-Fusion Expression Vectors

A. Design of the AquoProt/AquoKin Vector Backbone

This example describes the cloning of the generic 4.2 kilobase pAquoProt and pAquoKin vector backbone. pUC19 is the source for the dsDNA polypeptide used to build the AquoProt and AquoKin vectors. Functional features already present in the pUC19 vector include the DNA sequence encoding ampicillin resistance and the *E. coli* high copy origin. Additional features in the hybrid plasmid include an f1 origin, allowing for in vitro translation system compatibility; a novel cloning/expression cassette allowing for expression of a unique synthetic polypeptide fusion to a target protein (described in detail below); and the Lacl gene enabling host-independent control of the promoter controlling protein translation within the *E coli*. Digestion of the pUC19 vector with the EcoO1091 restriction enzyme allowed ligation of the f1 origene fragment in an anti-sense orientation. Next, the pUC19 vector containing antisense f1-origin was digested with NdeI and PvuII restriction enzymes to allow for the directional insertion of the synthesized cloning/expression cassette described below. This step was completed prior to the insertion of the Lacl gene due to the presence of PvuII sites in the LacI gene coding sequence. The pUC19 vector containing antisense f1-origin and the cloning/expression cassette was digested using the SapI restriction site, and LacI was ligated in a sense orientation. The resultant product of these cloning steps is shown in FIG. 5, and is termed the pAquoProt vector backbone. In addition, the cloning/expression cassette can be partially replaced by digestion at SalI and NdeI sites followed by ligation of the AquoKin expression cassette to yield the pAquoKin vector backbone.

B. Design of the AquoProt Cloning/Expression Cassette.

This example describes the functional features designed into the 378 bp cloning/expression cassette that will result in the pAquoProt vector (FIG. 6). Preceding 5' to 3' from the ribosomal binding site (AAGAG, start by 100) several features were added to distinguish this cloning region from the original pUC19 vector. The DNA fragment for an N-terminal poly-histidine (His-tag) preceded by a start codon was inserted to aid purification and detection. Downstream of the His-tag a unique BstBI restriction site (start by 144) was added. Cleavage of the BstBI site was utilized for the in-frame insertion of the artificial fusion sequences described in claims 1-23). A DNA fragment encoding the recognition sequence for the endopeptidase, enterokinase, follows the BstBI and facilitates post-translational cleavage of the His-tag and fusion-peptide. This accommodates end-user needs to remove fusion polypeptides as applications dictate. Next the unique restriction sites BamHI, MfeI, EcoRV, KpnI, HindIII, EagI, NotI, XhoI are present to assist cloning of the desired protein encoding cDNA into the vector. Finally, a C-terminal HA-tag encoding sequence (start by 224) exists so that the hybrid polypeptide can be post-translationally detected via immunochemistry. Alternatively, a stop codon can be placed as the final codon of the user-inserted protein polypeptide to prevent the addition of the post-translational addition of the HA-tag.

C. Design of the AquoKin Expression/Cloning Cassette

This example describes the functional features designed into the 381 bp cloning/expression cassette that distinguish the pAquokin vector (FIG. 7) from the pAquoProt vector (FIG. 6). First, a second solubility-aiding polypeptide described within claims X-Z will be cloned into the Eco47III site (start bp247). This restriction site is downstream of the C-terminal affinity tag, and results in the translation of a hybrid user-inserted protein with N- and C-terminal solubility-aiding EBD fusions. The vector has been designed such that these fusions can be simultaneously removed by post-translational digestion with the endopeptidase, enterokinase. To facilitate the one-step cleavage of both fusions the C-terminal affinity tag was changed from an HA-tag to the FLAG™-tag recognition sequence (U.S. Pat. No. 4,703,004) which also encodes the enterokinase consensus site. The resultant post-translational cleavage product will be the user-inserted protein sequence with a c-terminal DYKDDDK sequence that allows detection of the hybrid-polypeptide via immunochemistry.

Example 3

Artificial EBDs Effectively Solubilize Insoluble Proteins

Example 1 demonstrated that the 30 amino acid negatively charged EBDs were more effective in some instances than the neutral and positive EBDs. Therefore, additional negatively charged artificial EBDs were designed to expand the range of synthetic fusion tags. These further EBDs contain amino acids in the following approximate ratios: E:P:Q:S=1:2:1:1, E:P:Q:S=1:4:1:1, E:P:Q:S=2:2:1:1; E:P:Q:G=1:4:1:1, E:P:Q:G=2:2:1:1, E:P:Q:G=3:2:1:1, D:E:P:Q:S:G=1:2:3:1:2:1, and the D:E:P:Q:S:G=1:2:3:1:2:1 EBD sequence was also modified to contain the hydrophobic patches comprised of amino acids I, L, M, F, and V such that the EBD had approximately 12% overall hydrophobic character. Based on these amino acid ratios, 120 to 250 residue long sequences were generated computationally. The resulting polypeptide sequences are represented as SEQ ID NOs: 38-45. The EBD amino acid sequences were reverse translated into polynucleotide open reading frames and synthesized de novo (SEQ ID NOs: 46-53). The polynucleotide sequences were utilized as templates to generate novel EBDs of differing lengths and amino acid compositions. Once PCR amplified, the novel EBD coding sequences were cloned into the BstBI site of the pAquoProt vector backbone such that target proteins expressed from these plasmids have an N-terminal fusion consisting of a His-tag-EBD-EK cleavage site. Likewise, novel EBD coding sequences were cloned in various combinations into the BstBI site and Eco47III site of the pAquoKin vector backbone such that a heterologous protein expressed from this plasmid has EBDs translationally fused to both termini. A large library of expression vectors was generated by combining various EBDs into generic expression vectors to further evaluate the physical properties that are advantageous for promoting the soluble expression of a fusion partner. Table 3 lists a subset of the EBDs that have been tested and their physical properties. These EBDs span a range of lengths (24 to 250 amino acids) and exhibit a variety of amino acid compositions. Regardless of the sequence diversity between individual EBDs, all of these EBDs are low complexity, unstructured, synthetic fusion tags with negative net charges.

TABLE 3

| Seq ID (A.A.#s) | Parent A.A. ratio | EBD length | MW | Net Charge | pI |
|---|---|---|---|---|---|
| SeqID 7 (96-120) | E:P:Q:G = 1:4:1:1 | 24 | 2.5 kDa | −6 | 3.63 |
| SeqID 5 (61-120) | E:P:Q:S = 2:2:1:1 | 60 | 6.8 kDa | −24 | 3.08 |
| SeqID 9 (1-60) | E:P:Q:G = 2:2:1:1 | 60 | 6.3 kDa | −18 | 3.09 |
| SeqID 11 (1-60) | E:P:Q:G = 3:2:1:1 | 60 | 6.7 kDa | −25 | 2.97 |

TABLE 3-continued

| Seq ID (A.A.#s) | Parent A.A. ratio | EBD length | MW | Net Charge | pI |
|---|---|---|---|---|---|
| SeqID 9 (47-120) | E:P:Q:G = 2:2:1:1 | 74 | 7.9 kDa | −23 | 3.10 |
| SeqID 11 (1-120) | E:P:Q:G = 3:2:1:1 | 120 | 13.1 kDa | −51 | 2.75 |
| SeqID 13 (1-144) | D:E:P:Q:S:G = 1:2:3:1:2:1 | 144 | 15 kDa | −41 | 2.69 |
| SeqID 15 (1-250) | SeqID 13 + I, L, M, F V | 250 | 26.1 kDa | −65 | 2.48 |
| SeqID 15 (1-81) | SeqID 13 + I, L, M, F V | 81 | 8.8 kDa | −27 | 2.87 |

EBD Performance Testing

Various insoluble target proteins were selected to test the solubility-enhancing performance of the EBDs. cDNA clones for the recalcitrant proteins were either purchased from commercial sources or obtained elsewhere. The coding region for each target protein was amplified by PCR with the high fidelity AccuPrime Pfx DNA polymerase (Invitrogen) from their respective cDNA clones using primers designed for use with the In-Fusion Advantage PCR cloning kit (Clontech). The various EBD-containing expression plasmids were digested with the restriction enzyme BamHI and gel purified. The target gene PCR products were then cloned into the expression vectors at the BamHI restriction site following the standard In-fusion cloning protocol from Clontech. Following the cloning reactions chemically competent Acella cells (EdgeBio) were used for transformation.

Cell Growth and Lysis

Cultures were grown in LB medium supplied with 100 μg/mL ampicillin at 37° C. overnight. The following morning 150 μL of culture was pelleted, raised in fresh medium and added to start a 3 mL culture. The culture tubes were incubated with shaking at 37° C. for 2 hours. IPTG was then added to a final concentration of 0.2 mM and the tubes were shaken for additional 5 to 6 hrs at 25° C. The cells were collected by centrifugation and lysed chemically using the B-PER Reagent (Thermo). The suspensions were kept for 10 min at room temperature. The lysed solution was designated as a "total cell lysate". The "soluble fractions" and "pellet fractions" were separated following centrifugation. The total cell extracts, soluble fractions, and pellet fractions were used for the detection of protein expression and solubility, respectively.

Expression and Solubility Test

To evaluate protein expression and solubility, the total cell extract (T), soluble fraction (S), and pellet fraction (P) were separated by SDS-PAGE using NuPAGE 4-12% Bis-Tris Gels and the supplied reagents (Invitrogen). The proteins were transferred to PVDF membranes (Invitrogen) and probed with anti-His probe antibodies following a standard western blotting protocol. Following development, the protein gel blots were scanned with a flatbed scanner and the band intensity was compared between soluble and pellet fractions NIH ImageJ software.

Results: Comparison of Solubility-Enhancement by Artificial EBDs

In order to compare solubility-enhancement by various EBDs, proteins that were known to be insoluble were cloned into the pAquoProt series of expression vectors and overexpressed in E. coli under a standard set of conditions. The negative control for these experiments was the same target protein expressed from the unmodified AquoProt plasmid that did not harbor an EBD but does translationally fuse an N-terminal His-tag and EK cleavage site to the target protein. The human metalloproteinase inhibitor TIMP2 is an example of a protein that is entirely insoluble when expressed in E. coli with an N-terminal His-tag (FIG. 8A). However, when 5 unique EBDs ranging in length from 24 to 250 amino acids are included in the fusion tag, a portion of the recombinant TIMP2 is detectable in the soluble fraction (FIG. 8A). These results indicate that EBDs can vary greatly in composition and length and still improve the solubility of fusion partners. To evaluate the contribution of the primary amino acid sequence and overall physical properties to solubility enhancement, the TEV protease was expressed as a fusion to an N-terminal His-tag or three N-terminal EBDs that are composed of the same four amino acids and have similar physical properties but differ in primary amino acid sequence (Table 3). The solubility studies demonstrate that TEV protease solubility improves when fused to all three EBDs with similar physical characteristics but distinct primary sequences are fused to the N-terminus (FIG. 8B). We also tested whether fragments of longer EBDs could themselves be effective solubilization agents. The human B cell activating factor (TNSF13b) was translationally fused to an N terminal tag containing a 120 amino acid EBD and a tag containing a 60 amino acid fragment of the longer EBD. Both EBDs improved the solubility of TNSF13b over the His-tag control construct (FIG. 8C). In some examples a single EBD fusion was insufficient to drastically improve the solubility of a partner. Therefore, the AquoKin expression vector was prepared to facilitate the addition of EBD fusion to both termini of a target protein. To demonstrate the effectiveness of this strategy, the tyrosine kinase c-Src was expressed with an N-terminal His tag or 250 amino acid EBD (SeqID 15 (1-250). The N-terminal EBD did improve c-Src solubility somewhat (FIG. 8D). However, when a second EBD (SeqID 15 (1-81)) was added to the C-terminus of c-Src the majority of the fusion protein was detected in the soluble fraction (FIG. 8D).

Conclusions

In summary, the translational fusion of negatively charged EBDs to recalcitrant proteins can dramatically improve solubility. Moreover, the EBDs are defined not by a specific amino acid sequence but instead by their physical properties. These results clearly demonstrate that synthetic polypeptides that are disordered and charged make for effective EBDs. The EBDs can be synthesized, for example, by combining disorder-promoting amino acids in a large variety of amino acid compositions and ratios. The variety of potential EBDs is further expanded by specifically engineering variants to contain specific desired features (e.g. hydrophobic pockets like those found in chaperone proteins; SEQ ID NO 45). The effective length of EBDs is also not fixed as demonstrated by the fact that EBDs ranging in length from 24 to 250 can be effectively employed. Adding EBDs to both termini of a target protein has also been shown to improve solubility over recombinant proteins that have a single fusion tag, demonstrating yet another solubilization strategy according to the present invention.

What is claimed:

1. An isolated fusion polypeptide comprising an entropic bristle domain (EBD) as set forth in SEQ ID NO selected from the group consisting of SEQ ID NO: 1, SEQ ID NO: 11, SEQ ID NO: 40, SEQ ID NO: 43 and SEQ ID NO: 44, or a fragment thereof, or a sequence having at least 90% identity to SEQ ID NO: 1, SEQ ID NO: 11, SEQ ID NO: 40, SEQ ID NO: 43 or SEQ ID NO: 44, and at least one heterologous polypeptide sequence, wherein the fusion polypeptide comprising said EBD, or said fragment thereof, or said sequence having 90% identity to SEQ ID NO: 1, SEQ ID NO: 11, SEQ ID NO: 40, SEQ ID NO: 43 or SEQ ID NO: 44 has increased solubility relative to the heterologous polypeptide sequence, reduced aggregation relative to the heterologous polypeptide sequence and/or improved folding relative to the heterologous polypeptide sequence.

2. The fusion polypeptide of claim 1, wherein the EBD polypeptide sequence is positively charged and the amino acid residues are disorder-promoting amino acid residues selected from P, Q, S and K.

3. The fusion polypeptide of claim 2, wherein the disorder-promoting amino acid residues P, Q, S and K are present in about the following amino acid ratios: K:P:Q:S=1:2:1:1, K:P:Q:S=1:4:1:1, K:P:Q:S=2:2:1:1, K:P:Q:S=3:2:1:1, K:P:Q:S=1:2:1:2, K:P:Q:S=2:2:1:2, K:P:Q:S=3:2:1:2, K:P:Q:S=4:2:1:2, or K:P:Q:S=5:2:1:2.

4. The fusion polypeptide of claim 1, wherein the EBD polypeptide sequence is negatively charged and the amino acid residues are disorder-promoting amino acid residues selected from P, Q, S and E.

5. The fusion polypeptide of claim 4, wherein the disorder-promoting amino acid residues P, Q, S and E are present in about the following amino acid ratios: E:P:Q:S=1:2:1:1, E:P:Q:S=1:4:1:1, E:P:Q:S=2:2:1:1, E:P:Q:S=3:2:1:1, E:P:Q:S=1:2:1:2, E:P:Q:S=2:2:1:2, E:P:Q:S=3:2:1:2, E:P:Q:S=4:2:1:2, or E:P:Q:S=5:2:1:2.

6. The fusion polypeptide of claim 1, wherein the EBD polypeptide sequence is negatively charged and the amino acid residues are disorder-promoting amino acid residues selected from P, Q, G and E.

7. The fusion polypeptide of claim 6, wherein the disorder-promoting amino acid residues P, Q, G and E are present in about the following amino acid ratios: E:P:Q:G=1:2:1:1, E:P:Q:G=1:4:1:1, E:P:Q:G=2:2:1:1, E:P:Q:G=3:2:1:1, E:P:Q:G=1:2:1:2, E:P:Q:G=2:2:1:2, E:P:Q:G=3:2:1:2, E:P:Q:G=4:2:1:2, or E:P:Q:G=5:2:1:2.

8. The fusion polypeptide of claim 1, wherein the EBD polypeptide sequence is negatively charged and the amino acid residues are disorder-promoting amino acid residues selected from P, Q, S, G, D and E.

9. The fusion polypeptide of claim 8, wherein the disorder-promoting amino acid residues P, Q, S, G, D and E are present in about the following amino acid ratios: D:E:P:Q:S:G=1:2:3:1:2:1.

10. The fusion polypeptide of claim 1, wherein said EBD polypeptide sequence is neutral and the amino acid residues are selected from P, Q, S and G. 18.

11. The fusion polypeptide of claim 10, wherein the disorder-promoting residues P, Q, S and G are present in about the amino acid ratio of G:P:Q:S=1:2:1:2.

12. The fusion polypeptide of claim 1, wherein said EBD polypeptide sequence is positively charged and the amino acid residues are disorder-promoting amino acid residues are selected from P, Q, S and R. 21.

13. The fusion polypeptide of claim 12, wherein the amino acid residues R, P, Q and S are present in about the following amino acid ratios: R:P:Q:S=1:2:1:2, R:P:Q:S=2:2:1:2, R:P:Q:S=3:2:1:2, R:P:Q:S=4:2:1:2, or R:P:Q:S=5:2:1:2.

14. The fusion polypeptide of claim 1, wherein the EBD polypeptide sequence is negatively charged and the amino acid residues are disorder-promoting amino acid residues are selected from P, Q, S and D.

15. The fusion polypeptide of claim 14, wherein the amino acid residues D, P, Q and S are present in about the following amino acid ratios: D:P:Q:S=1:2:1:2, D:P:Q:S=2:2:1:2, D:P:Q:S=3:2:1:2, D:P:Q:S=4:2:1:2, or D:P:Q:S=5:2:1:2.

16. The fusion polypeptide of claim 1, wherein the EBD polypeptide sequence is about 25-300 amino acids in length.

17. The fusion polypeptide of claim 1, wherein the EBD polypeptide sequence is about 25-200 amino acids in length.

18. The fusion polypeptide of claim 1, wherein the fusion polypeptide further comprises a cleavable linker.

19. The fusion polypeptide of claim 1, wherein the fusion polypeptide comprises an EBD sequence selected from the group consisting of SEQ ID NO: 1, SEQ ID NO: 11, SEQ ID NO: 40, SEQ ID NO: 43 and SEQ ID NO: 44.

20. The fusion polypeptide of claim 1, wherein the fusion polypeptide comprises a fragment of an EBD sequence selected from the group consisting of SEQ ID NO: 1, SEQ ID NO: 11, SEQ ID NO: 40, SEQ ID NO: 43 and SEQ ID NO: 44.

21. The fusion polypeptide of claim 1, wherein the fusion polypeptide comprises an EBD sequence having at least 90% identity to a sequence selected from the group consisting of SEQ ID NO: 1, SEQ ID NO: 11, SEQ ID NO: 40, SEQ ID NO: 43 and SEQ ID NO: 44.

22. The fusion polypeptide of claim 1, wherein the EBD sequence is covalently linked to the heterologous polypeptide sequence at the N-terminus, the C-terminus, or at both the N-terminus and C-terminus, of the heterologous polypeptide sequence.

* * * * *

SEQUENCE LISTING

<160> NUMBER OF SEQ ID NOS: 59

<210> SEQ ID NO 1
<211> LENGTH: 1000
<212> TYPE: PRT
<213> ORGANISM: Artificial Sequence
<220> FEATURE:
<223> OTHER INFORMATION: Randomly generated sequence, created by ExPASy
      WWW server tool

<400> SEQUENCE: 1

```
Ser Gln Ser Pro Lys Pro Ser Gln Ser Gln Ser Gln Pro Pro Ser
 1               5                  10                  15

Ser Lys Lys Ser Lys Gln Gln Gln Gln Pro Lys Ser Pro Ser Ser
                20                  25                  30

Pro Gln Ser Gln Ser Pro Ser Ser Pro Ser Ser Ser Pro Ser Gln
                35                  40                  45

Gln Pro Ser Lys Ser Ser Lys Ser Pro Lys Pro Ser Pro Ser Pro
        50                  55                  60

Pro Pro Ser Lys Lys Pro Lys Ser Pro Ser Lys Pro Ser Pro Lys Pro
65                  70                  75                  80

Pro Ser Pro Pro Lys Ser Lys Ser Pro Lys Gln Pro Gln Ser Ser Ser
                    85                  90                  95

Gln Ser Gln Ser Ser Ser Ser Lys Ser Ser Gln Pro Pro Ser Pro Pro
                100                 105                 110

Ser Ser Gln Lys Pro Ser Gln Ser Gln Ser Ser Gln Pro Lys Pro
                115                 120                 125

Ser Ser Pro Lys Pro Gln Ser Ser Pro Gln Lys Gln Ser Pro Ser Gln
130                 135                 140

Pro Lys Lys Ser Gln Lys Pro Lys Lys Gln Lys Lys Pro Gln Gln Pro
145                 150                 155                 160

Ser Ser Pro Gln Pro Lys Pro Gln Ser Ser Gln Pro Pro Gln Pro Gln Ser
                    165                 170                 175

Ser Ser Ser Lys Ser Ser Pro Gln Ser Ser Gln Gln Ser Ser Gln Ser
                180                 185                 190

Pro Pro Pro Pro Pro Pro Ser Ser Ser Ser Pro Lys Ser Lys Pro
                195                 200                 205

Ser Lys Pro Gln Ser Gln Lys Pro Pro Ser Pro Ser Ser Lys Pro Lys
                210                 215                 220

Ser Lys Ser Ser Pro Gln Lys Ser Ser Ser Pro Lys Ser Lys Lys
225                 230                 235                 240

Ser Pro Gln Pro Pro Lys Gln Gln Ser Pro Ser Lys Pro Pro Pro Lys
                245                 250                 255

Ser Pro Gln Pro Lys Pro Ser Pro Pro Ser Ser Pro Lys Lys Pro Lys
                260                 265                 270

Pro Pro Pro Ser Pro Lys Ser Gln Ser Ser Gln Pro Ser Pro Lys
                275                 280                 285

Ser Lys Ser Gln Pro Pro Ser Ser Ser Gln Pro Ser Pro Ser Ser Ser
                290                 295                 300

Gln Gln Ser Gln Ser Pro Gln Pro Ser Ser Gln Lys Pro Pro Gln Ser
305                 310                 315                 320

Pro Ser Gln Lys Ser Lys Lys Ser Ser Pro Ser Ser Pro Pro Pro Pro
                    325                 330                 335

Pro Ser Pro Pro Ser Gln Lys Gln Pro Pro Pro Pro Ser Ser Pro Lys
                340                 345                 350
```

Pro Pro Pro Gln Gln Ser Pro Gln Lys Ser Pro Lys Ser Pro Lys Gln
        355                 360                 365

Ser Lys Gln Ser Pro Pro Ser Gln Pro Ser Pro Pro Pro Pro Pro Ser
    370                 375                 380

Ser Pro Gln Pro Lys Pro Ser Ser Gln Pro Lys Pro Gln Ser Lys Gln
385                 390                 395                 400

Pro Gln Gln Pro Ser Lys Ser Lys Pro Pro Pro Gln Ser Lys Pro
                405                 410                 415

Pro Pro Gln Ser Pro Ser Lys Pro Gln Gln Gln Pro Ser Pro Pro Lys
                420                 425                 430

Pro Pro Ser Lys Pro Lys Pro Pro Gln Pro Lys Ser Lys Ser Lys
                435                 440                 445

Lys Pro Lys Gln Ser Pro Lys Ser Pro Lys Ser Pro Lys Lys Ser
                450                 455                 460

Ser Gln Lys Ser Ser Ser Pro Pro Gln Ser Pro Lys Lys Gln Lys Ser
465                 470                 475                 480

Gln Ser Pro Ser Ser Ser Gln Pro Pro Lys Pro Pro Lys Pro Pro Ser
                485                 490                 495

Ser Pro Pro Pro Pro Ser Ser Ser Lys Pro Pro Ser Lys Lys Pro Gln
                500                 505                 510

Ser Ser Ser Ser Ser Pro Ser Pro Ser Gln Gln Pro Gln Pro Ser Ser
                515                 520                 525

Pro Ser Gln Pro Pro Pro Ser Ser Pro Pro Pro Gln Pro Ser Gln
                530                 535                 540

Pro Pro Ser Pro Ser Ser Lys Lys Lys Gln Lys Gln Pro Gln Gln Lys
545                 550                 555                 560

Pro Pro Gln Gln Gln Ser Gln Lys Ser Lys Gln Lys Gln Lys
                565                 570                 575

Ser Ser Pro Pro Pro Ser Ser Ser Pro Ser Lys Lys Pro Pro Pro
                580                 585                 590

Pro Ser Ser Pro Lys Ser Gln Lys Lys Lys Pro Pro Ser Gln Pro Ser
                595                 600                 605

Pro Gln Pro Ser Ser Ser Gln Ser Pro Ser Gln Gln Ser Gln Ser Lys
                610                 615                 620

Pro Ser Ser Ser Pro Gln Pro Ser Pro Gln Pro Lys Ser Gln Ser Pro
625                 630                 635                 640

Gln Ser Gln Lys Pro Ser Pro Gln Ser Ser Pro Ser Lys Ser Lys Pro
                645                 650                 655

Pro Ser Ser Ser Ser Gln Pro Lys Pro Ser Ser Pro Ser Gln Gln Pro
                660                 665                 670

Ser Gln Pro Pro Lys Ser Ser Lys Ser Lys Gln Pro Pro Pro Ser
                675                 680                 685

Gln Gln Pro Ser Pro Lys Gln Ser Ser Ser Ser Pro Lys Lys Lys Pro
            690                 695                 700

Pro Gln Pro Pro Lys Lys Gln Ser Gln Gln Lys Pro Pro Gln Pro
705                 710                 715                 720

Pro Pro Pro Ser Pro Pro Pro Gln Gln Lys Ser Ser Ser Lys
                725                 730                 735

Ser Lys Gln Lys Ser Lys Pro Ser Pro Ser Gln Ser Pro Ser Pro
                740                 745                 750

Pro Ser Pro Pro Pro Gln Ser Pro Lys Gln Lys Ser Ser Lys Ser
                755                 760                 765

Pro Pro Lys Gln Pro Ser Pro Pro Gln Pro Gln Ser Pro Lys Lys Gln 770                 775                 780
Pro Gln Lys Ser Pro Pro Ser Gln Ser Pro Ser Gln Ser Ser Pro
785                 790                 795                 800

Gln Pro Ser Pro Pro Pro Ser Ser Ser Gln Ser Pro Pro Pro Lys
                    805                 810                 815

Ser Ser Gln Ser Ser Ser Ser Ser Lys Pro Pro Ser Pro Pro Lys
                820                 825                 830

Pro Pro Pro Gln Pro Ser Pro Gln Ser Ser Gln Pro Gln Lys Lys Ser
                835                 840                 845

Gln Pro Ser Ser Ser Lys Ser Pro Lys Pro Pro Pro Ser Ser Lys
850                 855                 860

Pro Pro Lys Gln Ser Ser Pro Lys Pro Ser Gln Pro Pro Ser Ser Gln
865                 870                 875                 880

Ser Lys Gln Gln Lys Gln Ser Lys Lys Lys Ser Lys Lys Pro Ser
                885                 890                 895

Pro Pro Lys Lys Ser Lys Gln Pro Gln Pro Gln Ser Pro Ser Lys Ser
                900                 905                 910

Pro Lys Lys Pro Ser Ser Lys Ser Ser Lys Ser Pro Pro Lys Ser Ser
                915                 920                 925

Pro Ser Ser Pro Ser Lys Ser Pro Pro Gln Lys Pro Pro Ser Gln Lys
930                 935                 940

Ser Ser Lys Pro Pro Pro Ser Ser Ser Gln Ser Lys Pro Gln Gln
945                 950                 955                 960

Ser Pro Lys Pro Ser Lys Pro Ser Pro Ser Ser Ser Pro Pro
                965                 970                 975

Gln Gln Gln Ser Ser Ser Lys Gln Ser Gln Ser Pro Pro Pro
                980                 985                 990

Ser Ser Pro Ser Pro Ser Pro Ser
                995                 1000

<210> SEQ ID NO 2
<211> LENGTH: 1000
<212> TYPE: PRT
<213> ORGANISM: Artificial Sequence
<220> FEATURE:
<223> OTHER INFORMATION: Randomly generated sequence, created by ExPASy
      WWW server tool

<400> SEQUENCE: 2

Lys Pro Pro Pro Lys Ser Gln Lys Lys Ser Ser Lys Lys Pro Gln Gln
1               5                   10                  15

Lys Ser Ser Lys Ser Pro Lys Ser Lys Ser Ser Lys Pro Gln Lys
                20                  25                  30

Gln Lys Ser Lys Pro Pro Lys Ser Lys Ser Gln Pro Pro Lys Lys Ser
                35                  40                  45

Lys Gln Pro Ser Lys Lys Lys Pro Ser Lys Pro Pro Lys Ser
50                  55                  60

Lys Gln Gln Lys Pro Lys Lys Ser Pro Ser Pro Pro Gln Ser
65                  70                  75                  80

Pro Ser Ser Lys Lys Lys Pro Ser Ser Ser Pro Lys Pro Lys Lys
                85                  90                  95

Pro Ser Pro Pro Ser Ser Lys Ser Lys Lys Pro Lys Ser Pro Ser Pro
                100                 105                 110

Ser Lys Ser Lys Gln Gln Ser Pro Gln Lys Ser Pro Ser Pro Lys Ser
                115                 120                 125

Lys Gln Gln Ser Ser Lys Lys Ser Pro Ser Ser Ser Gln Ser Pro Pro

```
            130                 135                 140
Lys Ser Lys Lys Ser Ser Lys Ser Ser Lys Lys Ser Pro Ser Gln
145                 150                 155                 160

Lys Lys Gln Pro Gln Pro Gln Ser Ser Pro Lys Pro Pro Gln Pro
                165                 170                 175

Lys Pro Ser Pro Lys Pro Ser Ser Ser Pro Pro Lys Pro Gln Gln
            180                 185                 190

Pro Pro Lys Pro Pro Ser Gln Lys Ser Pro Lys Pro Lys Pro Ser
                195                 200                 205

Ser Pro Ser Gln Lys Lys Ser Ser Gln Lys Ser Lys Gln Lys Gln Pro
210                 215                 220

Pro Pro Pro Ser Ser Lys Pro Ser Lys Ser Lys Pro Lys Lys Lys
225                 230                 235                 240

Ser Ser Pro Lys Gln Pro Pro Ser Pro Gln Gln Ser Ser Lys Pro
                245                 250                 255

Lys Lys Ser Ser Ser Ser Gln Lys Ser Pro Pro Gln Lys Gln Gln Lys
                260                 265                 270

Pro Ser Ser Gln Ser Ser Ser Pro Pro Gln Ser Lys Ser Lys Lys
    275                 280                 285

Ser Ser Pro Lys Lys Ser Pro Pro Lys Ser Lys Pro Ser Gln Pro Gln
    290                 295                 300

Pro Ser Ser Ser Lys Pro Lys Ser Lys Ser Gln Gln Ser Ser
305                 310                 315                 320

Ser Ser Gln Lys Lys Pro Ser Gln Gln Gln Pro Ser Ser Pro Lys Lys
                325                 330                 335

Pro Gln Ser Pro Pro Ser Pro Pro Lys Pro Pro Pro Gln Ser
                340                 345                 350

Ser Ser Ser Lys Ser Pro Pro Lys Lys Ser Lys Ser Ser Pro Lys Gln
        355                 360                 365

Pro Pro Ser Pro Pro Ser Gln Ser Ser Gln Gln Ser Ser Lys Ser Ser
370                 375                 380

Pro Ser Pro Pro Lys Lys Lys Lys Gln Pro Lys Gln Ser Lys Pro Lys
385                 390                 395                 400

Gln Gln Pro Ser Lys Gln Ser Lys Lys Lys Pro Pro Pro Gln Pro Lys
                405                 410                 415

Lys Ser Pro Gln Lys Gln Lys Ser Gln Pro Lys Lys Gln Gln Lys
                420                 425                 430

Pro Ser Pro Gln Pro Lys Ser Ser Lys Ser Ser Lys Pro Ser Ser
                435                 440                 445

Pro Lys Lys Lys Pro Gln Ser Ser Pro Pro Gln Gln Lys Gln Pro Ser
450                 455                 460

Lys Pro Pro Gln Ser Pro Ser Pro Gln Lys Gln Lys Ser Pro Gln
465                 470                 475                 480

Pro Pro Ser Pro Pro Lys Ser Pro Gln Pro Lys Lys Ser Lys Ser
                485                 490                 495

Ser Ser Ser Lys Ser Lys Lys Ser Ser Ser Gln Lys Pro Pro Pro Gln
                500                 505                 510

Pro Lys Pro Ser Gln Pro Lys Ser Pro Pro Ser Gln Ser Lys Lys Pro
                515                 520                 525

Ser Lys Pro Pro Ser Pro Pro Ser Lys Pro Lys Gln Pro Gln Ser Pro
    530                 535                 540

Lys Ser Lys Gln Gln Ser Ser Pro Pro Ser Ser Pro Ser Lys Ser Lys
545                 550                 555                 560
```

-continued

Gln Lys Pro Pro Lys Gln Ser Gln Pro Ser Gln Pro Pro Lys
            565                 570                 575

Ser Pro Ser Pro Ser Pro Lys Ser Lys Pro Lys Pro Lys Pro Ser
        580                 585                 590

Gln Ser Ser Lys Ser Ser Lys Lys Lys Pro Ser Lys Pro Pro Ser Gln
        595                 600                 605

Ser Pro Ser Gln Lys Lys Ser Ser Lys Ser Pro Pro Pro Lys Ser Lys
        610                 615                 620

Pro Pro Pro Ser Gln Ser Pro Lys Ser Lys Lys Ser Pro Ser Gln
625                 630                 635                 640

Lys Ser Lys Lys Lys Lys Gln Lys Lys Pro Lys Pro Lys Pro Pro
                645                 650                 655

Ser Gln Lys Lys Gln Gln Lys Ser Ser Ser Pro Pro Pro Ser Lys Lys
        660                 665                 670

Ser Ser Pro Ser Lys Ser Lys Pro Pro Ser Pro Pro Ser Lys Lys Ser
            675                 680                 685

Ser Lys Ser Pro Pro Pro Lys Lys Pro Pro Pro Gln Ser Pro Ser
        690                 695                 700

Pro Lys Gln Ser Pro Gln Pro Lys Lys Pro Ser Lys Ser Ser Pro Pro
705                 710                 715                 720

Gln Gln Ser Pro Lys Lys Ser Pro Lys Gln Pro Pro Ser Lys Pro
                725                 730                 735

Lys Pro Lys Pro Pro Pro Lys Gln Lys Pro Ser Ser Lys Pro Gln Lys
            740                 745                 750

Ser Ser Ser Lys Ser Lys Lys Pro Lys Pro Pro Ser Lys Gln Ser Gln
        755                 760                 765

Lys Lys Ser Lys Gln Pro Gln Ser Pro Gln Pro Ser Ser Lys Gln Lys
770                 775                 780

Pro Lys Pro Lys Gln Ser Ser Pro Pro Lys Ser Lys Ser Lys Lys
785                 790                 795                 800

Pro Pro Gln Lys Lys Pro Ser Gln Pro Lys Ser Ser Lys Pro Ser Ser
                805                 810                 815

Lys Pro Lys Lys Lys Gln Pro Pro Pro Gln Pro Lys Pro Pro Gln
            820                 825                 830

Lys Lys Ser Lys Gln Ser Ser Lys Ser Pro Pro Pro Ser Lys Lys
        835                 840                 845

Ser Lys Pro Ser Lys Lys Ser Gln Gln Gln Lys Ser Gln Ser Pro Ser
850                 855                 860

Pro Lys Ser Ser Pro Pro Ser Pro Lys Pro Lys Ser Pro Pro Pro
865                 870                 875                 880

Ser Ser Ser Pro Ser Ser Ser Pro Ser Ser Lys Pro Pro Ser Ser
                885                 890                 895

Gln Ser Gln Lys Lys Gln Ser Pro Lys Gln Pro Ser Lys Gln Lys
            900                 905                 910

Ser Ser Pro Pro Lys Lys Ser Lys Pro Lys Pro Pro Pro Ser
        915                 920                 925

Pro Ser Ser Lys Lys Lys Pro Lys Pro Ser Lys Ser Lys Lys Pro
930                 935                 940

Pro Ser Pro Lys Gln Lys Lys Ser Lys Gln Lys Ser Lys Pro Lys Pro
945                 950                 955                 960

Pro Lys Gln Pro Gln Ser Ser Gln Pro Pro Lys Gln Pro Lys Pro Gln
                965                 970                 975

Gln Gln Ser Gln Ser Ser Gln Pro Pro Gln Gln Ser Gln Lys Pro Gln
            980                 985                 990

```
Lys Pro Lys Ser Pro Gln Gln Ser
        995                 1000

<210> SEQ ID NO 3
<211> LENGTH: 1000
<212> TYPE: PRT
<213> ORGANISM: Artificial Sequence
<220> FEATURE:
<223> OTHER INFORMATION: Randomly generated sequence, created by ExPASy
      WWW server tool

<400> SEQUENCE: 3

Gln Ser Ser Ser Pro Pro Lys Ser Ser Gln Ser Lys Ser Ser
 1               5                  10                 15

Ser Ser Ser Ser Ser Pro Ser Pro Lys Ser Pro Ser Pro Ser Lys
            20                  25                  30

Pro Pro Pro Pro Ser Lys Lys Lys Pro Lys Ser Lys Lys Gln Ser
            35                  40                  45

Ser Pro Lys Ser Ser Lys Pro Lys Lys Pro Lys Gln Lys Lys Ser Pro
 50                  55                  60

Pro Pro Gln Lys Pro Lys Lys Ser Pro Ser Lys Pro Lys Ser Lys Pro
 65                  70                  75                  80

Ser Ser Ser Lys Lys Lys Ser Gln Gln Gln Ser Ser Gln Lys Ser
            85                  90                  95

Gln Ser Lys Gln Pro Lys Lys Pro Gln Pro Ser Pro Lys Lys Pro Lys
                 100                 105                 110

Ser Pro Lys Lys Pro Pro Lys Pro Gln Pro Lys Ser Ser Pro Lys Gln
            115                 120                 125

Ser Lys Gln Lys Pro Ser Lys Lys Pro Ser Ser Lys Pro Lys Ser
            130                 135                 140

Lys Ser Lys Lys Ser Gln Lys Pro Lys Gln Ser Lys Lys Ser Ser
145                 150                 155                 160

Ser Lys Pro Pro Ser Lys Ser Lys Lys Gln Pro Lys Pro Lys Lys
            165                 170                 175

Lys Ser Lys Ser Ser Ser Ser Lys Ser Ser Lys Ser Pro Ser Lys Ser
            180                 185                 190

Lys Ser Pro Gln Ser Ser Lys Ser Ser Pro Pro Lys Lys Pro Lys Pro
            195                 200                 205

Lys Lys Pro Lys Pro Lys Ser Ser Lys Ser Lys Ser Pro Pro Lys
            210                 215                 220

Lys Lys Pro Gln Ser Gln Lys Gln Pro Lys Ser Gln Ser Pro Gln Pro
225                 230                 235                 240

Gln Lys Lys Pro Lys Gln Ser Ser Lys Gln Lys Pro Lys Ser Lys Lys
                 245                 250                 255

Ser Pro Lys Lys Pro Pro Lys Lys Ser Lys Pro Lys Ser Pro Pro Pro
            260                 265                 270

Pro Lys Lys Pro Lys Pro Lys Lys Ser Ser Lys Gln Pro Lys Ser Gln
            275                 280                 285

Ser Ser Gln Lys Lys Pro Lys Pro Pro Pro Ser Pro Pro Lys Gln
            290                 295                 300

Lys Pro Gln Lys Ser Ser Ser Pro Pro Lys Gln Gln Ser Lys Lys Pro
305                 310                 315                 320

Ser Pro Pro Gln Lys Pro Lys Pro Lys Ser Ser Pro Ser Pro Ser Lys
                 325                 330                 335

Ser Ser Gln Ser Lys Lys Lys Lys Pro Lys Lys Pro Lys Gln Ser Pro
                 340                 345                 350
```

```
Pro Gln Lys Pro Pro Ser Lys Gln Ser Pro Gln Lys Pro Lys Ser Ser
        355                 360                 365

Ser Pro Pro Lys Lys Lys Ser Ser Lys Lys Gln Lys Lys Lys Lys Gln
    370                 375                 380

Lys Lys Gln Lys Ser Gln Ser Lys Pro Ser Gln Lys Pro Pro Lys Ser
385                 390                 395                 400

Lys Pro Lys Ser Ser Ser Lys Lys Gln Ser Lys Lys Lys Lys Lys Lys
            405                 410                 415

Pro Pro Gln Lys Ser Ser Lys Gln Gln Ser Pro Pro Lys Gln Lys Ser
        420                 425                 430

Pro Lys Pro Ser Pro Lys Lys Lys Pro Lys Lys Lys Gln Lys Pro Lys
    435                 440                 445

Ser Pro Lys Gln Ser Gln Pro Lys Lys Pro Lys Pro Ser Lys Pro Gln
450                 455                 460

Lys Ser Gln Lys Lys Ser Pro Ser Pro Lys Pro Pro Pro Gln Pro Lys
465                 470                 475                 480

Pro Gln Lys Lys Ser Pro Pro Lys Pro Lys Pro Lys Ser Pro Ser Pro
            485                 490                 495

Pro Pro Ser Gln Lys Pro Lys Lys Pro Ser Lys Pro Gln Gln Ser Pro
        500                 505                 510

Gln Lys Lys Pro Pro Pro Lys Ser Gln Lys Lys Pro Lys Pro Pro Lys
        515                 520                 525

Lys Lys Ser Lys Ser Ser Ser Pro Pro Gln Ser Lys Gln Gln Lys Lys
    530                 535                 540

Lys Lys Lys Lys Ser Pro Ser Lys Lys Ser Lys Gln Pro Gln Pro
545                 550                 555                 560

Lys Gln Lys Lys Lys Ser Lys Pro Lys Ser Pro Ser Lys Pro Lys Lys
            565                 570                 575

Gln Ser Ser Ser Lys Gln Lys Lys Ser Pro Lys Pro Lys Pro Ser Pro
        580                 585                 590

Lys Ser Ser Lys Pro Gln Pro Lys Lys Lys Lys Pro Ser Lys Lys
    595                 600                 605

Lys Lys Lys Lys Lys Gln Lys Pro Pro Pro Gln Ser Lys Lys Pro Lys
    610                 615                 620

Ser Pro Pro Pro Lys Pro Lys Pro Lys Ser Ser Ser Lys Lys Pro Pro
625                 630                 635                 640

Pro Lys Pro Ser Lys Pro Gln Ser Lys Lys Gln Ser Lys Ser Lys Lys
            645                 650                 655

Lys Pro Pro Lys Gln Lys Lys Lys Pro Lys Lys Ser Pro Lys Lys Lys
        660                 665                 670

Lys Lys Pro Pro Ser Ser Lys Ser Ser Pro Lys Ser Pro Pro Ser Gln
    675                 680                 685

Gln Ser Pro Pro Pro Lys Gln Ser Lys Gln Pro Pro Ser Gln Ser
        690                 695                 700

Lys Lys Pro Pro Lys Pro Pro Lys Lys Ser Ser Lys Lys Lys Lys
705                 710                 715                 720

Lys Ser Lys Lys Pro Gln Lys Gln Pro Lys Lys Ser Ser Lys
            725                 730                 735

Gln Ser Lys Ser Lys Pro Pro Ser Pro Ser Pro Pro Ser Pro Ser
        740                 745                 750

Lys Pro Pro Ser Pro Lys Lys Lys Ser Pro Ser Gln Ser Lys Pro Lys
    755                 760                 765

Gln Lys Ser Pro Ser Lys Ser Ser Lys Ser Lys Gln Ser Lys Pro Ser
```

```
                    770                 775                 780
Lys Gln Gln Pro Lys Gln Lys Pro Gln Ser Ser Gln Lys Pro Lys Ser
785                 790                 795                 800

Pro Lys Ser Lys Lys Ser Gln Lys Lys Gln Ser Ser Ser Pro Pro
                805                 810                 815

Lys Ser Lys Ser Gln Gln Pro Lys Pro Ser Gln Lys Lys Pro Pro Lys
                820                 825                 830

Gln Gln Ser Ser Lys Ser Pro Gln Lys Ser Ser Lys Gln Lys Pro Ser
                835                 840                 845

Lys Pro Ser Ser Pro Lys Pro Gln Ser Lys Gln Ser Lys Gln Gln Lys
                850                 855                 860

Lys Lys Lys Gln Ser Lys Gln Pro Pro Lys Gln Lys Lys Pro Ser Lys
865                 870                 875                 880

Ser Lys Lys Pro Pro Pro Lys Pro Pro Lys Ser Lys Pro Lys Gln
                885                 890                 895

Lys Lys Pro Gln Lys Lys Pro Lys Ser Ser Lys Pro Gln Gln Pro
                900                 905                 910

Ser Pro Ser Ser Pro Ser Ser Lys Ser Ser Lys Ser Lys Ser Lys
                915                 920                 925

Gln Lys Pro Pro Pro Gln Pro Pro Ser Gln Lys Lys Lys Lys Pro
                930                 935                 940

Pro Pro Lys Ser Gln Lys Lys Pro Lys Lys Lys Ser Ser Pro Ser
945                 950                 955                 960

Lys Lys Lys Pro Pro Lys Lys Lys Ser Pro Ser Gln Ser Ser Gln Lys
                965                 970                 975

Ser Lys Ser Ser Ser Gln Ser Pro Pro Gln Gln Pro Pro Gln Lys Pro
                980                 985                 990

Lys Lys Ser Lys Gln Lys Lys Lys
                995                 1000

<210> SEQ ID NO 4
<211> LENGTH: 1000
<212> TYPE: PRT
<213> ORGANISM: Artificial Sequence
<220> FEATURE:
<223> OTHER INFORMATION: Randomly generated sequence, created by ExPASy
      WWW server tool

<400> SEQUENCE: 4

Ser Ser Lys Pro Lys Lys Ser Pro Pro Ser Lys Lys Gln Ser Gln Ser
  1               5                  10                  15

Lys Lys Ser Lys Pro Lys Lys Lys Ser Gln Lys Pro Lys Lys Ser
                 20                  25                  30

Ser Pro Lys Lys Lys Ser Lys Ser Ser Lys Pro Ser Pro Pro Gln
                 35                  40                  45

Pro Ser Lys Gln Pro Lys Gln Gln Ser Pro Ser Lys Gln Ser Lys Ser
                 50                  55                  60

Pro Lys Ser Gln Lys Pro Pro Ser Pro Lys Lys Gln Lys Lys
65                  70                  75                  80

Pro Ser Lys Gln Pro Lys Ser Pro Lys Pro Pro Lys Ser Lys Ser Gln
                 85                  90                  95

Gln Pro Lys Pro Lys Pro Gln Pro Lys Lys Pro Lys Pro Ser
                100                 105                 110

Lys Pro Pro Pro Pro Ser Ser Gln Lys Gln Gln Lys Ser Lys Ser Pro
                115                 120                 125

Ser Gln Lys Lys Lys Lys Pro Ser Lys Lys Pro Lys Lys Lys Gln Pro
```

-continued

```
                130                 135                 140
Lys Gln Ser Pro Ser Ser Lys Pro Ser Ser Gln Pro Lys Gln Pro Pro
145                 150                 155                 160

Gln Lys Lys Lys Pro Lys Pro Lys Lys Lys Lys Gln Lys Gln
                165                 170                 175

Pro Lys Lys Pro Lys Lys Lys Ser Pro Lys Lys Pro Lys Pro
                180                 185                 190

Pro Lys Ser Lys Lys Lys Pro Lys Ser Ser Lys Lys Ser Lys Pro
                195                 200                 205

Gln Lys Pro Ser Pro Pro Lys Ser Pro Lys Pro Lys Pro Lys
210                 215                 220

Lys Lys Pro Lys Ser Lys Ser Lys Ser Lys Pro Lys Pro Pro
225                 230                 235                 240

Ser Lys Lys Lys Pro Pro Ser Pro Pro Ser Ser Pro Lys Gln Lys
                245                 250                 255

Ser Lys Ser Pro Pro Lys Lys Pro Lys Gln Lys Pro Lys Gln Lys
                260                 265                 270

Ser Lys Ser Ser Ser Pro Gln Pro Lys Pro Pro Ser Ser Pro Lys Lys
                275                 280                 285

Lys Lys Lys Gln Ser Lys Ser Lys Pro Ser Lys Lys Ser Pro Pro
290                 295                 300

Lys Lys Lys Lys Ser Gln Gln Lys Ser Ser Lys Pro Lys Lys Pro
305                 310                 315                 320

Lys Lys Ser Lys Lys Ser Ser Lys Lys Lys Ser Lys Pro Gln Ser Lys
                325                 330                 335

Pro Lys Ser Ser Lys Lys Lys Ser Ser Ser Lys Ser Ser Pro Lys
                340                 345                 350

Lys Pro Lys Pro Gln Gln Pro Lys Lys Lys Gln Gln Lys Lys Lys
                355                 360                 365

Lys Ser Ser Lys Pro Lys Gln Lys Lys Ser Gln Lys Lys Pro Ser Lys
                370                 375                 380

Lys Lys Pro Lys Lys Pro Lys Gln Lys Lys Ser Lys Lys Ser Pro Pro
385                 390                 395                 400

Lys Lys Gln Ser Lys Gln Pro Pro Gln Lys Lys Ser Lys Lys Lys Gln
                405                 410                 415

Lys Pro Pro Ser Gln Lys Lys Ser Gln Ser Ser Pro Lys Lys Pro
                420                 425                 430

Pro Gln Lys Pro Lys Lys Lys Ser Pro Lys Pro Pro Lys Lys Pro Gln
                435                 440                 445

Lys Lys Pro Lys Ser Lys Gln Ser Ser Ser Lys Pro Ser Lys Pro Pro
                450                 455                 460

Pro Pro Lys Lys Pro Pro Lys Lys Pro Lys Pro Lys Lys Lys Lys
465                 470                 475                 480

Lys Ser Lys Lys Ser Ser Lys Lys Lys Lys Gln Pro Ser Pro Lys Lys
                485                 490                 495

Pro Lys Ser Lys Lys Lys Lys Lys Ser Ser Lys Pro Ser Lys Pro Ser
                500                 505                 510

Gln Gln Lys Ser Pro Lys Ser Lys Pro Ser Ser Pro Gln Ser Lys
                515                 520                 525

Gln Pro Lys Gln Ser Ser Ser Lys Lys Pro Lys Lys Pro Pro
                530                 535                 540

Ser Lys Ser Lys Gln Pro Ser Ser Lys Ser Pro Lys Ser Pro Pro Pro
545                 550                 555                 560
```

-continued

| | | | | | | | | | | | | |
|---|---|---|---|---|---|---|---|---|---|---|---|---|
|Lys|Pro|Ser|Gln|Lys|Pro|Pro|Gln|Lys|Lys|Pro|Lys|Lys|
| | | |565| | | |570| | | |575| |
|Ser|Lys|Lys|Pro|Pro|Lys|Lys|Lys|Pro|Gln|Lys|Pro|Lys|
| | | |580| | | |585| | | |590| |
|Ser|Ser|Pro|Ser|Pro|Pro|Ser|Pro|Lys|Gln|Lys|Lys|Gln|Pro|
| | | |595| | | |600| | | |605| |
|Pro|Ser|Lys|Gln|Pro|Lys|Ser|Lys|Lys|Ser|Ser|Gln|Lys|Lys|Ser|Ser|
| | |610| | | |615| | | |620| | | |
|Lys|Ser|Lys|Lys|Lys|Lys|Lys|Lys|Pro|Pro|Lys|Lys|Ser|Lys|Ser|
|625| | | |630| | | |635| | | |640| |
|Pro|Pro|Ser|Gln|Ser|Lys|Ser|Lys|Pro|Ser|Pro|Pro|Lys|Lys|Pro|
| | | |645| | | |650| | | |655| |
|Lys|Lys|Gln|Ser|Ser|Gln|Gln|Ser|Lys|Ser|Gln|Gln|Ser|Ser|Lys|Pro|
| | | |660| | | |665| | | |670| | |
|Lys|Pro|Lys|Pro|Lys|Lys|Pro|Pro|Pro|Lys|Gln|Ser|Pro|Ser|Pro|Ser|
| | |675| | | |680| | | |685| | | |
|Ser|Gln|Lys|Lys|Lys|Pro|Lys|Ser|Lys|Lys|Pro|Ser|Ser|Pro|Ser|
| |690| | | |695| | | |700| | | |
|Ser|Pro|Lys|Ser|Ser|Pro|Ser|Ser|Ser|Pro|Ser|Lys|Ser|Ser|Lys|
|705| | | |710| | | |715| | | |720|
|Gln|Lys|Pro|Ser|Ser|Pro|Ser|Lys|Pro|Lys|Pro|Lys|Lys|Lys|Pro|
| | | |725| | | |730| | | |735|
|Lys|Lys|Lys|Pro|Lys|Lys|Pro|Lys|Lys|Gln|Pro|Lys|Gln|Lys|Pro|Lys|
| | | |740| | | |745| | | |750| |
|Lys|Pro|Pro|Pro|Ser|Lys|Lys|Pro|Lys|Pro|Pro|Ser|Lys|Ser|Gln|Ser|
| | | |755| | | |760| | | |765| |
|Lys|Lys|Pro|Lys|Gln|Lys|Lys|Ser|Ser|Pro|Lys|Lys|Lys|Ser|Lys|
| | |770| | | |775| | | |780| | |
|Lys|Ser|Lys|Lys|Ser|Lys|Gln|Gln|Lys|Gln|Lys|Lys|Lys|Ser|Gln|
|785| | | |790| | | |795| | | |800|
|Lys|Lys|Ser|Lys|Ser|Ser|Pro|Pro|Lys|Ser|Lys|Lys|Gln|Lys|Gln|Ser|
| | | |805| | | |810| | | |815| |
|Lys|Lys|Pro|Lys|Gln|Pro|Lys|Lys|Lys|Gln|Ser|Lys|Ser|Pro|Lys|Lys|
| | | |820| | | |825| | | |830| |
|Gln|Lys|Lys|Pro|Lys|Ser|Ser|Pro|Ser|Gln|Lys|Gln|Gln|Lys|Lys|
| | | |835| | | |840| | | |845| |
|Lys|Lys|Gln|Pro|Ser|Lys|Ser|Ser|Lys|Lys|Pro|Lys|Gln|Lys|Lys|Lys|
| | |850| | | |855| | | |860| | |
|Ser|Lys|Gln|Ser|Lys|Pro|Lys|Gln|Pro|Lys|Ser|Ser|Pro|Pro|Lys|
|865| | | |870| | | |875| | | |880|
|Ser|Pro|Ser|Lys|Gln|Ser|Lys|Lys|Ser|Pro|Ser|Lys|Ser|Gln|Lys|Pro|
| | | |885| | | |890| | | |895| |
|Gln|Ser|Lys|Lys|Ser|Pro|Lys|Ser|Lys|Lys|Ser|Ser|Lys|Lys|Lys|
| | |900| | | |905| | | |910| | |
|Lys|Lys|Lys|Lys|Lys|Pro|Lys|Lys|Pro|Lys|Lys|Pro|Lys|Lys|Ser|
| | |915| | | |920| | | |925| | |
|Lys|Ser|Ser|Ser|Gln|Lys|Lys|Ser|Lys|Lys|Gln|Pro|Lys|Ser|Pro|Ser|Gln|
| | |930| | | |935| | | |940| | | |
|Lys|Ser|Ser|Lys|Lys|Lys|Pro|Lys|Gln|Ser|Ser|Lys|Lys|Lys|Gln|
|945| | | |950| | | |955| | | |960|
|Lys|Lys|Gln|Lys|Gln|Lys|Lys|Lys|Gln|Pro|Ser|Ser|Lys|Pro|Gln|Pro|
| | | |965| | | |970| | | |975| |
|Lys|Lys|Lys|Gln|Pro|Lys|Lys|Lys|Gln|Lys|Lys|Pro|Lys|Lys|Lys|
| | | |980| | | |985| | | |990| |

```
Ser Pro Lys Ser Pro Lys Pro Lys
        995                 1000

<210> SEQ ID NO 5
<211> LENGTH: 1000
<212> TYPE: PRT
<213> ORGANISM: Artificial Sequence
<220> FEATURE:
<223> OTHER INFORMATION: Randomly generated sequence, created by ExPASy
      WWW server tool

<400> SEQUENCE: 5

Lys Lys Lys Gln Pro Lys Ser Gln Gln Lys Lys Lys Lys Lys
 1               5                  10                  15

Gln Ser Lys Pro Lys Gln Lys Pro Pro Ser Ser Lys Pro Pro Lys
            20                  25                  30

Gln Lys Lys Lys Gln Pro Lys Ser Pro Ser Lys Ser Ser Lys
            35                  40                  45

Lys Lys Gln Lys Ser Pro Lys Pro Gln Lys Lys Pro Lys Pro Lys
 50                  55                  60

Lys Pro Lys Lys Ser Lys Gln Pro Gln Gln Pro Pro Ser Lys Pro
 65                  70                  75                  80

Ser Pro Gln Ser Lys Ser Lys Gln Pro Gln Lys Lys Pro Pro Lys
            85                  90                  95

Pro Lys Pro Pro Lys Lys Pro Lys Lys Lys Gln Pro Ser Gln Lys
            100                 105                 110

Gln Ser Lys Pro Pro Lys Ser Gln Ser Gln Lys Lys Ser Ser Lys Gln
            115                 120                 125

Lys Ser Pro Ser Lys Pro Lys Gln Lys Ser Ser Lys Lys Lys Lys
 130                 135                 140

Lys Pro Ser Ser Ser Pro Ser Lys Ser Lys Lys Lys Pro Lys Ser
 145                 150                 155                 160

Lys Pro Pro Lys Lys Ser Lys Pro Lys Lys Lys Lys Ser Gln Ser
                    165                 170                 175

Lys Lys Pro Lys Lys Lys Pro Lys Gln Gln Gln Lys Pro Lys Pro
                    180                 185                 190

Ser Lys Gln Gln Lys Pro Lys Pro Ser Ser Lys Lys Ser Ser Pro Lys
            195                 200                 205

Lys Lys Pro Lys Gln Lys Pro Lys Pro Gln Pro Lys Pro Lys Lys Pro
 210                 215                 220

Lys Pro Pro Lys Pro Lys Gln Lys Lys Lys Ser Lys Pro Lys Pro Lys
 225                 230                 235                 240

Ser Pro Lys Lys Lys Gln Gln Gln Gln Pro Lys Pro Pro Gln Lys Ser
            245                 250                 255

Pro Lys Lys Ser Pro Pro Lys Lys Pro Lys Pro Lys Lys Ser Ser Pro
            260                 265                 270

Ser Lys Ser Pro Ser Lys Pro Lys Lys Gln Lys Pro Lys Lys Pro Ser
            275                 280                 285

Ser Gln Lys Lys Pro Lys Ser Lys Ser Pro Pro Lys Lys Gln Ser Lys
            290                 295                 300

Lys Ser Lys Ser Lys Ser Lys Lys Ser Pro Ser Ser Lys Lys Ser
 305                 310                 315                 320

Lys Pro Lys Lys Ser Ser Pro Lys Pro Lys Ser Lys Lys Gln Ser
                    325                 330                 335

Lys Ser Lys Ser Gln Lys Pro Lys Ser Lys Gln Ser Ser Pro Lys Gln
                    340                 345                 350
```

```
Lys Lys Lys Ser Gln Lys Ser Lys Pro Gln Lys Ser Lys Lys Ser
            355                 360                 365
Ser Pro Lys Lys Gln Lys Ser Lys Lys Lys Ser Pro Lys Lys Pro
        370                 375                 380
Ser Lys Pro Pro Lys Lys Pro Pro Lys Ser Gln Ser Lys Lys
385                 390                 395                 400
Lys Gln Ser Pro Lys Pro Lys Pro Pro Ser Pro Ser Pro Lys Pro Lys
                405                 410                 415
Lys Lys Ser Lys Lys Lys Lys Lys Gln Pro Ser Ser Lys Lys Gln
            420                 425                 430
Pro Lys Lys Pro Ser Lys Lys Lys Gln Ser Pro Ser Lys Gln Pro
        435                 440                 445
Lys Ser Lys Ser Ser Lys Lys Ser Pro Lys Lys Gln Pro Lys Lys
    450                 455                 460
Pro Lys Lys Lys Lys Gln Ser Ser Lys Lys Pro Lys Lys Ser Pro Gln
465                 470                 475                 480
Lys Lys Ser Lys Lys Pro Gln Ser Ser Pro Lys Lys Ser Pro Ser Lys
                485                 490                 495
Gln Pro Lys Lys Lys Pro Lys Pro Lys Lys Pro Lys Lys
            500                 505                 510
Lys Pro Gln Ser Ser Pro Ser Lys Pro Pro Lys Ser Gln Ser Lys
        515                 520                 525
Gln Lys Ser Pro Pro Lys Ser Ser Ser Lys Lys Gln Lys Lys Pro
    530                 535                 540
Lys Pro Lys Lys Lys Lys Pro Ser Lys Lys Lys Pro Pro Pro Ser
545                 550                 555                 560
Lys Lys Pro Lys Lys Ser Lys Lys Ser Lys Ser Lys Lys Lys Ser Lys
                565                 570                 575
Lys Lys Ser Pro Pro Lys Lys Ser Lys Lys Lys Gln Pro Lys Pro Pro
            580                 585                 590
Lys Lys Ser Lys Lys Lys Ser Ser Lys Gln Ser Lys Pro Lys Lys Ser
        595                 600                 605
Pro Lys Pro Lys Ser Lys Lys Lys Lys Lys Gln Lys Ser Ser Ser
    610                 615                 620
Lys Lys Ser Pro Pro Lys Ser Lys Pro Pro Lys Pro Ser Gln Pro
625                 630                 635                 640
Pro Lys Ser Lys Lys Lys Pro Pro Ser Lys Lys Pro Lys Lys
                645                 650                 655
Gln Lys Ser Ser Gln Lys Pro Lys Ser Ser Gln Lys Lys Lys Pro Pro
            660                 665                 670
Lys Pro Lys Lys Gln Pro Lys Ser Lys Lys Pro Lys Lys Pro Lys Lys
        675                 680                 685
Gln Gln Gln Lys Lys Pro Pro Lys Lys Lys Lys Lys Lys Lys Lys
    690                 695                 700
Lys Pro Lys Pro Lys Lys Pro Pro Lys Pro Gln Ser Lys Ser Lys Lys
705                 710                 715                 720
Lys Lys Lys Ser Pro Pro Ser Pro Pro Ser Pro Lys Lys Lys Lys
                725                 730                 735
Gln Lys Lys Lys Ser Lys Lys Lys Lys Pro Lys Lys Pro Gln Lys
            740                 745                 750
Lys Ser Ser Lys Gln Lys Lys Lys Pro Ser Ser Ser Lys Pro Lys
        755                 760                 765
Ser Gln Ser Lys Lys Ser Ser Lys Lys Pro Lys Gln Ser Lys Gln Lys
```

Lys Ser Gln Ser Lys Lys Ser Ser Lys Ser Lys Pro Gln Lys Lys
785                 790                 795                 800

Ser Lys Lys Lys Lys Lys Lys Pro Lys Lys Lys Lys Lys Lys
            805                 810                 815

Ser Lys Ser Lys Ser Ser Gln Ser Gln Lys Lys Lys Lys Ser Pro
            820                 825                 830

Lys Lys Lys Lys Lys Lys Ser Lys Lys Lys Ser Lys Ser Lys Pro Pro
            835                 840                 845

Lys Pro Lys Lys Gln Ser Lys Lys Ser Lys Ser Lys Pro Pro Ser
    850                 855                 860

Lys Pro Lys Ser Ser Lys Ser Lys Pro Lys Lys Pro Lys Lys Lys
865                 870                 875                 880

Lys Gln Lys Lys Lys Gln Lys Ser Lys Pro Ser Lys Lys Ser Pro Ser
                885                 890                 895

Lys Pro Pro Ser Lys Pro Ser Lys Gln Lys Lys Ser Gln Lys Lys
            900                 905                 910

Gln Pro Gln Pro Pro Lys Lys Gln Pro Pro Lys Ser Lys Pro Lys Pro
    915                 920                 925

Pro Lys Pro Gln Lys Ser Ser Lys Lys Lys Lys Pro Ser Lys Lys
930                 935                 940

Pro Pro Lys Lys Lys Ser Lys Lys Gln Lys Lys Lys Lys Ser Gln Ser
945                 950                 955                 960

Gln Lys Lys Ser Ser Ser Gln Lys Pro Lys Ser Lys Ser Ser Gln
            965                 970                 975

Lys Lys Pro Lys Lys Lys Ser Lys Ser Ser Lys Gln Lys Ser Lys Lys
            980                 985                 990

Gln Lys Ser Lys Lys Lys Pro Lys
        995                 1000

<210> SEQ ID NO 6
<211> LENGTH: 1000
<212> TYPE: PRT
<213> ORGANISM: Artificial Sequence
<220> FEATURE:
<223> OTHER INFORMATION: Randomly generated sequence, created by ExPASy
      WWW server tool

<400> SEQUENCE: 6

Glu Glu Pro Ser Pro Ser Pro Pro Glu Ser Ser Ser Glu Pro Pro
1               5                   10                  15

Pro Pro Pro Pro Gln Pro Pro Glu Pro Pro Gln Gln Ser Glu Gln Pro
            20                  25                  30

Gln Glu Ser Ser Pro Ser Gln Ser Gln Ser Glu Pro Ser Glu Gln Gln
        35                  40                  45

Gln Glu Ser Ser Ser Ser Glu Gln Glu Ser Ser Ser Pro Pro Glu Ser
    50                  55                  60

Gln Glu Glu Pro Gln Ser Glu Gln Pro Ser Pro Pro Glu Pro Gln
65                  70                  75                  80

Pro Gln Ser Gln Ser Ser Gln Pro Pro Ser Glu Ser Pro Ser Gln
            85                  90                  95

Gln Ser Glu Pro Pro Pro Glu Ser Gln Pro Ser Ser Pro Ser
            100                 105                 110

Ser Ser Ser Gln Gln Ser Gln Pro Pro Ser Ser Glu Pro Ser Glu Pro
            115                 120                 125

Ser Pro Ser Ser Pro Gln Ser Ser Pro Ser Pro Ser Pro Gln Gln Ser

-continued

```
            130                 135                 140
Pro Glu Glu Ser Glu Ser Gln Pro Gln Ser Pro Ser Ser Gln Ser Pro
145                 150                 155                 160

Pro Gln Pro Pro Ser Glu Pro Ser Pro Gln Ser Ser Glu Pro Pro
                165                 170                 175

Glu Pro Pro Ser Ser Glu Pro Gln Pro Ser Pro Ser Ser Pro Pro Gln
                180                 185                 190

Pro Glu Ser Pro Ser Ser Ser Ser Pro Pro Ser Pro Pro Ser Pro
                195                 200                 205

Gln Glu Pro Ser Pro Glu Gln Pro Pro Pro Pro Pro Pro Gln Ser
210                 215                 220

Pro Glu Ser Pro Pro Ser Glu Pro Pro Gln Ser Pro Pro Glu Gln Glu
225                 230                 235                 240

Pro Glu Gln Pro Pro Glu Pro Glu Ser Ser Pro Pro Gln Ser Gln Ser
                245                 250                 255

Ser Glu Pro Gln Ser Gln Pro Glu Pro Gln Ser Ser Glu Gln Ser Glu
                260                 265                 270

Glu Ser Glu Ser Gln Gln Glu Pro Pro Ser Ser Pro Glu Pro Pro Ser
                275                 280                 285

Pro Glu Glu Glu Gln Pro Ser Pro Ser Ser Pro Ser Pro Pro Gln Ser
                290                 295                 300

Pro Pro Glu Pro Pro Pro Ser Ser Glu Pro Glu Ser Ser Pro Ser Ser
305                 310                 315                 320

Glu Ser Pro Ser Glu Gln Ser Pro Pro Glu Pro Ser Glu Gln Ser Ser
                325                 330                 335

Gln Ser Pro Ser Pro Ser Pro Gln Gln Glu Gln Ser Pro Pro Ser
                340                 345                 350

Gln Ser Ser Pro Glu Pro Pro Ser Ser Pro Glu Pro Glu Glu Ser Pro
                355                 360                 365

Pro Pro Glu Pro Glu Ser Ser Ser Pro Ser Ser Ser Gln Pro Glu
                370                 375                 380

Glu Gln Pro Ser Ser Pro Ser Pro Pro Ser Pro Ser Ser Ser Gln
385                 390                 395                 400

Ser Ser Pro Ser Ser Gln Ser Pro Ser Ser Pro Glu Glu Ser Pro Ser
                405                 410                 415

Pro Pro Pro Pro Pro Pro Glu Ser Glu Pro Ser Pro Gln Gln Pro Ser
                420                 425                 430

Pro Pro Gln Gln Glu Pro Pro Pro Ser Gln Ser Pro Ser Gln Gln
                435                 440                 445

Ser Pro Pro Pro Pro Ser Ser Pro Pro Pro Ser Glu Gln Pro Pro Gln
450                 455                 460

Glu Pro Gln Pro Pro Ser Gln Ser Ser Gln Pro Pro Glu Pro Ser Ser
465                 470                 475                 480

Gln Ser Glu Pro Ser Pro Pro Gln Ser Pro Pro Gln Pro Glu Ser
                485                 490                 495

Pro Gln Pro Ser Ser Ser Ser Gln Pro Ser Ser Glu Pro Pro Ser Pro
                500                 505                 510

Ser Ser Ser Pro Pro Glu Pro Ser Pro Ser Glu Gln Pro Pro
                515                 520                 525

Ser Pro Ser Gln Glu Glu Pro Ser Glu Pro Ser Gln Ser Glu Ser
                530                 535                 540

Ser Glu Gln Ser Gln Ser Pro Pro Ser Pro Ser Glu Ser Gln Ser
545                 550                 555                 560
```

-continued

Pro Pro Gln Ser Ser Ser Pro Gln Ser Pro Glu Pro Gln Pro Pro
            565                 570                 575
Pro Ser Glu Ser Gln Glu Ser Gln Pro Pro Ser Glu Ser Gln Pro
            580                 585                 590
Ser Pro Glu Glu Ser Ser Pro Ser Gln Ser Glu Gln Pro Ser Gln
            595                 600                 605
Ser Gln Glu Pro Gln Gln Ser Pro Pro Gln Pro Ser Pro Glu Gln Pro
    610                 615                 620
Glu Ser Glu Gln Glu Ser Pro Ser Pro Ser Glu Glu Ser Glu Ser Ser
625                 630                 635                 640
Ser Ser Gln Ser Pro Pro Pro Ser Pro Gln Gly Pro Ser Pro Pro Ser
            645                 650                 655
Glu Ser Gln Ser Ser Pro Ser Ser Pro Pro Gln Pro Ser Ser Ser Gln
            660                 665                 670
Glu Ser Pro Ser Ser Gln Pro Gln Pro Gln Ser Gln Ser Pro Pro Gln
            675                 680                 685
Gln Pro Gln Gln Ser Pro Pro Pro Ser Pro Pro Pro Gln Gln Ser Glu
            690                 695                 700
Glu Gln Glu Gln Glu Ser Glu Pro Gln Glu Pro Gln Pro Gln Ser Ser
705                 710                 715                 720
Pro Glu Ser Pro Ser Ser Glu Ser Glu Ser Glu Ser Ser Pro Glu Gln
            725                 730                 735
Pro Pro Gln Pro Pro Pro Ser Pro Glu Pro Pro Pro Ser Pro Ser
            740                 745                 750
Pro Ser Pro Pro Ser Glu Ser Gln Pro Ser Gln Pro Gln Pro Ser Ser
            755                 760                 765
Ser Ser Glu Ser Pro Glu Glu Ser Pro Gln Pro Pro Pro Glu Glu Ser
            770                 775                 780
Pro Ser Ser Ser Ser Glu Pro Pro Gln Pro Glu Glu Glu Gln
785                 790                 795                 800
Ser Ser Glu Pro Ser Gln Ser Pro Ser Ser Pro Ser Pro Ser
            805                 810                 815
Gln Ser Glu Ser Gln Ser Gln Ser Ser Ser Glu Ser Ser Ser Ser Glu
            820                 825                 830
Ser Glu Ser Gln Ser Pro Glu Pro Glu Glu Pro Glu Pro Pro Ser Gln
            835                 840                 845
Glu Ser Pro Pro Glu Gln Pro Gln Gln Glu Gln Gln Pro Glu Glu Ser
850                 855                 860
Ser Ser Ser Ser Ser Ser Pro Gln Ser Glu Pro Glu Glu Pro Ser
865                 870                 875                 880
Pro Gln Gln Gln Gln Ser Ser Ser Ser Pro Glu Ser Ser Pro Pro
            885                 890                 895
Pro Glu Gln Glu Gln Pro Glu Gln Ser Pro Gln Pro Ser Gln Ser
            900                 905                 910
Pro Gln Ser Ser Ser Glu Ser Glu Pro Gln Pro Glu Gln Gln
            915                 920                 925
Ser Pro Glu Glu Glu Pro Ser Pro Ser Gln Ser Ser Ser Ser Pro
            930                 935                 940
Ser Pro Pro Pro Glu Gln Ser Glu Gln Pro Glu Pro Pro Glu Ser
945                 950                 955                 960
Pro Glu Pro Gln Gln Gln Ser Pro Gln Pro Pro Ser Ser Gln Glu Pro
            965                 970                 975
Glu Glu Pro Glu Pro Gln Ser Pro Pro Glu Ser Glu Pro Pro Glu Glu
            980                 985                 990

Glu Ser Gln Ser Pro Gln Pro Gln
        995                 1000

<210> SEQ ID NO 7
<211> LENGTH: 1000
<212> TYPE: PRT
<213> ORGANISM: Artificial Sequence
<220> FEATURE:
<223> OTHER INFORMATION: Randomly generated sequence, created by ExPASy
      WWW server tool

<400> SEQUENCE: 7

Glu Gln Pro Glu Pro Pro Ser Glu Ser Pro Ser Pro Pro Ser
 1               5                  10                  15

Ser Glu Ser Ser Pro Pro Pro Ser Ser Glu Pro Ser Ser Pro Gln Ser
            20                  25                  30

Gln Ser Pro Glu Glu Glu Pro Ser Gln Ser Gln Pro Ser Glu Ser Ser
        35                  40                  45

Pro Glu Pro Ser Pro Glu Gln Ser Ser Pro Ser Glu Glu Gln Pro
 50                  55                  60

Pro Glu Ser Ser Gln Ser Gln Glu Ser Gln Glu Pro Pro Glu Ser Pro
 65                  70                  75                  80

Pro Gln Gln Pro Ser Pro Pro Ser Gln Glu Ser Ser Glu Gln Glu Ser
                85                  90                  95

Pro Glu Gln Glu Glu Ser Glu Pro Pro Ser Glu Glu Pro Glu Pro Pro
                100                 105                 110

Ser Glu Ser Ser Glu Glu Glu Gln Glu Gln Ser Pro Gln Ser Pro Ser
                115                 120                 125

Ser Glu Pro Glu Pro Glu Gln Ser Gln Glu Ser Pro Ser Ser Ser Glu
                130                 135                 140

Ser Pro Ser Pro Glu Glu Ser Pro Pro Gln Pro Pro Glu Pro Pro Glu
145                 150                 155                 160

Ser Pro Pro Pro Ser Pro Glu Gln Glu Gln Pro Glu Glu Glu Glu Ser
                165                 170                 175

Pro Pro Gln Pro Glu Ser Ser Pro Ser Glu Ser Ser Pro Glu Ser
                180                 185                 190

Pro Gln Glu Pro Pro Ser Ser Pro Pro Glu Ser Ser Glu Glu Glu
                195                 200                 205

Glu Ser Gln Glu Ser Ser Pro Gln Gln Ser Glu Glu Gln Ser Ser Ser
                210                 215                 220

Pro Ser Pro Ser Gln Ser Glu Glu Ser Gln Gln Ser Pro Glu Pro Pro
225                 230                 235                 240

Ser Gln Pro Pro Ser Ser Ser Glu Pro Ser Ser Pro Ser Pro Ser Pro
                245                 250                 255

Glu Pro Glu Pro Gln Gln Pro Gln Gln Gln Ser Gln Pro Glu Ser Pro
                260                 265                 270

Ser Pro Ser Pro Gln Gln Pro Ser Gln Pro Glu Glu Ser Pro Glu
                275                 280                 285

Ser Pro Glu Pro Pro Ser Ser Glu Pro Ser Glu Pro Ser Glu Glu Pro
290                 295                 300

Glu Ser Glu Gln Glu Pro Ser Ser Pro Pro Glu Ser Ser Glu Pro Glu
305                 310                 315                 320

Gln Ser Gln Glu Glu Pro Glu Pro Gln Ser Gln Ser Glu Ser Ser
                325                 330                 335

Pro Glu Glu Ser Pro Glu Ser Ser Gln Gln Gln Glu Pro Glu Pro
                340                 345                 350

-continued

Pro Ser Pro Ser Ser Gln Ser Pro Ser Ser Pro Pro Ser Ser Glu
        355                 360                 365

Pro Pro Ser Pro Pro Glu Pro Ser Pro Ser Ser Glu Ser Pro Glu Gln
370                 375                 380

Gln Gln Glu Glu Gln Pro Ser Glu Glu Pro Gln Ser Ser Ser Glu Glu
385                 390                 395                 400

Gln Ser Gln Ser Ser Glu Pro Pro Glu Pro Ser Pro Gln Ser Ser Pro
            405                 410                 415

Ser Pro Gln Ser Glu Pro Pro Glu Gln Glu Gln Glu Pro Glu Gln
        420                 425                 430

Ser Glu Pro Gln Pro Glu Pro Gln Gln Ser Pro Glu Pro Ser Ser
        435                 440                 445

Ser Pro Glu Gln Gln Pro Glu Pro Pro Pro Gln Ser Ser Ser Pro Pro
450                 455                 460

Ser Gln Glu Glu Ser Ser Pro Pro Glu Ser Ser Pro Glu Glu Ser
465                 470                 475                 480

Ser Glu Glu Pro Ser Ser Glu Gln Gln Glu Pro Ser Ser Pro Gln
        485                 490                 495

Glu Pro Glu Pro Ser Ser Gln Pro Glu Pro Pro Gln Gln Pro Glu
        500                 505                 510

Pro Glu Pro Ser Glu Pro Pro Pro Ser Gln Ser Glu Pro Pro Pro Ser
        515                 520                 525

Pro Pro Glu Glu Gln Gln Ser Ser Pro Pro Glu Pro Glu Pro Pro
        530                 535                 540

Glu Ser Pro Ser Gln Glu Glu Pro Pro Ser Ser Ser Gln Glu Glu Gln
545                 550                 555                 560

Gln Glu Pro Glu Ser Gln Glu Pro Glu Ser Gln Pro Glu Pro Pro
            565                 570                 575

Ser Pro Pro Gln Pro Glu Glu Ser Pro Gln Ser Glu Glu Pro Pro
        580                 585                 590

Ser Pro Ser Gln Pro Ser Pro Ser Glu Glu Gln Ser Glu Pro Ser Gln
        595                 600                 605

Gln Gln Glu Pro Ser Gln Pro Ser Glu Ser Pro Gln Ser Pro Gln Glu
        610                 615                 620

Ser Glu Gln Glu Pro Glu Glu Pro Glu Ser Ser Pro Glu Glu Glu Ser
625                 630                 635                 640

Pro Ser Pro Gln Ser Pro Pro Ser Ser Pro Pro Glu Ser Glu Glu
            645                 650                 655

Gln Pro Glu Glu Gln Pro Pro Gln Gln Ser Pro Glu Pro Pro Pro Ser
        660                 665                 670

Ser Pro Glu Ser Pro Glu Ser Glu Pro Glu Ser Pro Pro Glu Glu
        675                 680                 685

Ser Glu Glu Gln Pro Gln Gln Pro Ser Gln Glu Glu Pro Pro Glu Ser
690                 695                 700

Gln Glu Ser Ser Ser Pro Gln Ser Ser Ser Glu Glu Ser Pro Pro
705                 710                 715                 720

Gln Glu Ser Glu Gln Pro Glu Pro Pro Ser Glu Gln Glu Pro Pro Pro
            725                 730                 735

Glu Gln Gln Pro Glu Gln Ser Glu Gln Ser Ser Glu Gln Gln Pro Pro
        740                 745                 750

Pro Glu Ser Ser Gln Pro Pro Ser Ser Ser Glu Ser Glu Glu Glu
        755                 760                 765

Glu Glu Ser Ser Glu Gln Glu Pro Ser Ser Ser Glu Glu Pro Glu Ser

```
                770                 775                 780
Ser Glu Ser Ser Ser Glu Gln Ser Ser Glu Ser Glu Ser Glu Glu
785                 790                 795                 800

Glu Pro Pro Gln Gln Gln Glu Glu Ser Pro Pro Ser Glu Glu Glu
            805                 810                 815

Gln Gln Gln Pro Pro Pro Glu Pro Glu Ser Glu Ser Pro Gln Ser
            820                 825                 830

Gln Pro Ser Glu Pro Ser Pro Ser Ser Glu Ser Gln Glu Pro Gln
            835                 840                 845

Glu Pro Ser Ser Ser Pro Ser Pro Glu Glu Pro Gln Glu Ser Glu
            850                 855                 860

Glu Ser Pro Pro Glu Ser Pro Glu Ser Ser Gln Pro Ser Pro Ser
865                 870                 875                 880

Gln Glu Pro Pro Glu Ser Glu Ser Gln Pro Gln Glu Ser Ser
            885                 890                 895

Pro Glu Glu Pro Glu Pro Pro Pro Glu Pro Glu Glu Pro Pro Pro
                900                 905                 910

Pro Pro Ser Pro Glu Pro Glu Glu Glu Gln Pro Gln Pro Ser Gln
            915                 920                 925

Gln Ser Ser Ser Gln Glu Glu Glu Ser Ser Glu Glu Pro Ser
            930                 935                 940

Ser Glu Pro Ser Ser Glu Glu Ser Ser Ser Ser Ser Pro Ser
945                 950                 955                 960

Ser Glu Gln Gln Ser Glu Ser Gln Glu Glu Pro Glu Glu Ser Glu
            965                 970                 975

Glu Pro Pro Pro Ser Ser Glu Ser Pro Glu Glu Glu Glu Pro Ser
            980                 985                 990

Glu Pro Pro Glu Ser Ser Glu Pro
            995                 1000

<210> SEQ ID NO 8
<211> LENGTH: 1000
<212> TYPE: PRT
<213> ORGANISM: Artificial Sequence
<220> FEATURE:
<223> OTHER INFORMATION: Randomly generated sequence, created by ExPASy
      WWW server tool

<400> SEQUENCE: 8

Ser Pro Glu Gln Pro Glu Pro Gln Pro Glu Pro Glu Gln Glu Ser Glu
1               5                   10                  15

Pro Glu Pro Ser Glu Pro Pro Pro Ser Gln Glu Gln Glu Ser Glu Glu
                20                  25                  30

Glu Glu Gln Ser Glu Gln Pro Glu Glu Glu Ser Ser Glu Pro Ser Pro
            35                  40                  45

Glu Ser Ser Pro Ser Pro Gln Glu Pro Ser Pro Gln Gln Glu Pro Pro
        50                  55                  60

Ser Glu Pro Gln Gln Glu Ser Glu Pro Ser Gln Ser Pro Ser Ser Glu
65              70                  75                  80

Ser Glu Gln Ser Glu Glu Glu Glu Pro Gln Glu Ser Glu Ser Glu
                85                  90                  95

Glu Ser Pro Glu Ser Ser Pro Ser Ser Glu Pro Ser Glu Glu Glu Ser
                100                 105                 110

Glu Gln Ser Glu Ser Ser Glu Glu Glu Glu Pro Pro Ser Pro Pro Ser
            115                 120                 125

Pro Glu Glu Glu Ser Pro Glu Ser Gln Glu Gln Gln Glu Pro Glu Gln
```

130                 135                 140
Gln Ser Glu Pro Glu Glu Ser Ser Ser Pro Ser Pro Glu Pro
145                 150                 155                 160

Ser Glu Glu Pro Pro Glu Ser Glu Pro Ser Glu Glu Ser Pro Pro
                165                 170                 175

Ser Glu Gln Ser Glu Pro Glu Pro Pro Glu Ser Ser Glu Pro Pro
                180                 185                 190

Gln Gln Glu Gln Glu Ser Glu Ser Ser Ser Pro Pro Glu Ser Glu
                195                 200                 205

Pro Pro Glu Gln Ser Ser Glu Pro Glu Glu Gln Gln Ser Glu Glu
210                 215                 220

Glu Glu Ser Pro Glu Glu Ser Ser Glu Glu Ser Ser Pro Glu Gln
225                 230                 235                 240

Ser Ser Ser Ser Ser Glu Glu Glu Ser Glu Glu Pro Glu Ser Pro
                245                 250                 255

Glu Glu Glu Glu Pro Ser Gln Pro Glu Gln Pro Gln Gln Ser Pro Pro
                260                 265                 270

Gln Glu Ser Pro Pro Glu Glu Ser Gln Glu Pro Ser Glu Ser Ser
                275                 280                 285

Ser Ser Glu Gln Ser Ser Glu Ser Gln Ser Gln Ser Pro Ser Ser Ser
                290                 295                 300

Ser Glu Pro Gln Glu Pro Gln Pro Pro Glu Gln Pro Ser Ser Gln Glu Glu
305                 310                 315                 320

Pro Glu Pro Pro Glu Gln Glu Pro Glu Pro Ser Gln Pro Ser Glu Glu
                325                 330                 335

Ser Ser Pro Ser Ser Glu Pro Glu Glu Ser Pro Pro Glu Glu Glu Ser
                340                 345                 350

Glu Ser Ser Glu Ser Glu Glu Ser Glu Glu Glu Glu Glu Glu Glu
                355                 360                 365

Ser Pro Ser Pro Ser Pro Gln Glu Pro Ser Ser Gln Pro Pro Ser Glu
                370                 375                 380

Glu Pro Ser Glu Glu Pro Ser Pro Glu Glu Gln Glu Ser Glu Glu Glu
385                 390                 395                 400

Glu Ser Pro Ser Ser Ser Glu Gln Glu Glu Pro Ser Gln Ser Glu Gln
                405                 410                 415

Gln Ser Pro Pro Ser Ser Pro Pro Glu Ser Glu Gln Ser Glu Glu
                420                 425                 430

Glu Pro Glu Glu Glu Glu Gln Pro Pro Glu Pro Ser Gln Ser Pro Glu
                435                 440                 445

Glu Ser Glu Ser Glu Glu Gln Gln Ser Ser Glu Ser Glu Pro Pro Gln
                450                 455                 460

Ser Pro Pro Glu Glu Pro Glu Pro Glu Gln Gln Gln Ser Ser Ser Glu
465                 470                 475                 480

Glu Ser Glu Gln Glu Ser Glu Pro Ser Gln Glu Ser Glu Ser Glu
                485                 490                 495

Ser Glu Glu Ser Glu Glu Ser Ser Pro Ser Ser Ser Pro Gln Pro Glu
                500                 505                 510

Glu Pro Glu Ser Glu Glu Glu Gln Pro Ser Pro Ser Pro Glu Ser Gln
                515                 520                 525

Glu Pro Glu Glu Ser Glu Pro Ser Glu Glu Pro Ser Gln Ser Pro Glu
                530                 535                 540

Glu Glu Glu Glu Glu Pro Glu Pro Glu Pro Gln Gln Ser Glu Glu Glu
545                 550                 555                 560

```
Gln Pro Gln Glu Ser Ser Gln Glu Glu Glu Pro Pro Glu Ser
                565                 570                 575

Glu Gln Gln Pro Ser Ser Gln Glu Glu Ser Glu Glu Pro Gln Gln
                580                 585                 590

Glu Glu Pro Ser Glu Ser Gln Pro Gln Pro Glu Ser Ser Pro Pro
                595                 600                 605

Ser Pro Pro Pro Pro Glu Glu Pro Ser Gln Glu Glu Ser Glu Gln Glu
610                 615                 620

Pro Glu Glu Glu Gln Ser Pro Pro Glu Pro Glu Gln Glu Pro Ser
625                 630                 635                 640

Pro Ser Glu Ser Glu Glu Ser Pro Pro Glu Ser Glu Ser Ser Glu Glu
                645                 650                 655

Gln Gln Glu Glu Ser Glu Pro Glu Ser Glu Glu Pro Pro Gln Gln
                660                 665                 670

Ser Glu Glu Gln Gln Ser Gln Pro Glu Glu Glu Glu Glu Gln Ser
                675                 680                 685

Glu Glu Pro Ser Ser Ser Pro Glu Pro Pro Gln Gln Glu Pro Ser
690                 695                 700

Ser Pro Ser Glu Gln Pro Pro Gln Pro Glu Glu Pro Glu Pro Glu Glu
705                 710                 715                 720

Glu Ser Glu Glu Pro Ser Pro Glu Gln Pro Ser Glu Ser Ser Glu Pro
                725                 730                 735

Pro Glu Ser Pro Glu Glu Pro Ser Pro Pro Pro Ser Ser Glu Glu
                740                 745                 750

Ser Glu Ser Glu Ser Glu Gln Pro Glu Glu Pro Ser Glu Glu
                755                 760                 765

Pro Pro Ser Ser Pro Ser Glu Ser Ser Glu Glu Pro Glu Glu Glu Pro
770                 775                 780

Glu Glu Glu Gln Pro Ser Glu Pro Gln Pro Ser Glu Gln Pro Ser
785                 790                 795                 800

Pro Pro Glu Glu Pro Gln Glu Glu Ser Glu Glu Pro Pro Ser Glu
                805                 810                 815

Glu Pro Ser Gln Ser Glu Ser Pro Glu Pro Glu Pro Ser Pro Ser Ser
                820                 825                 830

Pro Pro Pro Gln Glu Pro Glu Gln Pro Ser Ser Ser Glu Gln Ser Pro
                835                 840                 845

Pro Glu Pro Ser Glu Gln Ser Pro Pro Ser Gln Glu Glu Pro Glu Glu
                850                 855                 860

Glu Pro Ser Gln Ser Glu Gln Glu Ser Glu Ser Glu Pro Gln Glu Glu
865                 870                 875                 880

Pro Pro Gln Pro Ser Pro Glu Pro Ser Pro Gln Glu Pro Ser Glu Pro
                885                 890                 895

Glu Pro Glu Glu Pro Pro Glu Glu Glu Pro Pro Gln Pro Pro Ser
                900                 905                 910

Ser Glu Pro Glu Glu Gln Glu Ser Ser Ser Glu Pro Gln Gln Pro
                915                 920                 925

Gln Pro Ser Ser Ser Pro Glu Glu Glu Pro Glu Glu Ser Pro Glu
                930                 935                 940

Pro Ser Pro Gln Pro Glu Pro Glu Ser Glu Pro Glu Glu Gln Ser
945                 950                 955                 960

Pro Ser Glu Gln Glu Pro Glu Glu Glu Ser Gln Glu Pro Ser Ser
                965                 970                 975

Pro Gln Glu Pro Glu Glu Glu Gln Ser Glu Ser Glu Ser Pro Ser Pro
                980                 985                 990
```

```
Glu Pro Glu Pro Glu Pro Glu Glu
        995                 1000

<210> SEQ ID NO 9
<211> LENGTH: 1000
<212> TYPE: PRT
<213> ORGANISM: Artificial Sequence
<220> FEATURE:
<223> OTHER INFORMATION: Randomly generated sequence, created by ExPASy
      WWW server tool

<400> SEQUENCE: 9

Pro Gln Glu Pro Ser Glu Ser Glu Ser Pro Gln Pro Ser Glu Ser Glu
 1               5                   10                  15

Glu Glu Gln Pro Glu Gln Glu Ser Pro Gln Ser Ser Glu Glu Ser Pro
            20                  25                  30

Ser Gln Glu Gln Glu Glu Gln Glu Glu Pro Ser Glu Glu Glu Glu Pro
        35                  40                  45

Glu Glu Ser Pro Glu Pro Ser Glu Glu Gln Glu Pro Pro Pro Pro Glu
    50                  55                  60

Glu Pro Glu Glu Ser Pro Pro Glu Pro Glu Glu Glu Glu Glu Glu Glu
65                  70                  75                  80

Ser Glu Ser Pro Glu Pro Gln Ser Glu Ser Glu Glu Glu Ser Pro Glu
                85                  90                  95

Glu Pro Pro Gln Ser Glu Glu Pro Gln Ser Pro Gln Pro Glu Pro Ser
            100                 105                 110

Pro Glu Glu Glu Pro Pro Glu Pro Glu Gln Pro Glu Pro Ser Pro Gln
        115                 120                 125

Ser Glu Glu Pro Gln Glu Pro Gln Glu Glu Glu Glu Pro Glu Glu Pro
    130                 135                 140

Glu Pro Glu Glu Glu Glu Pro Pro Glu Glu Glu Ser Glu Glu Ser Ser
145                 150                 155                 160

Gln Glu Ser Pro Ser Glu Glu Pro Ser Ser Ser Pro Glu Ser Glu Glu
                165                 170                 175

Glu Glu Glu Pro Pro Gln Glu Pro Ser Ser Glu Ser Glu Pro Glu Glu
            180                 185                 190

Glu Ser Pro Gln Glu Glu Glu Glu Ser Glu Gln Ser Gln Glu Ser Glu
        195                 200                 205

Glu Gln Gln Glu Glu Ser Pro Ser Pro Glu Ser Glu Ser Ser Pro Pro
    210                 215                 220

Glu Ser Gln Glu Ser Glu Ser Glu Glu Glu Gln Glu Ser Glu Glu Ser
225                 230                 235                 240

Ser Ser Gln Pro Ser Glu Pro Glu Glu Glu Gln Glu Glu Glu Glu Glu
                245                 250                 255

Ser Pro Glu Pro Glu Gln Glu Pro Glu Pro Glu Glu Ser Ser Ser Ser
            260                 265                 270

Ser Glu Ser Gln Ser Glu Ser Ser Glu Gln Glu Ser Ser Gln Glu Ser
        275                 280                 285

Glu Gln Ser Pro Pro Glu Glu Glu Ser Glu Ser Ser Gln Glu Ser Glu
    290                 295                 300

Glu Ser Pro Glu Ser Glu Gln Glu Gln Pro Pro Glu Glu Ser Glu Glu
305                 310                 315                 320

Glu Gln Pro Pro Glu Glu Pro Glu Glu Gln Pro Gln Glu Pro Gln Ser
                325                 330                 335

Ser Pro Gln Glu Ser Pro Ser Ser Pro Glu Ser Glu Ser Pro Pro Ser
            340                 345                 350
```

Glu Pro Pro Pro Ser Glu Glu Glu Pro Pro Glu Glu Pro
        355                 360                 365

Pro Glu Ser Glu Glu Pro Glu Glu Glu Glu Glu Glu Glu
    370                 375                 380

Pro Glu Glu Glu Glu Glu Pro Ser Glu Ser Pro Glu Ser
385                 390                 395                 400

Ser Glu Pro Pro Pro Ser Ser Glu Pro Glu Pro Ser Glu Pro
                405                 410                 415

Glu Ser Pro Glu Glu Glu Ser Ser Pro Glu Glu Ser Gln Ser Pro Glu
            420                 425                 430

Glu Glu Glu Glu Glu Ser Glu Glu Pro Gln Pro Glu Ser Ser Glu
            435                 440                 445

Pro Glu Glu Pro Glu Glu Gln Glu Gln Gln Glu Glu Gln Glu Glu Pro
    450                 455                 460

Pro Ser Pro Gln Pro Pro Glu Glu Gln Pro Gln Gln Gln Glu Gln Glu
465                 470                 475                 480

Gln Ser Glu Pro Ser Glu Gln Glu Gln Pro Ser Ser Ser Pro Glu
            485                 490                 495

Ser Glu Glu Glu Ser Glu Pro Glu Glu Pro Glu Pro Glu Gln Glu Ser
            500                 505                 510

Pro Pro Glu Ser Glu Glu Glu Ser Glu Gln Pro Pro Glu Ser Pro Ser
    515                 520                 525

Ser Glu Pro Ser Ser Pro Glu Glu Ser Gln Glu Ser Ser Ser Pro Glu
            530                 535                 540

Ser Pro Glu Ser Pro Ser Pro Pro Glu Ser Ser Gln Pro Glu Glu Glu
545                 550                 555                 560

Pro Gln Gln Glu Pro Glu Pro Ser Ser Pro Gln Pro Gln Glu Gln Pro
                565                 570                 575

Glu Glu Glu Glu Ser Pro Pro Pro Ser Ser Pro Glu Gln Pro Glu Glu
            580                 585                 590

Pro Glu Glu Glu Ser Ser Ser Gln Ser Ser Gln Glu Glu Gln Pro Ser
            595                 600                 605

Glu Glu Glu Ser Glu Glu Glu Ser Gln Glu Glu Pro Ser Glu Ser
    610                 615                 620

Ser Glu Glu Pro Glu Glu Glu Glu Glu Pro Pro Glu Ser Gln Ser
625                 630                 635                 640

Glu Glu Gln Ser Gln Glu Glu Gln Pro Glu Ser Pro Gln Glu Glu
            645                 650                 655

Gln Ser Glu Ser Pro Pro Gln Pro Pro Glu Glu Pro Glu Glu Gln Ser
            660                 665                 670

Ser Gln Glu Glu Ser Glu Glu Gln Pro Ser Glu Gln Ser Ser Glu
    675                 680                 685

Glu Pro Ser Ser Glu Ser Glu Glu Ser Glu Pro Gln Glu Ser Glu Glu
    690                 695                 700

Glu Glu Pro Pro Ser Glu Pro Glu Ser Glu Gln Gln Ser Glu Glu Pro
705                 710                 715                 720

Pro Gln Ser Gln Glu Ser Pro Gln Pro Ser Ser Glu Pro Glu
                725                 730                 735

Glu Glu Glu Gln Pro Ser Glu Glu Pro Ser Gln Glu Gln Glu Pro
            740                 745                 750

Glu Glu Glu Glu Glu Glu Glu Ser Ser Glu Pro Pro Glu Glu Glu
            755                 760                 765

Pro Gln Glu Glu Pro Glu Glu Pro Pro Glu Glu Glu Glu Glu Glu

-continued

```
            770                 775                 780
Gln Ser Glu Glu Glu Glu Pro Glu Pro Ser Glu Gln Glu Glu
785                 790                 795                 800

Glu Pro Pro Glu Glu Pro Glu Ser Glu Ser Glu Ser Pro Ser Pro
                805                 810                 815

Glu Pro Ser Ser Ser Glu Gln Ser Pro Ser Gln Glu Gln Ser
                820                 825                 830

Ser Glu Glu Ser Gln Pro Glu Glu Pro Glu Gln Ser Glu Glu
                835                 840                 845

Ser Ser Gln Pro Pro Glu Pro Glu Pro Pro Pro Glu Ser Glu
                850                 855                 860

Ser Ser Ser Ser Glu Ser Glu Ser Glu Gln Ser Glu Ser Gln Glu Glu
865                 870                 875                 880

Pro Glu Pro Ser Glu Glu Pro Ser Glu Gln Ser Ser Glu Ser Glu
                885                 890                 895

Pro Glu Ser Glu Glu Glu Glu Glu Ser Pro Glu Glu Pro Glu Gln Glu
                900                 905                 910

Gln Pro Ser Glu Pro Glu Glu Pro Glu Pro Ser Glu Gln Glu Glu
                915                 920                 925

Glu Ser Glu Ser Pro Pro Pro Pro Ser Glu Glu Ser Pro Pro Gln
930                 935                 940

Ser Ser Glu Pro Ser Pro Glu Glu Gln Pro Gln Ser Glu Pro Glu
945                 950                 955                 960

Pro Glu Pro Ser Ser Pro Pro Glu Pro Pro Glu Glu Glu Ser Ser
                965                 970                 975

Glu Pro Glu Ser Glu Glu Glu Ser Glu Ser Ser Glu Gln Glu Pro Glu
                980                 985                 990

Glu Pro Pro Glu Ser Glu Ser Glu
                995                 1000

<210> SEQ ID NO 10
<211> LENGTH: 1000
<212> TYPE: PRT
<213> ORGANISM: Artificial Sequence
<220> FEATURE:
<223> OTHER INFORMATION: Randomly generated sequence, created by ExPASy
      WWW server tool

<400> SEQUENCE: 10

Glu Glu Glu Glu Ser Ser Pro Pro Glu Glu Glu Ser Ser Pro Glu
1                   5                   10                  15

Pro Glu Glu Pro Glu Pro Glu Pro Ser Pro Gln Glu Glu Glu Glu
                20                  25                  30

Glu Pro Ser Pro Gln Glu Gln Pro Gln Gln Glu Glu Ser Ser Gln
                35                  40                  45

Glu Glu Glu Gln Glu Pro Glu Glu Glu Glu Glu Ser Ser Ser Pro
                50                  55                  60

Gln Glu Glu Pro Pro Gln Pro Glu Glu Pro Glu Pro Glu Glu Glu
65                  70                  75                  80

Glu Glu Ser Ser Ser Glu Glu Glu Pro Glu Glu Gln Glu Gln Pro
                85                  90                  95

Glu Pro Glu Glu Glu Pro Ser Pro Glu Ser Ser Glu Ser Glu Ser
                100                 105                 110

Ser Ser Glu Glu Glu Glu Glu Gln Pro Ser Gln Pro Glu Ser Ser Pro
                115                 120                 125

Ser Glu Glu Glu Gln Pro Gln Glu Pro Glu Glu Pro Glu Pro Glu Glu
```

-continued

```
            130                 135                 140
Glu Ser Pro Ser Pro Glu Gln Glu Glu Ser Glu Ser Glu
145                 150                 155                 160

Glu Glu Gln Glu Gln Ser Glu Pro Glu Ser Glu Glu Glu
                165                 170                 175

Pro Ser Ser Pro Gln Ser Glu Glu Glu Pro Gln Glu Pro
            180                 185                 190

Glu Glu Gln Glu Glu Pro Pro Glu Glu Glu Gln Glu Pro
            195                 200                 205

Glu Ser Glu Ser Pro Glu Glu Gln Glu Glu Gln Pro Ser Pro
210                 215                 220

Glu Glu Glu Ser Glu Glu Glu Pro Glu Glu Glu Glu Gln
225                 230                 235                 240

Glu Glu Ser Glu Glu Glu Ser Gln Ser Pro Ser Glu Pro Glu
                245                 250                 255

Pro Glu Glu Ser Ser Pro Glu Ser Glu Glu Pro Pro Glu Glu Glu
            260                 265                 270

Ser Ser Glu Glu Ser Glu Glu Ser Gln Glu Glu Ser Pro Ser Pro
275                 280                 285

Glu Glu Glu Glu Glu Ser Ser Glu Ser Glu Gln Pro Pro Glu Ser Pro
290                 295                 300

Ser Glu Ser Gln Glu Ser Pro Ser Gln Ser Glu Glu Ser Gln Glu
305                 310                 315                 320

Glu Pro Pro Glu Glu Glu Ser Ser Pro Glu Glu Pro Pro Pro Ser
                325                 330                 335

Pro Ser Glu Ser Glu Pro Pro Glu Glu Glu Glu Pro Ser Glu Ser
            340                 345                 350

Glu Glu Glu Glu Pro Pro Pro Glu Glu Glu Ser Ser Ser Glu Glu
            355                 360                 365

Gln Glu Ser Glu Glu Pro Glu Ser Glu Glu Ser Pro Glu Glu Gln
            370                 375                 380

Ser Glu Glu Glu Glu Glu Ser Gln Glu Ser Ser Pro Glu Pro Pro Glu
385                 390                 395                 400

Glu Ser Pro Ser Glu Gln Pro Glu Pro Ser Pro Glu Pro Glu Ser
                405                 410                 415

Glu Ser Ser Glu Pro Glu Glu Glu Glu Glu Glu Glu Glu Pro Pro
            420                 425                 430

Ser Ser Glu Glu Glu Glu Ser Glu Glu Pro Gln Pro Glu Glu Glu
            435                 440                 445

Gln Glu Glu Pro Gln Glu Glu Glu Glu Ser Pro Ser Glu Glu Ser Pro
450                 455                 460

Glu Glu Pro Glu Glu Ser Glu Pro Glu Glu Ser Glu Glu Glu Glu
465                 470                 475                 480

Pro Glu Gln Gln Pro Glu Glu Glu Pro Glu Glu Glu Glu Gln Glu
                485                 490                 495

Ser Ser Glu Pro Ser Ser Pro Pro Ser Glu Glu Gln Ser Glu Glu Pro
            500                 505                 510

Glu Glu Gln Glu Glu Pro Pro Glu Pro Ser Gln Pro Glu Pro Gln Gln
            515                 520                 525

Glu Ser Glu Ser Ser Ser Pro Ser Ser Gln Pro Glu Ser Gln Glu
            530                 535                 540

Ser Glu Glu Glu Glu Glu Glu Glu Glu Ser Glu Glu Glu Ser Glu Pro
545                 550                 555                 560
```

```
Ser Gln Glu Pro Glu Glu Gln Pro Glu Glu Glu Glu Glu
            565             570             575

Glu Glu Pro Glu Glu Glu Glu Gln Ser Glu Pro Glu Ser Ser
            580             585             590

Glu Gln Gln Glu Pro Pro Gln Ser Ser Gln Pro Glu Glu Ser Glu
            595             600             605

Gln Glu Gln Glu Glu Pro Gln Ser Pro Glu Glu Ser Pro Pro
            610             615             620

Glu Glu Glu Glu Pro Gln Glu Pro Pro Glu Pro Glu Glu Glu
625             630             635             640

Pro Ser Glu Gln Pro Pro Ser Ser Pro Glu Glu Gln Ser Glu Gln
            645             650             655

Pro Glu Gln Ser Glu Pro Gln Ser Glu Ser Pro Ser Gln Pro Glu Ser
            660             665             670

Ser Glu Gln Pro Glu Glu Gln Pro Glu Pro Pro Ser Pro Gln Ser Ser
            675             680             685

Glu Glu Ser Glu Glu Pro Glu Glu Glu Glu Gln Ser Glu Glu Pro Ser
            690             695             700

Pro Ser Gln Ser Glu Ser Ser Ser Pro Glu Glu Ser Glu Pro Pro
705             710             715             720

Glu Glu Glu Glu Glu Glu Glu Pro Glu Glu Pro Glu Gln Glu Glu
            725             730             735

Glu Gln Ser Glu Pro Gln Glu Gln Pro Ser Glu Ser Ser Glu
            740             745             750

Pro Glu Glu Glu Ser Ser Pro Ser Ser Gln Ser Glu Gln Ser Ser
            755             760             765

Ser Glu Glu Glu Ser Glu Ser Glu Gln Ser Ser Pro Pro Glu Glu
770             775             780

Glu Ser Pro Glu Glu Glu Pro Glu Glu Glu Pro Glu Glu Ser
785             790             795             800

Pro Glu Glu Glu Ser Glu Glu Ser Pro Glu Ser Glu Ser Glu Glu
            805             810             815

Ser Ser Glu Glu Gln Glu Glu Ser Ser Pro Glu Glu Glu Pro Ser Glu
            820             825             830

Gln Glu Glu Pro Pro Glu Gln Glu Pro Glu Ser Pro Pro Glu Gln Glu
            835             840             845

Glu Glu Glu Glu Gln Ser Glu Pro Gln Glu Glu Pro Pro Glu Ser
850             855             860

Ser Glu Pro Glu Glu Glu Ser Pro Pro Glu Glu Pro Gln Ser Glu Glu
865             870             875             880

Glu Glu Glu Glu Pro Gln Pro Glu Ser Glu Ser Glu Pro Glu Glu Pro
            885             890             895

Ser Pro Glu Pro Glu Ser Glu Glu Ser Glu Glu Pro Glu Ser Glu
            900             905             910

Ser Ser Ser Pro Pro Glu Ser Ser Ser Glu Glu Glu Glu Glu Pro
            915             920             925

Glu Glu Gln Ser Glu Glu Glu Glu Ser Gln Glu Glu Glu Glu Gln
            930             935             940

Glu Glu Glu Pro Ser Gln Glu Glu Glu Glu Pro Glu Glu Gln Gln Pro
945             950             955             960

Pro Ser Glu Glu Glu Glu Gln Pro Glu Gln Ser Glu Glu Pro Glu Pro
            965             970             975

Ser Glu Pro Ser Glu Glu Glu Pro Glu Pro Glu Glu Ser Pro Pro Glu
            980             985             990
```

```
Ser Gln Pro Pro Ser Glu Glu Pro
        995                 1000

<210> SEQ ID NO 11
<211> LENGTH: 1000
<212> TYPE: PRT
<213> ORGANISM: Artificial Sequence
<220> FEATURE:
<223> OTHER INFORMATION: Randomly generated sequence, created by ExPASy
      WWW server tool

<400> SEQUENCE: 11

Gly Gln Gln Gly Ser Ser Pro Pro Ser Pro Ser Gln Gly Gly Gln Pro
 1               5                  10                  15

Pro Ser Ser Gln Pro Ser Gln Gln Ser Ser Ser Pro Pro Pro Ser
            20                  25                  30

Pro Pro Pro Ser Ser Pro Pro Ser Gln Pro Pro Ser Pro Ser Ser
            35                  40                  45

Gly Ser Gly Ser Ser Ser Pro Ser Gln Gly Ser Pro Pro Ser Pro Pro
 50                  55                  60

Ser Gln Gly Pro Pro Gln Pro Pro Gln Ser Pro Gly Ser Gln Gly Pro
 65                  70                  75                  80

Pro Pro Pro Pro Gly Pro Gly Ser Gly Pro Pro Ser Ser Ser Pro
            85                  90                  95

Gln Pro Ser Gln Pro Pro Pro Ser Gln Pro Gln Gln Ser Pro Gln
            100                 105                 110

Pro Ser Pro Gly Pro Gly Ser Pro Ser Gln Gln Pro Ser Gly Ser
            115                 120                 125

Gln Gln Ser Pro Gly Gln Gly Pro Gln Pro Gln Gly Pro Ser Gly Ser
130                 135                 140

Pro Gln Gly Gln Gly Ser Pro Gly Ser Ser Gly Pro Gln Pro Ser
145                 150                 155                 160

Ser Gln Gly Ser Pro Pro Gly Pro Pro Pro Gly Pro Ser Pro Ser Gly
                    165                 170                 175

Gly Pro Gln Ser Ser Pro Gly Ser Pro Pro Ser Pro Gln Gly Ser Gln
                    180                 185                 190

Pro Gln Ser Pro Gly Pro Ser Ser Pro Ser Ser Pro Gln Pro Pro
                    195                 200                 205

Ser Gly Pro Pro Ser Ser Gly Gly Gln Ser Gln Gly Gln Ser Pro
210                 215                 220

Ser Gln Gly Pro Pro Pro Gly Ser Pro Gln Pro Pro Gly Gly Ser Gly
225                 230                 235                 240

Pro Ser Pro Ser Ser Ser Pro Pro Pro Ser Pro Pro Pro Gln Ser
                    245                 250                 255

Ser Ser Ser Gly Ser Gln Gln Ser Ser Ser Ser Gly Ser Pro Pro
                    260                 265                 270

Ser Ser Ser Gln Gly Pro Pro Gln Ser Ser Gln Pro Gln Ser Gln
                    275                 280                 285

Ser Ser Pro Ser Gln Pro Pro Ser Gly Ser Pro Gly Ser Ser Ser Ser
                    290                 295                 300

Pro Ser Pro Ser Pro Ser Gly Pro Ser Gly Ser Pro Gly Pro Pro
305                 310                 315                 320

Ser Ser Pro Ser Gly Ser Pro Pro Gly Gly Pro Pro Gln Ser Gly
                    325                 330                 335

Gly Pro Gly Pro Ser Ser Gly Gln Gln Pro Pro Gly Pro Gln Pro Gly
                    340                 345                 350
```

```
Ser Pro Pro Gly Gln Pro Gln Pro Gly Ser Ser Ser Gln Gly Pro Gln
        355                 360                 365
Gln Gly Pro Pro Pro Gly Ser Pro Gln Gly Pro Ser Gln Pro Gly Pro
    370                 375                 380
Gln Ser Pro Pro Ser Ser Gly Gly Ser Ser Gln Pro Gln Ser Pro
385                 390                 395                 400
Ser Ser Gly Pro Gly Gln Pro Ser Pro Ser Pro Gly Ser Pro Gly
            405                 410                 415
Gly Pro Gly Gln Pro Pro Ser Gln Pro Ser Pro Ser Ser Ser Ser
            420                 425                 430
Gln Ser Gly Gln Ser Ser Gln Pro Ser Gly Pro Pro Ser Gly Gln Ser
    435                 440                 445
Gln Pro Gly Gln Pro Pro Gln Pro Ser Pro Ser Pro Pro Pro
    450                 455                 460
Ser Pro Pro Ser Gln Ser Gly Ser Gly Ser Pro Gly Pro Ser Gly
465                 470                 475                 480
Pro Gln Pro Ser Ser Gln Pro Ser Gln Pro Gly Gln Gly Pro
            485                 490                 495
Ser Ser Ser Pro Pro Gly Gln Ser Gly Pro Ser Ser Pro Ser Ser
            500                 505                 510
Gln Pro Pro Ser Gln Ser Pro Pro Gln Ser Gly Gln Ser Pro Ser
    515                 520                 525
Ser Ser Pro Pro Gln Ser Ser Pro Ser Ser Gly Gln Gln Pro Ser Pro
    530                 535                 540
Gly Pro Pro Ser Ser Ser Pro Gln Pro Ser Ser Ser Gln Gly Ser
545                 550                 555                 560
Pro Pro Pro Gln Pro Gly Gln Ser Pro Pro Ser Gln Pro Ser
            565                 570                 575
Gln Pro Gly Gly Ser Ser Gln Pro Ser Ser Pro Pro Pro Gly Pro
    580                 585                 590
Gln Gly Pro Gln Pro Pro Ser Pro Gln Pro Ser Gly Pro Gly Ser
    595                 600                 605
Gln Pro Gln Gly Gly Ser Pro Ser Ser Gln Gly Gly Gln Pro Ser Ser
    610                 615                 620
Ser Pro Pro Gln Ser Ser Ser Gly Pro Ser Gly Pro Gly Ser Ser Pro
625                 630                 635                 640
Ser Gln Ser Pro Ser Gly Gln Gly Pro Ser Ser Gln Pro Ser Pro Ser
            645                 650                 655
Gly Ser Gly Gln Pro Gln Gly Pro Pro Ser Pro Ser Gly Gln Pro Pro
            660                 665                 670
Ser Pro Pro Ser Gly Ser Pro Ser Pro Gln Pro Gly Ser Pro Gly
    675                 680                 685
Gln Pro Gln Pro Ser Pro Ser Gln Ser Pro Gly Gly Pro Gly Gly
    690                 695                 700
Pro Gln Gly Pro Pro Ser Ser Pro Gly Ser Ser Gly Ser Ser Gly Ser
705                 710                 715                 720
Ser Gln Pro Pro Pro Pro Ser Gln Ser Ser Gly Gln Ser
            725                 730                 735
Pro Gln Pro Gln Gly Gln Gly Gln Pro Gly Ser Pro Gly Gln Ser
    740                 745                 750
Gly Gln Gln Ser Gln Ser Pro Gly Gly Pro Ser Pro Gln Gln Pro Pro
    755                 760                 765
Pro Pro Pro Pro Pro Pro Pro Gly Ser Ser Pro Gln Ser Ser Pro Gln
```

|     |     |     |     |     |     |     |     |     |     |     |     |
| --- | --- | --- | --- | --- | --- | --- | --- | --- | --- | --- | --- |
|     |     | 770 |     |     | 775 |     |     | 780 |     |     |     |
| Pro | Ser | Pro | Ser | Gln | Ser | Gln | Pro | Gln | Ser | Gly | Ser | Gln | Ser | Gln |
| 785 |     |     |     | 790 |     |     |     | 795 |     |     |     | 800 |

```
                770             775             780
Pro Ser Pro Ser Gln Ser Gln Pro Gln Ser Gly Ser Gln Ser Gln
785             790             795             800
Gln Gln Ser Gln Ser Ser Ser Pro Ser Pro Gln Ser Gln Gly Gly
            805             810             815
Pro Gln Ser Ser Gly Ser Ser Pro Ser Ser Gly Pro Gln Ser Pro Ser
            820             825             830
Pro Gly Gly Pro Pro Pro Ser Gln Ser Ser Gly Gln Pro Ser Pro
            835             840             845
Pro Ser Pro Pro Gly Pro Ser Gly Ser Ser Ser Ser Ser Gly Ser
            850             855             860
Gly Ser Gly Pro Gln Pro Ser Pro Pro Gln Ser Pro Ser Gln Gln
865             870             875             880
Ser Gly Ser Ser Gln Ser Ser Pro Ser Gln Ser Gln Pro Gln Pro Pro
                885             890             895
Pro Pro Gly Ser Gly Gln Pro Pro Pro Ser Gly Gly Pro Gln Gln Pro
            900             905             910
Pro Ser Pro Gln Gln Gly Ser Gln Ser Ser Ser Gln Pro Pro Pro
            915             920             925
Gln Ser Ser Ser Gly Gly Pro Gly Gln Ser Gly Ser Pro Gly
            930             935             940
Pro Ser Pro Pro Gln Gln Ser Gly Gly Ser Pro Pro Ser Gly Gly
945             950             955             960
Gly Ser Gly Pro Gly Ser Pro Pro Ser Gly Gln Gly Ser Pro Ser Gln
            965             970             975
Ser Ser Gly Pro Ser Gly Gly Pro Gly Gly Ser Pro Pro Pro Ser
            980             985             990
Ser Pro Ser Pro Ser Gln Ser Ser
            995             1000
```

<210> SEQ ID NO 12
<211> LENGTH: 3000
<212> TYPE: DNA
<213> ORGANISM: Artificial Sequence
<220> FEATURE:
<223> OTHER INFORMATION: Sequence is produced using the reverse
translation tool located at:
www.vivo.colostate.edu/molkit/rtranslate/index.html.

<400> SEQUENCE: 12

```
tctcaatctc ctaaaccttc ttctcaatct caatctcaac ctccttcttc taaaaaatct    60
aaacaacaac aacaacctaa atctccttct tcttctcctc aatctcaatc tccttcttct   120
aaaccttctt cttcttctcc tcaacaacct tctaaatctt ctaaatctcc taaacctcct   180
tctccttctc ctcctccttc taaaaaacct aaatctcctt ctaaaccttc tcctaaacct   240
ccttctcctc ctaaatctaa atctcctaaa caacctcaat cttcttctca atctcaatct   300
tcttcttcta aatcttctca acctccttct cctccttctt ctcaaaaacc ttctcaatct   360
caatcttctt ctcaacctaa accttcttct cctaaacctc aatcttctcc tcaaaaacaa   420
tctccttctc aacctaaaaa atctcaaaaa cctaaaaaac aaaaaaaacc tcaacaacct   480
tcttctcctc aacctaaacc tcaatctcaa cctcaacctc tcaatcttc ttcttctaaa   540
tcttctcctc aatcttctca acaatcttct caatctcctc ctcctcctcc tccttcttct   600
tcttctcctc ctaaatctaa accttctaaa cctcaatctc aaaaacctcc ttctccttct   660
tctaaaccta aatctaaatc ttctcctcaa aaatcttctt ctccttctcc taaatctaaa   720
```

| | |
|---|---|
| tctcctcaac ctcctaaaca acaatctcct cctaaacctc ctcctaaatc tcctcaacct | 780 |
| aaaccttctc ctccttcttc tcctaaaaaa cctaaacctc ctccttctcc taaatctcaa | 840 |
| tcttcttctc aaccttctcc taaatctaaa tctcaacctc cttcttcttc tcaaccttct | 900 |
| ccttcttctt ctcaacaatc tcaatctcct caaccttctt ctcaaaaacc tcctcaatct | 960 |
| ccttctcaaa atctaaaaa atcttctcct ccttctcctc ctcctcctcc ttctcctcct | 1020 |
| tctcaaaaac aacctcctcc tccttcttct cctaaacctc ctcctcaaca atctcctcaa | 1080 |
| aaatctccta atctcctaa acaatctaaa caatctcctc cttctcaacc ttctcctcct | 1140 |
| cctcctcctt cttctcctca acctaaacct tcttctcaac ctaaacctca atctaaacaa | 1200 |
| cctcaacaac cttctaaatc taaacctcct cctcctcaat ctaaacctcc tcctcaatct | 1260 |
| ccttctaaac ctcaacaaca accttctcct cctaaacctc cttctaaacc taaacctcct | 1320 |
| cctcaaccta atctaaatc taaaaaacct aaacaatctc ctaaatctcc taaatctcct | 1380 |
| cctaaaaaat cttctcaaaa atcttcttct cctcctcaat ctcctaaaaa acaaaaatct | 1440 |
| caatctcctt cttcttctca acctcctaaa cctcctaaac ctccttcttc tcctcctcct | 1500 |
| ccttcttctt ctaaacctcc ttctaaaaaa cctcaatctt cttcttcttc tccttctcct | 1560 |
| tctcaacaac ctcaaccttc ttctccttct caacctcctc cttcttctcc tcctcctcct | 1620 |
| caaccttctc aacctccttc tccttcttct aaaaaaaaac aaaaacaacc tcaacaaaaa | 1680 |
| cctcctcaac aacaatctca aaaatctaaa caacaaaaac aacaaaaatc ttctcctcct | 1740 |
| ccttcttctt cttctccttc taaaaaacct cctcctcctt cttctcctaa atctcaaaaa | 1800 |
| aaaaaacctc cttctcaacc ttctcctcaa ccttcttctt ctcaatctcc ttctcaacaa | 1860 |
| tctcaatcta aaccttcttc ttctcctcaa ccttctcctc aacctaaatc tcaatctcct | 1920 |
| caatctcaaa aaccttctcc tcaatcttct ccttctaaat ctaaacctcc ttcttcttct | 1980 |
| tctcaaccta aaccttcttc tccttctcaa caaccttctc aacctcctaa atcttctaaa | 2040 |
| tctaaacaac ctcctcctcc ttctcaacaa ccttctccta acaatcttc ttcttctcct | 2100 |
| aaaaaaaaac ctcctcaacc tcctaaaaaa caatctcaac aaaaacctcc tcctcaacct | 2160 |
| cctcctcctt ctcctcctcc tcctcaacaa aaatcttctt cttctaaatc taaacaaaaa | 2220 |
| tctaaaccttt ctccttctca atcttctcct tctcctcctt ctcctcctcc tcctcaatct | 2280 |
| cctaaacaaa aatcttctaa atctcctcct aaacaaccttt ctcctcctca acctcaatct | 2340 |
| cctaaaaaac aacctcaaaa atctcctcct tctcaatctc cttcttctca atcttctcct | 2400 |
| caaccttctc ctcctccttc ttcttctcaa tctcctcctc ctcctaaatc ttctcaatct | 2460 |
| tcttcttctt cttctaaacc tcctccttct cctaaacctc ctcctcaacc ttctcctcaa | 2520 |
| tcttctcaac ctcaaaaaaa atctcaacct tcttcttcta aatctcctaa acctcctcct | 2580 |
| ccttcttcta aacctcctaa acaatcttct cctaaacctt ctcaacctcc ttcttctcaa | 2640 |
| tctaaacaac aaaacaatc taaaaaaaaa tctaaaaaaa aaccttctcc tcctaaaaaa | 2700 |
| tctaaacaac ctcaacctca atctccttct aaatctccta aaaaaccttc ttctaaatct | 2760 |
| tctaaatctc ctcctaaatc ttctccttct tctccttcta atctcctcc tcaaaaacct | 2820 |
| ccttctcaaa atcttctaa acctcctcct ccttcttctt ctcaatctaa acctcaacaa | 2880 |
| tctcctaaac cttctaaacc ttctcctcct tcttcttctt ctcctcctca acaacaatct | 2940 |
| tcttcttcta aacaatctca atctcctcct cctccttctt ctccttctcc ttctccttct | 3000 |

<210> SEQ ID NO 13
<211> LENGTH: 3000
<212> TYPE: DNA

<213> ORGANISM: Artificial Sequence
<220> FEATURE:
<223> OTHER INFORMATION: Sequence is produced using the reverse
     translation tool located at:
     www.vivo.colostate.edu/molkit/rtranslate/index.html.

<400> SEQUENCE: 13

```
aaacctcctc ctaaatctca aaaaaatct tctaaaaaac ctcaacaaaa atcttctaaa        60
tctcctaaat ctaaaaaatc ttctaaacct caaaacaaa aatctaaacc tcctaaatct       120
aaatctcaac ctcctaaaaa atctaaacaa ccttctaaaa aaaaaaaacc ttctaaaaaa       180
cctcctaaat ctaaacaaca aaaacctaaa aaaaaatctc cttctcctcc tcctcaatct       240
ccttcttcta aaaaaaaacc ttcttcttct cctaaaccta aaaaaaaacc ttctcctcct       300
tcttctaaat ctaaaaaacc taaatctcct tctccttcta aatctaaaca acaatctcct       360
caaaatctc cttctcctaa atctaaacaa caatcttcta aaaatctcc ttcttcttct        420
caatctcctc ctaaatctaa aaatcttct aaaaatctt ctaaaaaatc tccttctcaa        480
aaaaacaac ctcaacctca atcttctcct cctaaacctc ctcaacctaa accttctcct       540
aaaccttctt cttctcctcc tcctaaacct caacaacctc ctaaacctcc ttctcaaaaa       600
tctcctccta aacctaaacc ttcttctcct tctcaaaaaa aatcttctca aaaatctaaa      660
caaaacaac ctcctcctcc ttcttctaaa ccttctaaat ctaaacctaa aaaaaaaaaa       720
tcttctccta aacaacctcc tccttctcct caacaatctt ctaaacctaa aaaatcttct      780
tcttctcaaa aatctcctcc tcaaaaacaa caaaaacctt cttctcaatc ttcttctcct      840
cctcctcaat ctaaatctaa aaaatcttct cctaaaaaat ctcctcctaa atctaaacct      900
tctcaacctc aaccttcttc ttctaaacct cctaaatcta atcttctca acaatcttct       960
tcttctcaaa aaaaccttc tcaacaacaa ccttcttctc ctaaaaaacc tcaatctcct     1020
ccttctcctc ctcctaaacc tcctcctcct caatcttctt cttctaaatc tcctcctaaa     1080
aaatctaaat cttctcctaa acaacctcct tctcctcctt ctcaatcttc tcaacaatct     1140
tctaaatctt ctccttctcc tcctaaaaaa aaaaaacaac ctaaacaatc taaacctaaa     1200
caacaacctt ctaaacaatc taaaaaaaaa cctcctcctc aacctaaaaa atctcctcaa     1260
aaacaaaaat ctcaacctaa aaaacaacaa caaaaacctt ctcctcaacc taaatcttct     1320
tctaaatctt ctaaaccttc ttctcctaaa aaaaacctc aatcttctcc tcctcaacaa       1380
aaacaacctt ctaaacctcc tcaatctcct tctcctcaaa aatctcaaaa atctcctcaa     1440
cctccttctc ctcctaaatc tcctcaacct cctaaaaaat ctaaatcttc ttcttctaaa     1500
tctaaaaaat cttcttctca aaaacctcct cctcaaccta aaccttctca acctaaatct     1560
cctccttctc aatctaaaaa accttctaaa cctccttctc ctccttctaa acctaaacaa     1620
cctcaatctc ctaaatctaa acaacaatct tctcctcctt cttctccttc taaatctaaa     1680
caaaacctc ctaaacaatc ttctcaacct tctcaacctc ctcctaaatc tccttctcct      1740
tcttctccta aatctaaacc taaacctaaa ccttctcaat cttctaaatc ttctaaaaaa     1800
aaaccttcta aacctccttc tcaatctcct tctcaaaaaa aatcttctaa atctcctcct     1860
cctaaatcta aactcctcc ttctcaatct cctaaatcta aaaaaaaatc tccttctcaa      1920
aaatctaaaa aaaaaaaaca aaaaaaacct aaacctaaac ctcctccttc tcaaaaaaaa     1980
caacaaaaat cttcttctcc tcctccttct aaaaaatctt ctccttctaa atctaaacct     2040
ccttctcctc cttctaaaaa atcttctaaa tctcctcctc ctaaaaaaaa acctcctcct     2100
caatctcctt ctcctaaaca atctcctcaa cctaaaaaac cttctaaatc ttctcctcct     2160
```

```
caacaatctc ctaaaaaaaa atctcctaaa caacctcctt ctaaacctaa acctaaacct   2220
cctcctaaac aaaaaccttc ttctaaacct caaaaatctt cttctaaatc taaaaaacct   2280
aaacctcctt ctaaacaatc tcaaaaaaaa tctaaacaac ctcaatctcc tcaaccttct   2340
tctaaacaaa aacctaaacc taaacaatct tctcctccta aatctaaatc taaaaaaaaa   2400
cctcctcaaa aaaaaccttc tcaacctaaa tcttctaaac cttcttctaa acctaaaaaa   2460
aaacaacctc ctcctcctca acctaaacct cctcaaaaaa aatctaaaca atcttctaaa   2520
tctcctcctc ctccttctaa aaaatctaaa ccttctaaaa aatctcaaca caaaaatct   2580 caatctcctt ctcctaaatc ttctcctcct tctcctaaac ctaaaaaatc tcctcctcct   2640
tcttcttctc cttcttcttc tccttcttct cctaaacctc cttcttctca atctcaaaaa   2700
aaacaatctc ctaaacaaca accttctaaa caaaaatctt ctcctcctaa aaaatctaaa   2760
aaacctaaaa aacctcctcc ttctccttct tctaaaaaaa aaaaacctaa aaaatctaaa   2820
tctaaaaaac ctccttctcc taaacaaaaa aaatctaaac aaaaatctaa acctaaacct   2880
cctaaacaac ctcaatcttc tcaacctcct aaacaaccta aacctcaaca caatctcaa   2940 tcttctcaac ctcctcaaca atctcaaaaa cctcaaaaac ctaaatctcc tcaacaatct   3000

<210> SEQ ID NO 14
<211> LENGTH: 3000
<212> TYPE: DNA
<213> ORGANISM: Artificial Sequence
<220> FEATURE:
<223> OTHER INFORMATION: Sequence is produced using the reverse
      translation tool located at:
      www.vivo.colostate.edu/molkit/rtranslate/index.html.

<400> SEQUENCE: 14
caatcttctt ctcctcctaa atcttcttct caatctaaat cttcttcttc ttcttcttct     60
tctccttctc ctaaatctcc ttcttctcct tctaaacctc ctcctccttc taaaaaaaaa    120
cctaaatcta aaaaaaaaca atcttctcct aaatcttcta aacctaaaaa acctaaacaa    180 aaaaatctc ctcctcctca aaaacctaaa aaatctcctt ctaaacctaa atctaaacct     240
tcttcttcta aaaaaaaaaa atctcaacaa caatcttctc aaaaatctca atctaaacaa    300
cctaaaaaac ctcaaccttc tcctaaaaaa cctaaatctc ctaaaaaacc tcctaaacct    360
caacctaaat cttctcctaa acaatctaaa caaaaacctt ctaaaaaaaa accttcttct    420
aaacctaaat ctaaatctaa aaaaaaatct caaaaaccta acaatctaaa aaatcttct     480 tctaaacctc cttctaaatc taaaaaaaaa caacctaaac ctaaaaaaaa atctaaatct    540
tcttcttcta atcttctaa atctccttct aaatctaaat ctcctcaatc ttctaaatct    600
tctcctccta aaaaacctaa acctaaaaaa cctaaaccta atcttctaa atctcctaaa    660 tctcctccta aaaaaaaacc tcaatctcaa aaacaaccta atctcaatc tcctcaacct    720 caaaaaaaac ctaaacaatc ttctaaacaa aaacctaaat ctaaaaaatc tcctaaaaaa    780
cctcctaaaa aatctaaacc taaatctcct cctcctccta aaaacctaa acctaaaaaa    840 tcttctaaac aacctaaatc tcaatcttct caaaaaaaac taaacctcc tcctccttct    900 cctcctaaac aaaaacctca aaaatcttct tctcctccta acaacaatc taaaaaacct    960 tctcctcctc aaaaacctaa acctaaatct tctccttctc cttctaaatc ttctcaatct   1020
aaaaaaaaaa aacctaaaaa acctaaacaa tctcctcctc aaaaacctcc ttctaaacaa   1080
tctcctcaaa aacctaaatc ttcttctcct cctaaaaaaa aaaatcttc taaaaaacaa    1140 aaaaaaaaac aaaaaaaaca aaaatcttct caatctaaac cttctcaaaa acctccttct   1200
```

| | |
|---|---|
| aaacctaaat cttcttcttc taaaaaaaaa caatctaaaa aaaaaaaacc tcctcaaaaa | 1260 |
| tcttctaaaa aacaacaatc tcctcctaaa caatctccta aaccttctcc taaaaaaaaa | 1320 |
| aaacctaaaa aaaacaaaa aaaatctcct aaacaatctc aacctaaaaa acctaaacct | 1380 |
| tctaaacctc aaaaatctca aaaaaaatct ccttctccta aacctcctcc tcaacctaaa | 1440 |
| cctcaaaaaa aatctcctcc taaacctaaa cctaaatctc cttctcctcc tccttctcaa | 1500 |
| aaacctaaaa aaccttctaa acctcaacaa tctcctcaaa aaaacctcc tcctaaatct | 1560 |
| caaaaaaaac ctaaacctcc taaaaaaaaa tctaaatctt cttctcctcc tcaatctaaa | 1620 |
| caacaaaaaa aaaaaaaaa aaaatctcct aaatctaaaa aatctaaaca acctcaacct | 1680 |
| aaacaaaaaa aaaatctaa acctaaatct ccttctcaaa aacctaaaca atcttcttct | 1740 |
| aaacaaaaaa aatctcctaa acctaaacct tctcctaaat cttctaaacc tcaacctaaa | 1800 |
| aaaaaaaaaa aaccttctaa aaaaaaaaaa aaaaaaaac aaaacctcc tcctcaatct | 1860 |
| aaaaaaccta aatctcctcc tcctaaacct aaacctaaat cttcttctaa aaaacctcct | 1920 |
| cctaaaccttt ctaaacctca atctaaaaaa caatctaaat ctaaaaaaaa acctcctaaa | 1980 |
| caaaaaaaaa aacctaaaaa atctcctaaa aaaaaaaaaa aacctccttc ttctaaatct | 2040 |
| tctcctaaat ctcctccttc tcaacaatct cctcctcctc taaacaatc taaacaacct | 2100 |
| ccttctcaat ctaaaaaacc tcctaaacct cctaaaaaa aatcttctaa aaaaaaaaaa | 2160 |
| aaatctaaaa aacctcaaaa acaacctaaa aaaaaatctt cttctaaaca atctaaatct | 2220 |
| aaacctcctt ctccttctca acctccttct ccttctaaac ctccttctcc taaaaaaaaa | 2280 |
| tctccttctc aatctaaacc taaacaaaaa tctccttcta atcttctaa atctaaacaa | 2340 |
| tctaaacctt ctaaacaaca acctaaacaa aaacctcaat cttctcaaaa acctaaatct | 2400 |
| cctaaatcta aaaaaaaatc tcaaaaaaaa caatcttctt ctcctcctaa atctaaatct | 2460 |
| caacaaccta aaccttctca aaaaaaacct cctaaacaac aatcttctaa atctcctcaa | 2520 |
| aaatcttcta aacaaaaacc ttctaaacct tcttctccta aacctcaatc taaacaatct | 2580 |
| aaacaacaaa aaaaaaaaa acaatctaaa caacctccta acaaaaaaa accttctaaa | 2640 |
| tctaaaaaac ctcctcctaa acctcctcct aaatctaaac taaacaaaa aaaacctcaa | 2700 |
| aaaaaccta atcttctaa aaacctcaa caaccttctc cttcttctcc ttcttctaaa | 2760 |
| tcttctaaaa aatctaaatc taaacaaaaa cctcctcctc aacctcctcc ttctcaaaaa | 2820 |
| aaaaaaaaac ctcctcctaa atctcaaaaa aaacctaaaa aaaaaaaatc ttctccttct | 2880 |
| aaaaaaaac ctcctaaaaa aaaatctcct tctcaatctt ctcaaaaatc taaatcttct | 2940 |
| tctcaatctc ctcctcaaca acctcctcaa aaacctaaaa aatctaaaca aaaaaaaaaa | 3000 |

<210> SEQ ID NO 15
<211> LENGTH: 3000
<212> TYPE: DNA
<213> ORGANISM: Artificial Sequence
<220> FEATURE:
<223> OTHER INFORMATION: Sequence is produced using the reverse
      translation tool located at:
      www.vivo.colostate.edu/molkit/rtranslate/index.html.

<400> SEQUENCE: 15

| | |
|---|---|
| tcttctaaac ctaaaaaatc tcctcctttct aaaaacaat ctcaatctaa aaatctaaa | 60 |
| cctaaaaaaa aaaatctca aaacctaaa aaatcttctc taaaaaaaaa atctaaatct | 120 |
| tctaaaaaac cttctcctcc tcaaccttct aaacaaccta acaacaatc tccttctaaa | 180 |
| caatctaaat ctcctaaatc tcaaaaacct ccttctcctc taaaaaaaaa acaaaaaaaa | 240 |

```
ccttctaaac aacctaaatc tcctaaacct cctaaatcta aatctcaaca acctaaacct     300
aaacctcaac aacctaaaaa aaaacctaaa ccttctaaac ctcctcctcc ttcttctcaa     360
aaacaacaaa aatctaaatc tccttctcaa aaaaaaaaa aaccttctaa aaaacctaaa     420
aaaaaacaac ctaaacaatc tccttcttct aaaccttctt ctcaacctaa acaacctcct     480
caaaaaaaaa aaaacctaa acctaaaaaa aaaaaaaac aaaacaacc taaaaaacct     540 aaaaaaaaaa aatctcctaa aaaaaaacct aaacctccta atctaaaaa aaaaaaacct     600 aaatcttcta aaaatctaa acctcaaaaa ccttctcctc taaatctcc taaacctaaa     660 cctaaaccta aaaaaaaacc taaatctaaa aaatctaaat cttctaaacc taaacctcct     720
tctaaaaaaa aacctcctcc ttctcctcct tcttctccta acaaaaatc taaatctcct     780 cctaaaaaaa aacctaaaca aaacctaaa caaaaatcta atcttcttc tcctcaacct     840 aaacctcctt cttctcctaa aaaaaaaaaa aaacaatcta atctaaaaa accttctaaa     900 aaatctcctc ctaaaaaaaa aaaatctcaa caaaaatctt ctaaaaaacc taaaaaacct     960
aaaaaatcta aaaaatcttc taaaaaaaaa tctaaacctc aatctaaacc taaatcttct    1020
aaaaaaaaaa aatcttcttc taaatcttct cctaaaaaac ctaaacctca acaacctaaa    1080
aaaaaaaaac aacaaaaaaa aaaaaatct tctaaaccta acaaaaaaa atctcaaaaa    1140 aaaccttcta aaaaaaaacc taaaaaacct aaacaaaaaa aatctaaaaa atctcctcct    1200 aaaaacaat ctaaacaacc tcctcaaaaa aaatctaaaa aaaacaaaa acctccttct    1260 caaaaaaaat ctcaatcttc tcctaaacct aaacctcctc aaaaacctaa aaaaaaatct    1320
cctaaacctc taaaaaacc tcaaaaaaaa cctaaatcta acaatcttc ttctaaacct    1380 tctaaacctc ctcctcctaa aaaacctcct aaaaaaccta acctaaaaa aaaaaaaaaa    1440 aaatctaaaa aatcttctaa aaaaaaaaaa caaccttctc ctaaaaaacc taaatctaaa    1500
aaaaaaaaaa aatcttctaa accttctaaa ccttctcaac aaaaatctcc taatctaaa    1560 ccttcttctt ctcctcaatc taaacaacct aaacaatctt cttcttcttc taaaaaacct    1620
aaaaaacctc cttctaaatc taaacaacct tcttctaaat ctcctaaatc tcctcctcct    1680
aaaccttctc aaaaacctcc tcctcaaaaa aaacctaaac aaaaaaaatc taaaaaacct    1740
cctaaaaaaa aaaaaaaacc tcaaaaacct aaaaatctt ctccttctcc tcctccttct    1800
cctaaacaaa aaaaaaaca acctccttct aaacaaccta atctaaaaaa atcttctcaa    1860
aaaaaatctt ctaaatctaa aaaaaaaaaa aaaaaaaaac ctcctaaaaa atctaaatct    1920
cctccttctc aatctaaatc taaaccttct cctcctccta aaaaacctaa aaaacaatct    1980
tctcaacaat ctaaatctca acaatcttct aaacctaaac taaacctaa aaaacctcct    2040 cctaaacaat ctccttctcc ttcttctcaa aaaaaaaaa aacctaaatc taaaaaacct    2100
tcttctcctt cttctcctaa atcttcttct ccttcttctt ctccttctaa atcttctaaa    2160
caaaaacctt cttctccttc taaacctaaa aacctaaaa aaaacctaa aaaaaaacct    2220 aaaaaaccta aaaacaacc taaacaaaaa cctaaaaaac ctcctccttc taaaaaacct    2280
aaacctcctt ctaaatctca atctaaaaaa cctaaacaaa aaaatcttc tcctaaaaaa    2340 aaaaatcta aaaatctaa aaatctaaa caacaaaaac aacaaaaaa aaaatctcaa    2400 aaaaaatcta atcttctcc tcctaaatct aaaaacaaa aacaatctaa aaacctaaa    2460 caacctaaaa aaaacaatc taatctcct aaaaacaaa aaaacctaa atcttctcct    2520 tctcaaaaac aacaacaaaa aaaaaaaaaa caaccttcta atcttctaa aaaacctaaa    2580 caaaaaaaaa aatctaaaca atctaaacct aaacaaccta aaaaatcttc tcctcctaaa    2640
```

| | |
|---|---|
| tctccttcta aacaatctaa aaaatctcct tctaaatctc aaaaacctca atctaaaaaa | 2700 |
| tctcctaaat ctaaaaaaaa atcttctaaa aaaaaaaaaa aaaaaaaaaa acctaaaaaa | 2760 |
| cctaaaaaaa aacctaaaaa atctaaatct tcttctcaaa aaaaatctaa acaacctaaa | 2820 |
| tctccttctc aaaatcttc taaaaaaaaa aaacctaaac aatcttctaa aaaaaaacaa | 2880 |
| aaaaaacaaa aacaaaaaaa aaaacaacct tcttctaaac ctcaacctaa aaaaaaacaa | 2940 |
| cctaaaaaaa aacaaaaaaa acctaaaaaa aaaaaatctc ctaaatctcc taaacctaaa | 3000 |

<210> SEQ ID NO 16
<211> LENGTH: 3000
<212> TYPE: DNA
<213> ORGANISM: Artificial Sequence
<220> FEATURE:
<223> OTHER INFORMATION: Sequence is produced using the reverse
 translation tool located at:
 www.vivo.colostate.edu/molkit/rtranslate/index.html.

<400> SEQUENCE: 16

| | |
|---|---|
| aaaaaaaaac aacctaaaaa atctcaacaa aaaaaaaaaa aaaaaaaaca atctaaacct | 60 |
| aaacaaaaaa aacctccttc ttctaaacct cctaaacaaa aaaaaaaaca acctaaaaaa | 120 |
| tctccttcta aatcttcttc taaaaaaaaa caaaaatctc ctaaacctca aaaaaaacct | 180 |
| aaaaaaccta aaaacctaa aaatctaaa aacaacctc aacaacctcc ttctaaacct | 240 |
| tctcctcaat ctaaatctaa acaacctcaa caaaaaaaac ctcctaaacc taaacctcct | 300 |
| aaaaaaccta aaaaaaaaaa acaaccttct caaaaacaat ctaaacctcc taaatctcaa | 360 |
| tctcaaaaaa aatcttctaa acaaaaatct ccttctaaac ctaaacaaaa atcttctaaa | 420 |
| aaaaaaaaaa aaaaaccttc ttcttctcct tctaaatcta aaaaaaaaaa acctaaatct | 480 |
| aaacctccta aaaatctaa acctaaaaaa aaaaaaaaat ctcaatctaa aaaacctaaa | 540 |
| aaaaaaaaac ctaaacaaca acaaaaaacct aaaccttcta acaacaaaa acctaaacct | 600 |
| tcttctaaaa aatcttctcc taaaaaaaaa cctaaacaaa aacctaaacc tcaacctaaa | 660 |
| cctaaaaaac ctaaacctcc taaacctaaa caaaaaaaaa aatctaaacc taaacctaaa | 720 |
| tctcctaaaa aaaacaaca caacaacct aaacctcctc aaaatctcc taaaaatct | 780 |
| cctcctaaaa aacctaaacc taaaaatct tctccttcta atctccttc taaacctaaa | 840 |
| aaacaaaaac ctaaaaaacc ttcttctcaa aaaaaccta atctaaatc tcctcctaaa | 900 |
| aaacaatcta aaaatctaa atctaaatct aaaaaaaaat ctccttcttc taaaaaatct | 960 |
| aaacctaaaa atcttctcc taaaaaacct aaatctaaaa acaatctaa atctaaatct | 1020 |
| caaaacccta atctaaaca atcttctcct aaacaaaaaa aaaatctca aaatctaaa | 1080 |
| cctcaaaaat ctaaaaaaaa atcttctcct aaaaacaaa aatctaaaaa aaaaaatct | 1140 |
| cctaaaaaac cttctaaacc tcctaaaaaa aaacctccta atctaaaca atctaaaaaa | 1200 |
| aaacaatctc ctaaacctaa acctccttct ccttctccta acctaaaaa aaaatctaaa | 1260 |
| aaaaaaaaaa aaaacaacc ttcttctaaa aacaaccta aaaaccttc taaaaaaaaa | 1320 |
| aaacaatctc cttctaaaca acctaaatct aaatcttcta aaaaaaaacc tcctaaaaaa | 1380 |
| caacctaaaa aacctaaaaa aaaaaacaa tcttctaaaa aacctaaaaa atctcctcaa | 1440 |
| aaaaatcta aaaacctca atcttctcct aaaaatctc cttctaaaca acctaaaaaa | 1500 |
| aaaaaaccta aaaaacctaa aaaacctaaa aaaaaaaaac ctcaatcttc tccttctaaa | 1560 |
| cctcctccta atctcaatc taaacaaaaa tctcctccta atcttcttc taaaaaaaaa | 1620 |
| caaaaaaaac ctaaacctaa aaaaaaaaaa aaaccttcta aaaaaaaacc tcctccttct | 1680 |

| | |
|---|---:|
| aaaaaaccta aaaaatctaa aaaatctaaa tctaaaaaaa aatctaaaaa aaaatctcct | 1740 |
| cctaaaaaat ctaaaaaaaa acaacctaaa cctcctaaaa aatctaaaaa aaaatcttct | 1800 |
| aaacaatcta aacctaaaaa atctcctaaa cctaaatcta aaaaaaaatc taaaaaacaa | 1860 |
| aaatcttctt ctaaaaaatc tcctcctcct aaatctaaac ctcctaaacc ttctcaacct | 1920 |
| cctaaatcta aaaaaaaaaa acctccttct aaaaaaaaac taaaaaaaca aaaatcttct | 1980 |
| caaaaaccta aatcttctca aaaaaaaaaa cctcctaaac ctaaaaaaca acctaaatct | 2040 |
| aaaaaccta aaaaacctaa aaaacaacaa caaaaaaaac ctcctaaaaa aaaaaaaaaa | 2100 |
| aaaaaaaaaa aaaaacctaa acctaaaaaa cctcctaaac ctcaatctaa atctaaaaaa | 2160 |
| aaaaaaaaat ctcctccttc tcctccttct cctaaaaaaa aaaaaaaaca aaaaaaaaaa | 2220 |
| tctaaaaaaa aaaaacctaa aaaaaaacct caaaaaaaat cttctaaaca aaaaaaaaaa | 2280 |
| aaaccttctt cttctaaacc taaatctcaa tctaaaaaat cttctaaaaa acctaaacaa | 2340 |
| tctaaacaaa aaaaatctca atctaaaaaa tcttcttcta aatctaaacc tcaaaaaaaa | 2400 |
| tctaaaaaaa aaaaaaaaaa aaacctaaa aaaaaaaaaa aaaaaaatc taaatctaaa | 2460 |
| tcttctcaat ctcaaaaaaa aaaaaaaaaa tctcctaaaa aaaaaaaaaa aaaatctaaa | 2520 |
| aaaaaaaat ctaaaaaacc tcctaaacct aaaaacaat ctaaaaaatc taaatctaaa | 2580 |
| cctcctcctt ctaaacctaa atcttctaaa tctaaaccta aaaaacctcc taaaaaaaaa | 2640 |
| aaacaaaaaa aaaaacaaaa atctaaacct tctaaaaaat ctccttctaa acctccttct | 2700 |
| aaaccttcta acaaaaaaa aaaatctcaa aaaaaacaac ctcaacctcc taaaaaacaa | 2760 |
| cctcctaaat ctaaacctaa acctcctaaa cctcaaaaat cttctaaaaa aaaaaaaaaa | 2820 |
| ccttctaaaa aacctcctaa aaaaaaatct aaaaaacaaa aaaaaaaaaa atctcaatct | 2880 |
| caaaaaaaat cttcttctca aaaacctaaa tcttctaaat cttctcaaaa aaaacctaaa | 2940 |
| aaaaaatcta atcttctaa acaaaaatct aaaaacaaa aatctaaaaa aaaacctaaa | 3000 |

<210> SEQ ID NO 17
<211> LENGTH: 3000
<212> TYPE: DNA
<213> ORGANISM: Artificial Sequence
<220> FEATURE:
<223> OTHER INFORMATION: Sequence is produced using the reverse
translation tool located at:
www.vivo.colostate.edu/molkit/rtranslate/index.html.

<400> SEQUENCE: 17

| | |
|---|---:|
| gaagaacctt ctccttctcc tcctgaatct tcttctgaac ctcctcctcc tcctcctcct | 60 |
| caacctcctg aacctcctca acaatctgaa caacctcaag aatcttctcc ttctcaatct | 120 |
| caatctgaac cttctgaaca acaacaagaa tcttcttctt ctgaacaaga atcttcttct | 180 |
| cctcctgaat ctcaagaaga acctcaatct gaacaacctt cttctcctcc tgaacctcaa | 240 |
| cctcaatctc aatcttctca acctcctcct tctgaatctc cttctcaaca atctgaacct | 300 |
| cctcctgaac aatctcaatc tccttcttct ccttcttctt cttctcaaca atctcaacct | 360 |
| ccttcttctg aaccttctga accttctcct tcttctcctc aatcttctcc ttctccttct | 420 |
| cctcaacaat ctcctgaaga atctgaatct caacctcaat ctccttcttc tcaatctcct | 480 |
| cctcaacctc cttctgaacc ttctcctcct caatcttctg aacctcctga acctccttct | 540 |
| tctgaacctc aacttctcc ttcttctcct cctcaacctg aatctccttc ttcttcttct | 600 |
| tctcctcctt ctcctccttc tcctcaagaa ccttctcctg aacaacctcc tcctcctcct | 660 |
| cctcctcaat ctcctgaatc tcctccttct gaacctcctc aatctcctcc tgaacaagaa | 720 |

| | |
|---|---|
| cctgaacaac ctcctgaacc tgaatcttct cctcctcaat ctcaatcttc tgaacctcaa | 780 |
| tctcaacctg aacctcaatc ttctgaacaa tctgaagaat ctgaatctca acaagaacct | 840 |
| ccttcttctc ctgaacctcc ttcctcctgaa gaagaacaac cttctccttc ttctccttct | 900 |
| cctcctcaat ctcctcctga acctcctcct tcttctgaac tgaatcttc tccttcttct | 960 |
| gaatctcctt ctgaacaatc tcctcctgaa ccttctgaac aatcttctca atctccttct | 1020 |
| ccttctcctc ctcaacaaga acaatctcct cctttctcaat cttctcctga acctccttct | 1080 |
| tctcctgaac tgaagaatc tcctcctcct gaacctgaat cttcttcttc tccttcttct | 1140 |
| tctcaacctg aagaacaacc ttcttctcct tctcctcctt ctcctcctc ttcttctcaa | 1200 |
| tcttctcctt cttctcaatc tccttcttct cctgaagaat ctccttctcc tcctcctcct | 1260 |
| cctcctgaat ctgaaccttc tcctcaacaa ccttctcctc ctcaacaaga acctcctcct | 1320 |
| tctcaatctt ctccttctca acaatctcct cctcctcctt cttctcctcc tccttctgaa | 1380 |
| caacctcctc aagaacctca acctccttct caatcttctc aacctcctga accttcttct | 1440 |
| caatctgaac cttctcctcc tctcaatct cctcctcaac tgaatctcc tcaaccttct | 1500 |
| tcttcttctc aaccttcttc tgaacctcct tctccttctt cttctcctcc tgaaccttct | 1560 |
| ccttctcctg aacaacctcc tccttctcct tctcaagaag aaccttctca agaaccttct | 1620 |
| caatctgaat cttctgaaca atctcaatct cctccttctc cttctgaatc ttctcaatct | 1680 |
| cctcctcaat cttcttcttc tcctcaatct cctgaacctc aacctcctcc ttctgaatct | 1740 |
| caagaatctc aacctcctcc ttctgaatct caaccttctc ctgaagaatc ttctccttct | 1800 |
| tctcaatctg aacaaccttc tcaatctcaa gaacctcaac aatctcctcc tcaaccttct | 1860 |
| cctgaacaac ctgaatctga acaagaatct ccttctcctt ctgaagaatc tgaatcttct | 1920 |
| tcttctcaat ctcctcctcc ttcctcctcaa gaaccttctc ctccttctga atctcaatct | 1980 |
| tctccttctt ctcctcctca accttcttct tctcaagaat ctccttcttc tcaacctcaa | 2040 |
| cctcaatctc aatctcctcc tcaacaacct caacaatctc ctcctccttc tcctcctcct | 2100 |
| caacaatctg aagaacaaga acaagaatct gaacctcaag aacctcaacc tcaatcttct | 2160 |
| cctgaatctc cttcttctga atctgaatct gaatcttctc ctgaacaacc tcctcaacct | 2220 |
| cctccttctc ctgaacctcc tcctcctttct ccttctcctt ctcctccttc tgaatctcaa | 2280 |
| ccttctcaac tcaaccttc ttcttcttct gaatctcctg aagaatctcc tcaacctcct | 2340 |
| cctgaagaat ctccttcttc ttcttcttct gaagaacctc ctcaacctga agaagaacaa | 2400 |
| tcttctgaac cttcttctca atctccttct tcttctcctt ctccttctca atctgaatct | 2460 |
| caatctcaat cttcttctga atcttcttct tctgaatctg aatctcaatc tcctgaacct | 2520 |
| gaagaacctg aacctccttc tcaagaatct cctcctgaac aacctcaaca agaacaacaa | 2580 |
| cctgaagaat cttcttcttc ttcttcttct cctcaatctg aacctcctga agaaccttct | 2640 |
| cctcaacaac aacaatcttc ttcttcttct cctgaatctt ctcctcctcc tgaacaagaa | 2700 |
| caacctgaac aatctcctca acctccttct caatctcctc aatcttcttc tcaagaatct | 2760 |
| tctgaacctc aacctgaaca acaatctcct gaagaagaac cttctccttc tcaatctttct | 2820 |
| tcttcttctc cttcctcctcc tcctcctgaa caatctgaac aacctgaacc tcctgaatct | 2880 |
| cctgaacctc aacaacaatc tcctcaacct ccttcttctc aagaacctga agaacctgaa | 2940 |
| cctcaatctc ctcctgaatc tgaacctcct gaagaagaat ctcaatctcc tcaacctcaa | 3000 |

<210> SEQ ID NO 18
<211> LENGTH: 3000
<212> TYPE: DNA

<213> ORGANISM: Artificial Sequence
<220> FEATURE:
<223> OTHER INFORMATION: Sequence is produced using the reverse
translation tool located at:
www.vivo.colostate.edu/molkit/rtranslate/index.html.

<400> SEQUENCE: 18

```
gaacaacctg aacctccttc tgaatctcct tctccttctc ctccttcttc tgaatcttct      60
cctcctcctt cttctgaacc ttcttctcct caatctcaat ctcctgaaga agaaccttct     120
caatctcaac cttctgaatc ttctcctgaa ccttctcctg aacaatcttc tccttctgaa     180
gaagaacaac ctcctgaatc ttctcaatct caagaatctc aagaacctcc tgaatctcct     240
cctcaacaac cttctcctcc ttctcaagaa tcttctgaac aagaatctcc tgaacaagaa     300
gaatctgaac ctccttctga agaacctgaa cctccttctg aatcttctga agaagaacaa     360
gaacaatctc ctcaatctcc ttcttctgaa cctgaacctg aacaatctca gaatctcct      420
tcttcttctg aatctccttc tcctgaagaa tctcctcctc aacctcctga acctcctgaa     480
tctcctcctc cttctcctga acaagaacaa caacctgaag aagaatctcc tcctcaacct     540
gaatcttctc cttctgaatc ttcttctcct gaatctcctc aagaacctcc ttcttctcct     600
cctcctgaat cttctgaaga agaagaatct caagaatctt ctcctcaaca atctgaagaa     660
caatcttctt ctccttctcc ttctcaatct gaatctcaac aagaatctcc tgaacctcct     720
tctcaacctc cttcttcttc tgaaccttct tctcctctc cttctcctga acctgaacct      780
caacaacctc aacaacaatc tcaacctgaa tctccttctc cttctcctca caaccttct     840
caaccttctg aagaatctcc tgaatctcct gaacctcctt cttctgaacc ttctgaacct     900
tctgaagaac ctgaatctga acaagaacct tcttctcctc tgaatcttc tgaacctgaa      960
caatctcaag aagaacctga acctgaacaa tctcaatctg aatcttctcc tgaagaatct    1020
cctgaatctt ctgaacaaca acaagaacct gaacctcctt ctccttcttc tcaatctcct    1080
ccttcttctc ctccttcttc tgaacctcct tctcctcctg aacctcttcc ttcttctgaa    1140
tctcctgaac aacaacaaga gaacaacctt ctgaagaac ctcaatcttc ttctgaagaa     1200
caatctcaat cttctgaacc tcctgaacct tctcctcaat cttctccttc tcctcaatct    1260
gaacctcctg aacaagaaca agaagaacct gaacaatctg aacctcaacc tgaacctcct    1320
gaacaatctc ctgaaccttc ttcttctcct gaacaacaac tgaacctcc tcctcaatct     1380
tcttctcctc cttctcaaga gaatcttct cctcctgaag aatcttctcc tgaagaatct     1440
tctgaagaac cttcttctga caacaacaa gaaccttctt ctcctcaaga acctgaacct     1500
tcttctcaac ctcctgaacc tcctcaacaa cctgaacctg aacttctga acctcctcct     1560
tctcaatctg aacctcctcc ttctcctcct gaagaacaac aatcttctcc tcctgaacct    1620
gaacctcctc tgaatctcc ttctcaagaa gaacctcctt cttctctca gaagaacaa       1680
caagaacctg aatctcaaga acctgaagaa tctcaacctg aacctccttc tcctcctcaa    1740
cctgaagaag aatctcctca atctgaagaa cctccttctc cttctcaacc ttctccttct    1800
gaagaacaat ctgaaccttc tcaacaacaa gaaccttctc aaccttctga atctcctgaa    1860
tctcctcaag aatctgaaca agaacctgaa gaacctgaat cttctcctga agaagaatct    1920
ccttctcctc aatctcctcc ttcttctcct cctcctgaat ctgaagaaca acctgaagaa    1980
caacctcctc aacaatctcc tgaacctcct ccttcttctc tgaatctcc tgaatctgaa     2040
cctgaagaat ctcctcctga agaatctgaa gaacaacctc aacaaccttc tcaagaagaa    2100
cctcctgaat ctcaagaatc ttcttctcct caatcttctt ctgaagaatc tcctcctcct    2160
```

-continued

```
caagaatctg aacaacctga acctgaatct gaacaagaac ctcctcctga caacaacct      2220 gaacaatctg aacaatcttc tgaacaacaa cctcctcctg aatcttctca acctccttct     2280
tcttcttctg aatctgaaga agaagaagaa tcttctgaac aagaaccttc ttcttctgaa     2340
gaacctgaat cttctgaatc ttcttctgaa caatcttctg aatctgaaga atctgaagaa     2400
gaacctcctc aacaacaaga agaatctcct ccttctgaag aagaagaaca acaacaacct     2460
cctcctgaac ctgaatctga atcctctgaa caatctcaac cttctgaacc ttctccttct     2520
tctgaatctc aagaagaacc tcaagaacct tcttcttctc cttctcctga gaacctcaa      2580 gaagaatctg aagaatctcc tcctgaatct cctgaatctt ctcaaccttc tccttcttct     2640
caagaacctc ctgaatctga agaatctcaa cctgaacaag aatcttctcc tgaagaacct     2700
gaacctcctc ctcctgaacc tgaagaacct cctcctcctc cttctcctga acctgaagaa     2760
gaagaacaac ctcaaccttc tcaacaatct tcttctcaag aagaagaatc tgaatcttct     2820
gaagaacctt cttctgaacc ttcttctgaa cctgaagaat cttcttcttc ttctccttct     2880
tctgaacaac aatctgaatc tcaagaagaa cctgaagaag aatctgaaga acctcctcct     2940
tcttctgaat ctcctgaaga agaagaagaa ccttctgaac ctcctgaatc ttctgaacct     3000
```

<210> SEQ ID NO 19
<211> LENGTH: 3000
<212> TYPE: DNA
<213> ORGANISM: Artificial Sequence
<220> FEATURE:
<223> OTHER INFORMATION: Sequence is produced using the reverse
      translation tool located at:
      www.vivo.colostate.edu/molkit/rtranslate/index.html.

<400> SEQUENCE: 19

```
tctcctgaac aacctgaacc tcaacctgaa cctgaacaag aatctgaacc tgaaccttct       60
gaacctcctc cttctcaaga agaagaatct gaagaagaag aacaatctga acaacctgaa      120
gaagaatctt ctgaaccttc tcctgaatct tctccttctc ctcaagaacc ttctcctcaa      180
caagaacctc cttctgaacc tcaacaagaa tctgaacctt ctcaatctcc ttcttctgaa      240
tctgaacaat ctgaagaaca agaacctcaa gaagaatctg aatctgaaga atctcctgaa      300
tcttctcctt cttctgaacc ttctgaagaa gaatctgaac aatctgaatc ttctgaagaa      360
gaagaacctc cttctcctcc ttctcctgaa gaagaatctc tgaatctca agaacaacaa       420 gaacctgaac aacaatctga acctgaagaa gaatcttctt cttctccttc tctgaacct      480 tctgaagaac ctcctcctga atctgaacct tctgaagaat ctcctccttc tgaacaatct     540
gaacctgaac ctcctcctga atcttctgaa cctcctcaac aagaacaaga atctgaagaa     600
tcttcttctc ctcctgaatc tgaacctcct gaacaatctt ctgaacctga agaagaacaa     660
caatctgaag aagaagaatc tcctgaagaa gaatcttctg aagaatcttc tcctgaacaa     720
tcttcttctt cttctgaaga agaatcttct gaagaacctg aatctcctga agaagaaga      780 ccttctcaac ctgaacaacc tcaacaatct cctcctcaag aatctcctcc tgaagaatct     840
caagaacctc cttctgaatc ttcttcttct gaacaatctt ctgaatctca atctcaatct     900
ccttcttctt cttctgaacc tcaagaacct caacctcctg aaccttcttc tcaagaagaa     960
cctgaacctc ctgaacaaga acctgaacct ctcaacctt ctgaagaatc ttctccttct     1020
tctgaacctg aagaatctcc tcctgaagaa gaatctgaat cttctgaatc tgaagaatct     1080
gaagaagaag aagaagaaga agaatctcct tctccttctc tcaagaacc ttcttctcaa     1140 cctccttctg aagaaccttc tgaagaacct tctcctgaag aacaagaatc tgaagaagaa     1200
```

```
gaatctccctt cttcttctga acaagaagaa ccttctcaat ctgaacaaca atctcctcct    1260
tcttctcctc ctgaatctga acaatctcaa gaagaagaac ctgaagaaga agaacaacct    1320
cctgaacctt ctcaatctcc tgaagaatct gaatctgaag aacaacaatc ttctgaatct    1380
gaacctcctc aatctcctcc tgaagaacct gaacctgaac aacaacaatc ttcttctgaa    1440
gaatctgaac aagaatctga accttctcaa gaagaatctg aatctgaatc tgaagaatct    1500
gaagaatctt ctccttcttc ttctcctcaa cctgaagaac ctgaatctga agaagaacaa    1560
ccttctcctt ctcctgaatc tcaagaacct gaagaatctg aaccttctga gaaccttct     1620 caatctcctg aagaagaaga agaagaacct gaacctgaac tcaacaatc tgaagaagaa     1680 caacctcaag aatcttctca acaagaagaa gaagaacctc ctgaatctga acaacaacct    1740
tcttctgaac aagaagaatc tgaagaacct caacaagaag aaccttctga atctcaacct    1800
caacctcctg aatcttctcc tccttctcct cctcctcctg aagaaccttc tcaagaagaa    1860
tctgaacaag aacctgaaga gaacaatct cctcctgaac ctgaagaaca gaaccttct     1920 ccttctgaat ctgaagaatc tcctcctgaa tctgaatctt ctgaagaaca acaagaagaa    1980
tctgaacctg aatctgaaga gaacctcct caacaatctg aagaacaaca atctcaacct    2040
gaagaagaag aagaagaaca atctgaagaa ccttcttctt ctcctcctga acctcctcaa    2100
caagaacctt cttctccttc tgaacaacct cctcaacctg aagaacctga acctgaagaa    2160
gaatctgaag aaccttctcc tgaacaacct tctgaatctt ctgaacctcc tgaatctcct    2220
gaagaacctt ctcctcctcc tccttcttct gaagaatctg aatctgaatc tgaacaacct    2280
gaagaacaac ctgaatctga agaacctcct tcttctcctt ctgaatcttc tgaagaacct    2340
gaagaagaac ctgaagaaga acaaccttct gaacctcaac ctccttctga acaaccttct    2400
cctcctgaag aacctcaaga gaatctgaa gaagaacctc cttctgaaga accttctcaa    2460
tctgaatctc ctgaacctga accttctcct tcttctcctc ctcctcaaga acctgaacaa    2520
ccttcttctt ctgaacaatc tcctcctgaa ccttctgaac aatctcctcc ttctcaagaa    2580
gaacctgaag aagaaccttc taatctgaa caagaatctg aagaacaacc tcaagaagaa    2640
cctcctcaac cttctcctga accttctcct caagaacctt ctgaacctga acctgaagaa    2700
cctcctgaag aagaacctcc tcaacctcct ccttcttctg aacctgaaga caagaatct     2760 tcttctcctg aacctcaaca acctcaacct tcttcttctc ctgaagaaga acctcctgaa    2820
gaatctcctg aaccttctcc tcaacctgaa cctgaatctg aacctgaaga agaacaatct    2880
ccttctgaac aagaacctga agaagaagaa tctcaagaac cttcttctcc tcaagaacct    2940
gaagaagaac aatctgaatc tgaatctcct tctcctgaac ctgaacctga acctgaagaa    3000
```

<210> SEQ ID NO 20
<211> LENGTH: 3000
<212> TYPE: DNA
<213> ORGANISM: Artificial Sequence
<220> FEATURE:
<223> OTHER INFORMATION: Sequence was produced using the reverse
      translation tool located at:
      www.vivo.colostate.edu/molkit/rtranslate/index.html.

<400> SEQUENCE: 20

```
cctcaagaac cttctgaatc tgaatctcct caaccttctg aatctgaaga gaacaacct      60 gaacaagaat ctcctgaaca atcttctgaa gaaccttctc aagaacaaga gaacaagaa     120 gaaccttctg aagaagaaga acctgaagaa tctcctgaac cttctgaaga caagaacct     180 cctcctcctg aagaacctga gaatctcct cctgaacctg aagaagaaga agaagaagaa    240
```

```
tctgaatctc ctgaacctca atctgaatct gaagaagaat ctcctgaaga acctcctcaa    300
tctgaagaac ctcaatctcc tcaacctgaa ccttctcctg aagaagaacc tcctgaacct    360
gaacaacctg aaccttctcc tcaatctgaa gaacctcaag aacctcaaga agaagaagaa    420
cctgaagaac ctgaacctga agaagaagaa cctcctgaag aagaatctga agaatcttct    480
caagaatctc cttctgaaga accttcttct tctcctgaat ctgaagaaga agaagaacct    540
cctcaagaac cttcttctga atctgaacct gaagaagaat ctcctcaaga agaagaagaa    600
tctgaacaat ctcaagaatc tgaagaacaa caagaagaat ctccttctcc tgaatctgaa    660
tcttctcctc ctgaatctca agaatctgaa tctgaagaag aagaacaaga atctgaatct    720
tcttctcaac cttctgaacc tgaagaagaa caagaagaag aagaagaatc tcctgaacct    780
gaacaagaac ctgaacctga agaatcttct tcttcttctg aatctcaatc tgaatcttct    840
gaacaagaat cttctcaaga atctgaacaa tctcctcctg aagaagaaga atctgaatct    900
tctcaagaat ctgaatctcc tgaatctgaa caagaacaac tcctgaaga atctgaagaa    960 gaacaacctc tgaagaacc tgaagaacaa cctcaagaac ctcaatcttc tcctcaagaa   1020
tctccttctt ctcctgaatc tgaatctcct ccttctgaac ctcctccttc tgaagaagaa   1080
gaacctcctg aacaagaaga acctcctgaa tctgaagaag aacctgaaga agaagaagaa   1140
gaagaagaag aacctgaaga agaagaagaa gaaccttctg aagaatctcc tgaatctgaa   1200
tctgaacctc ctcctccttc ttctgaacct tctgaacctt ctgaacctga atctcctgaa   1260
gaagaatctt ctcctgaaga atctcaatct cctgaagaag aagaagaaga atctgaagaa   1320
gaacctcaac ctgaatcttc tgaacctgaa gaacctgaag aacaagaaca caagaagaa    1380 caagaagaac ctccttctcc tcaacctcct gaagaacaac tcaacaaca agaacaagaa    1440 caatctgaac cttctgaaca acaagaacaa ccttcttctt ctcctgaatc tgaagaagaa   1500
tctgaacctg aagaacctga acctgaacaa gaatctcctc tgaatctgaa gaagaatct    1560 gaacaacctc tgaatctcc ttcttctgaa ccttcttctc tgaagaatc tcaagaatct     1620 tcttctcctg aatctcctga atctccttct cctcctgaat cttctcaacc tgaagaagaa   1680
cctcaacaag aacctgaacc ttcttctcct caacctcaag aacaacctga agaagaagaa   1740
tctcctcctc cttcttctcc tgaacaacct gaagaacctg aagaagaatc ttcttctcaa   1800
tcttctcaag aagaacaacc ttctgaagaa gaatctgaag aagaagaatc tcaagaagaa   1860
ccttctgaat cttctgaaga acctgaagaa gaagaagaag aacctcctga atctcaatct   1920
gaagaacaat ctcaagaaga acaacctgaa tctcctcaag aagaagaaca atctgaatct   1980
cctcctcaac ctcctgaaga acctgaagaa caatcttctc aagaagaatc tgaagaagaa   2040
caaccttctg aacaatcttc tgaagaacct tcttctgaat ctgaagaatc tgaacctcaa   2100
gaatctgaag aagaagaacc tccttctgaa cctgaatctg aacaacaatc tgaagaacct   2160
cctcaatctc aagaagaatc tcctcaacct tctccttctg aacctgaaga agaagaacaa   2220
ccttctgaag aagaacctc tcaagaacaa gaacctgaag aagaagaaga agaagaatct   2280
tctgaacctc ctgaagaaga agaacctcaa gaagaacctg aagaacctcc tgaagaagaa   2340
gaagaagaag aacaatctga agaagaagaa gaacctgaag aaccttctga acaagaagaa   2400
gaacctcctg aagaacctga agaatctgaa tctgaatctc cttctcctga accttcttct   2460
tctgaacaat cttctccttc tgaacaagaa caatcttctg aagaatctca acctgaacct   2520
gaacctgaag aacaatctga agaatcttct caacctcctg aacctgaacc tcctcctcct   2580
cctgaatctg aatcttcttc ttctgaatct gaatctgaac aatctgaatc tcaagaagaa   2640
```

-continued

```
cctgaacctt ctgaagaacc ttctgaacaa tcttctgaat ctgaagaacc tgaatctgaa    2700
gaagaagaag aatctcctga agaacctgaa caagaacaac cttctgaacc tgaagaacct    2760
gaacctgaat ctgaacaaga agaagaatct gaatctcctc ctcctcctcc ttctgaagaa    2820
tctcctcctc aatcttctga accttctcct gaagaacaac ctcaagaatc tgaacctgaa    2880
cctgaacctt cttctcctcc tgaacctcct cctgaagaag aatcttctga acctgaatct    2940
gaagaagaat ctgaatcttc tgaacaagaa cctgaagaac ctcctgaatc tgaatctgaa    3000
```

<210> SEQ ID NO 21
<211> LENGTH: 3000
<212> TYPE: DNA
<213> ORGANISM: Artificial Sequence
<220> FEATURE:
<223> OTHER INFORMATION: Sequence was produced using the reverse
      translation tool located at:
      www.vivo.colostate.edu/molkit/rtranslate/index.html.

<400> SEQUENCE: 21

```
gaagaagaag aatcttctcc tcctgaagaa gaagaatctt ctcctgaacc tgaagaacct      60
gaacctgaac cttctcctcc tcaagaagaa gaagaagaac cttctcctca agaacaacaa     120
cctcaacaac aagaatcttc tcaagaagaa gaacaagaac ctgaagaaga agaacaagaa     180
tcttcttctc tcaagaagaa acctcctcaa cctgaagaag aacctgaacc tgaagaagaa     240
gaagaatctt cttctgaaga agaagaacct gaagaacaag aacaacctga acctgaagaa     300
gaaccttctc ctgaatcttc tgaatctgaa tcttcttctt ctgaagaaga agaagaacaa     360
ccttctcaac ctgaatcttc tccttctgaa gaagaacaac ctcaagaacc tgaagaacct     420
gaacctgaag aagaatctcc ttctcctcct gaagaacaag aagaagaatc tgaatctgaa     480
gaagaacaag aacaatctga acctgaagaa tctgaagaag aagaagaacc ttcttctcct     540
caatctgaac aagaagaacc tcaagaacct gaacctgaag aacaagaaga gaacctcct      600 gaagaagaag aacaagaacc tcctgaatct gaatctcctg aagaacaaga agaagaacaa     660
cctccttctc ctgaagaaga atctgaagaa gaagaagaac tgaagaagaa gaagaacaa     720 gaagaatctg aagaagaaga atctcaatct ccttctgaag aacctgaacc tgaagaatct     780
tcttctcctg aatctgaaga acctcctgaa gaagaatctt ctgaagaatc ttctgaagaa     840
tctcaagaag aatctccttc tcctgaagaa gaagaagaat cttctgaatc tgaacaacct     900
cctgaatctc cttctgaatc tcaagaatct ccttctcaat ctgaagaaga atctcaagaa     960
gaacctcctg aagaagaatc ttcctgaa gaagaacctc ctccttctcc ttctgaatct    1020
gaacctcctg aagaagaaga gaaccttct gaatctgaag aagaagaacc tcctcctgaa    1080
gaagaagaat cttcttctga agaacaagaa tctgaagaac tgaatctga agaagaatct    1140 cctgaagaac aatctgaaga agaagaagaa tctcaagaat cttctcctga acctcctgaa    1200
gaatctcctt ctgaacaacc tgaaccttct cctcctgaac ctgaatctga atcttctgaa    1260
cctgaagaag aagaagaaga agaagaagaa cctccttctt ctgaagaaga gaatctgaa    1320 gaacctgaac aacctgaaga agaacaagaa gaacctcaag aagaagaaga atctccttct    1380
gaagaatctc ctgaagaacc tgaagaatct gaacctgaag aagaatctga agaagaagaa    1440
cctgaacaac aacctgaaga agaacctcct gaagaagaag aacaagaatc ttctgaacct    1500
tcttctcctc cttctgaaga acaatctgaa gaacctgaag aacaagaaga acctcctgaa    1560
ccttctcaac ctgaacctca acaagaatct gaatcttctt ctccttctga atctcaacct    1620
gaatctcaag aatctgaaga agaagaagaa gaagaagaat ctgaagaaga atctgaacct    1680
```

| | | |
|---|---|---|
| tctcaagaac ctgaagaaca acaacctgaa gaagaagaag aagaagaaga agaacctgaa | 1740 |
| gaagaagaag aacaatctga acctgaagaa tcttctgaac aacaagaacc tcctcaatct | 1800 |
| tctcaacctc aagaagaatc tgaacaagaa caagaagaac ctcaatctcc tgaagaagaa | 1860 |
| tctcctcctc ctgaagaaga agaacctcaa gaagaacctc ctgaacctga agaagaagaa | 1920 |
| ccttctgaac aacctccttc ttctcctcct gaagaacaat ctgaacaacc tgaacaatct | 1980 |
| gaacctcaat ctgaatctcc ttctcaacct gaatcttctg aacaacctga gaacaacct | 2040 |
| gaacctcctt ctcctcaatc ttctgaagaa tctgaagaac ctgaagaaga gaacaatct | 2100 |
| gaagaacctt ctccttctca atctgaatct tcttcttctc ctgaagaatc tgaacctcct | 2160 |
| gaagaagaag aagaagaaga agaacctgaa gaacctgaac aagaagaaga acaatctgaa | 2220 |
| cctcaagaac aagaaccttc tgaagaatct tctgaacctg aagaagaatc ttctccttct | 2280 |
| tctcaatctt ctgaacaatc ttcttctgaa gaagaatctg aatctgaaca atcttctcct | 2340 |
| cctcctgaag aagaatctcc tgaagaagaa gaacctgaag aagaagaacc tgaagaatct | 2400 |
| cctgaagaag aatctgaaga atctcctgaa tctgaagaat ctgaagaatc ttctgaagaa | 2460 |
| caagaagaat cttctcctga agaagaacct tctgaacaag aagaacctcc tgaacaagaa | 2520 |
| cctgaatctc ctcctgaaca agaagaagaa gaagaacaat ctgaacctca agaagaagaa | 2580 |
| cctcctgaat cttctgaacc tgaagaagaa tctcctcctg aagaacctca atctgaagaa | 2640 |
| gaagaagaag aacctcaacc tgaatctgaa tctgaacctg aagaaccttc tcctgaacct | 2700 |
| gaatctgaag aatctgaaga agaacctgaa tctgaatctt cttctcctcc tgaatcttct | 2760 |
| tctgaagaag aagaagaaga acctgaagaa caatctgaag aagaagaaga atctcaagaa | 2820 |
| gaagaagaac aagaagaaga accttctcaa gaagaagaag aacctgaaga acaacaacct | 2880 |
| ccttctgaag aagaagaaca acctgaacaa tctgaagaac ctgaaccttc tgaaccttct | 2940 |
| gaagaagaac ctgaacctga agaatctcct cctgaatctc aacctccttc tgaagaacct | 3000 |

<210> SEQ ID NO 22
<211> LENGTH: 3000
<212> TYPE: DNA
<213> ORGANISM: Artificial Sequence
<220> FEATURE:
<223> OTHER INFORMATION: Sequence was produced using the reverse
translation tool located at:
www.vivo.colostate.edu/molkit/rtranslate/index.html.

<400> SEQUENCE: 22

| | | |
|---|---|---|
| ggtcaacaag gttcttctcc tccttctcct tctcaaggtg gtcaacctcc ttcttctcaa | 60 |
| ccttctcaac aatcttcttc ttctcctcct ccttctcctc ctccttcttc tcctccttct | 120 |
| caacctcctt ctcctccttc ttctggttct ggttcttctt ctccttctca aggttctcct | 180 |
| ccttctcctc cttctcaagg tcctcctcaa cctcctcaat cctctggttc tcaaggtcct | 240 |
| cctcctcctc ctggtcctgg ttctggtcct cctccttctt cttctcctca accttctcaa | 300 |
| cctcctcctt ctcaaccttc tcaacaatct cctcaacctt ctcctggtcc tggttctcct | 360 |
| tctcaacaac cttcttctgg ttctcaacaa tctcctggtc aaggtcctca acctcaaggt | 420 |
| ccttctggtt ctcctcaagg tcaaggttct cctggttctt cttctggtcc tcaaccttct | 480 |
| tctcaaggtt ctcctcctgg tcctcctcct ggtccttctc cttctggtgg tcctcaatct | 540 |
| tctcctggtt ctcctccttc tcctcaaggt tctcaacctc aatctcctgg tccttcttct | 600 |
| ccttcttctt ctcctcaacc tcttctggt cctccttctt ctggtggtca atcttctcaa | 660 |
| ggtcaatctc cttctcaagg tcctcctcct ggttctcctc aacctcctgg tggttctggt | 720 |

```
ccttctccctt cttcttctcc tcctccttct cctcctcctc ctcaatcttc ttcttctggt      780
tctcaacaat cttcttcttc ttctggttct cctccttctt cttctcaagg tcctcctcaa      840
tcttcttctc aacctcaatc tcaatcttct ccttctcaac ctccttctgg ttctcctggt      900
tcttcttctt ctccttctcc ttcctcttct ggtccttctg gttctccttc tggtcctcct      960
tcttctcctt ctggttctcc tcctcctggt ggtcctcctc aatctggtgg tcctggtcct     1020
tcttctggtc aacaacctcc tggtcctcaa cctggttctc ctcctggtca acctcaacct     1080
ggttcttctt ctcaaggtcc tcaacaaggt cctcctcctg ttctcctcca aggtccttct     1140
caacctggtc ctcaatctcc tccttcttct ggtggttctt cttctcaacc tcaatctcct     1200
tcttctggtc ctggtcaacc ttctccttct cctcctggtt ctcctggtgg tcctggtcaa     1260
cctccttctc aacctctcc ttcttcttct tcttctcaat ctggtcaatc ttctcaacct     1320
tctggtcctc cttctggtca atctcaacct ggtcaacctc ctcaaccttc tcctccttct     1380
cctcctcctc cttctcctcc ttctcaatct ggttctggtt ctcctggtcc tccttctggt     1440
cctcaacctt cttctcaacc ttctccttct caacctggtc aaggtccttc ttcttctcct     1500
cctggtcaat ctggtccttc ttctccttct tcttctcaac ctcctccttc tcaatctcct     1560
cctcaatctg gtcaatctcc ttcttcttct cctcctcaat cttctccttc ttctggtcaa     1620
caaccttctc ctggtcctcc ttcttcttct tctcctcaac cttcttcttc tcaaggttct     1680
cctcctcctc aacctcaagg tcaatctcct ccttctcaac aaccttctca acctggtggt     1740
tcttctcaac cttcttctcc tcctcctcct ggtcctcaag tcctcaacc tccttctcct     1800
caacctcctt ctggtcctgg ttctcaacct caaggtggtt ctccttcttc tcaaggtggt     1860
caacttctt cttctcctcc tcaatctcct tctggtcctt ctggtcctgg ttcttctcct     1920
tctcaatctc cttctggtca aggtccttct tctcaacctt ctccttctgg ttctggtcaa     1980
cctcaaggtc ctccttctcc ttctggtcaa cctccttctc ctccttctgg ttctcctttct     2040
cctcctcaac ctggttctcc tggtcaacct caaccttctc ctccttctca atctcctggt     2100
ggtcctggtg gtcctcaagg tcctccttct tctcctggtt ctttctggttc ttctggttct     2160
tctcaacctc ctcctcctcc ttctcaacaa tcttcttctg gtcaatctcc tcaacctcaa     2220
ggtcaaggtc aacaacctgg ttctcctggt caatctggtc aacaatctca atctcctggt     2280
ggtccttctc ctcaacaacc tcctcctcct cctcctcctc ctcctggttc ttctcctcaa     2340
tcttctcctc aaccttctcc ttctcaatct caacctcaat ctggttctca atcttctcaa     2400
caacaatctc aatcttcttc ttctccttct cctcaatctc aaggtggtcc tcaatcttct     2460
ggttcttctc cttcttctgg tcctcaatct ccttctcctg gtggtcctcc tcttctcaa     2520
tcttcttctg gtcaaccttc tcctccttct cctcctggtc cttctggttc ttcttcttct     2580
tcttctggtt ctggttctgg tcctcaacct tcctcctcc ctcaatctcc ttctcaacaa     2640
tctggttctt ctcaatcttc tccttctcaa tctcaacctc aaacctcctcc tcctggttct     2700
ggtcaacctc ctccttctgg tggtcctcaa caacctcctt ctcctcaaca aggttctcaa     2760
tcttcttctc aacctcctcc tcctcaatct tcttcttctg gtggtcctgg tcaatcttct     2820
ggttctcctg gtccttctcc tcctcaacaa tctggtggtt ctcctcctcc ttctggtggt     2880
ggttctggtc ctggttctcc tcttctggt caaggttctc cttctcaatc ttctggtcct     2940
tctggtggtc ctggtggttc tcctcctcct ccttcttctc cttctccttc tcaatcttct     3000
```

<210> SEQ ID NO 23
<211> LENGTH: 100
<212> TYPE: PRT

```
<213> ORGANISM: Artificial Sequence
<220> FEATURE:
<223> OTHER INFORMATION: The sequence was produced using the random
      sequence generator tool located at the Swiss-Prot
      website: http://au.expasy.org/tools/randseq.html.

<400> SEQUENCE: 23

Pro Ser Lys Ser Pro Ser Lys Pro Pro Gln Pro Ser Lys Pro Pro
1               5                   10                  15

Gln Ser Lys Lys Pro Gln Ser Gln Ser Pro Pro Pro Gln Ser Ser Pro
                20                  25                  30

Lys Ser Pro Pro Lys Pro Pro Gln Ser Lys Gln Gln Pro Ser Ser Pro
                35                  40                  45

Ser Pro Gln Gln Pro Ser Lys Lys Ser Ser Ser Gln Ser Gln Pro
    50                  55                  60

Ser Gln Lys Ser Ser Pro Lys Ser Ser Lys Pro Pro Ser Gln Lys
65                  70                  75                  80

Pro Pro Lys Pro Lys Pro Lys Pro Pro Pro Lys Ser Pro Gln Ser Lys
                85                  90                  95

Pro Gln Gln Lys
            100

<210> SEQ ID NO 24
<211> LENGTH: 30
<212> TYPE: PRT
<213> ORGANISM: Artificial Sequence
<220> FEATURE:
<223> OTHER INFORMATION: The sequence was produced using the random
      sequence generator tool located at the Swiss-Prot
      website: http://au.expasy.org/tools/randseq.html.

<400> SEQUENCE: 24

Lys Ser Pro Pro Lys Pro Pro Gln Ser Lys Gln Gln Pro Ser Ser Pro
1               5                   10                  15

Ser Pro Gln Gln Pro Ser Lys Lys Ser Ser Ser Ser Gln Ser
                20                  25                  30

<210> SEQ ID NO 25
<211> LENGTH: 100
<212> TYPE: PRT
<213> ORGANISM: Artificial Sequence
<220> FEATURE:
<223> OTHER INFORMATION: The sequence was produced using the random
      sequence generator tool located at the Swiss-Prot
      website: http://au.expasy.org/tools/randseq.html.

<400> SEQUENCE: 25

Pro Ser Glu Ser Pro Ser Glu Pro Pro Gln Pro Ser Glu Pro Pro
1               5                   10                  15

Gln Ser Glu Glu Pro Gln Ser Gln Ser Pro Pro Pro Gln Ser Ser Pro
                20                  25                  30

Glu Ser Pro Pro Glu Pro Pro Gln Ser Glu Gln Gln Pro Ser Ser Pro
                35                  40                  45

Ser Pro Gln Gln Pro Ser Glu Glu Ser Ser Ser Gln Ser Gln Pro
    50                  55                  60

Ser Gln Glu Ser Ser Pro Glu Ser Ser Glu Pro Pro Ser Gln Glu
65                  70                  75                  80

Pro Pro Glu Pro Glu Pro Glu Pro Pro Pro Glu Ser Pro Gln Ser Glu
                85                  90                  95

Pro Gln Gln Glu
            100
```

```
<210> SEQ ID NO 26
<211> LENGTH: 30
<212> TYPE: PRT
<213> ORGANISM: Artificial Sequence
<220> FEATURE:
<223> OTHER INFORMATION: The sequence was produced using the random
      sequence generator tool located at the Swiss-Prot
      website: http://au.expasy.org/tools/randseq.html.

<400> SEQUENCE: 26

Glu Ser Pro Pro Glu Pro Pro Gln Ser Glu Gln Gln Pro Ser Ser Pro
1               5                   10                  15

Ser Pro Gln Gln Pro Ser Glu Glu Ser Ser Ser Ser Gln Ser
            20                  25                  30

<210> SEQ ID NO 27
<211> LENGTH: 100
<212> TYPE: PRT
<213> ORGANISM: Artificial Sequence
<220> FEATURE:
<223> OTHER INFORMATION: The sequence was produced using the random
      sequence generator tool located at the Swiss-Prot
      website: http://au.expasy.org/tools/randseq.html.

<400> SEQUENCE: 27

Pro Ser Gly Ser Pro Ser Pro Gly Pro Pro Gln Pro Ser Gly Pro Pro
1               5                   10                  15

Gln Ser Gly Gly Pro Gln Ser Gln Ser Pro Pro Pro Gln Ser Ser Pro
            20                  25                  30

Gly Ser Pro Pro Gly Pro Pro Gln Ser Gly Gln Gln Pro Ser Ser Pro
        35                  40                  45

Ser Pro Gln Gln Pro Ser Gly Gly Ser Ser Ser Ser Gln Ser Gln Pro
    50                  55                  60

Ser Gln Gly Ser Ser Pro Gly Ser Ser Gly Pro Pro Pro Ser Gln Gly
65                  70                  75                  80

Pro Pro Gly Pro Gly Pro Gly Pro Pro Pro Gly Ser Pro Gln Ser Gly
                85                  90                  95

Pro Gln Gln Gly
            100

<210> SEQ ID NO 28
<211> LENGTH: 30
<212> TYPE: PRT
<213> ORGANISM: Artificial Sequence
<220> FEATURE:
<223> OTHER INFORMATION: The sequence was produced using the random
      sequence generator tool located at the Swiss-Prot
      website: http://au.expasy.org/tools/randseq.html.

<400> SEQUENCE: 28

Gly Ser Pro Pro Gly Pro Pro Gln Ser Gly Gln Gln Pro Ser Ser Pro
1               5                   10                  15

Ser Pro Gln Gln Pro Ser Gly Gly Ser Ser Ser Ser Gln Ser
            20                  25                  30

<210> SEQ ID NO 29
<211> LENGTH: 300
<212> TYPE: DNA
<213> ORGANISM: Artificial Sequence
<220> FEATURE:
<223> OTHER INFORMATION: Sequence was produced using the reverse
      translation tool located at:
      www.vivo.colostate.edu/molkit/rtranslate/index.html

<400> SEQUENCE: 29
```

```
ccttctaaat ctccttctcc taaacctcct caaccttcta aacctcctca atctaaaaaa    60
cctcaatctc aatctcctcc tcctcaatct tctcctaaat ctcctcctaa acctcctcaa   120
tctaaacaac aaccttcttc tccttctcct caacaacctt ctaaaaaatc ttcttcttct   180
caatctcaac cttctcaaaa atcttctcct aaatcttcta aacctcctcc ttctcaaaaa   240
cctcctaaac ctaaacctaa acctcctcct aaatctcctc aatctaaacc tcaacaaaaa   300
```

\<210\> SEQ ID NO 30
\<211\> LENGTH: 90
\<212\> TYPE: DNA
\<213\> ORGANISM: Artificial Sequence
\<220\> FEATURE:
\<223\> OTHER INFORMATION: Sequence was produced using the reverse
      translation tool located at:
      www.vivo.colostate.edu/molkit/rtranslate/index.html

\<400\> SEQUENCE: 30

```
aaatctcctc ctaaacctcc tcaatctaaa caacaacctt cttctccttc tcctcaacaa    60
ccttctaaaa aatcttcttc ttctcaatct                                     90
```

\<210\> SEQ ID NO 31
\<211\> LENGTH: 300
\<212\> TYPE: DNA
\<213\> ORGANISM: Artificial Sequence
\<220\> FEATURE:
\<223\> OTHER INFORMATION: Sequence was produced using the reverse
      translation tool located at:
      www.vivo.colostate.edu/molkit/rtranslate/index.html

\<400\> SEQUENCE: 31

```
ccttctgaat ctccttctcc tgaacctcct caaccttctg aacctcctca atctgaagaa    60
cctcaatctc aatctcctcc tcctcaatct tctcctgaat ctcctcctga acctcctcaa   120
tctgaacaac aaccttcttc tccttctcct caacaacctt ctgaagaatc ttcttcttct   180
caatctcaac cttctcaaga atcttctcct gaatcttctg aacctcctcc ttctcaagaa   240
cctcctgaac ctgaacctga acctcctcct gaatctcctc aatctgaacc tcaacaagaa   300
```

\<210\> SEQ ID NO 32
\<211\> LENGTH: 90
\<212\> TYPE: DNA
\<213\> ORGANISM: Artificial Sequence
\<220\> FEATURE:
\<223\> OTHER INFORMATION: Sequence was produced using the reverse
      translation tool located at:
      www.vivo.colostate.edu/molkit/rtranslate/index.html

\<400\> SEQUENCE: 32

```
gaatctcctc ctgaacctcc tcaatctgaa caacaacctt cttctccttc tcctcaacaa    60
ccttctgaag aatcttcttc ttctcaatct                                     90
```

\<210\> SEQ ID NO 33
\<211\> LENGTH: 300
\<212\> TYPE: PRT
\<213\> ORGANISM: Artificial Sequence
\<220\> FEATURE:
\<223\> OTHER INFORMATION: Sequence was produced using the reverse
      translation tool located at:
      www.vivo.colostate.edu/molkit/rtranslate/index.html

\<400\> SEQUENCE: 33

```
Cys Cys Thr Thr Cys Thr Gly Gly Thr Thr Cys Thr Cys Cys Thr Thr
1               5                   10                  15
```

Cys Thr Cys Cys Thr Gly Gly Thr Cys Thr Cys Cys Thr Cys Ala
                20                  25                  30

Ala Cys Cys Thr Thr Cys Thr Gly Gly Thr Cys Cys Thr Cys Thr
                35                  40                  45

Cys Ala Ala Thr Cys Thr Gly Gly Thr Gly Gly Thr Cys Cys Thr Cys
    50                  55                  60

Ala Ala Thr Cys Thr Cys Ala Ala Thr Cys Cys Cys Thr Cys Cys
65                  70                  75                  80

Thr Cys Cys Thr Cys Ala Ala Thr Thr Thr Cys Thr Cys Cys Thr
                85                  90                  95

Gly Gly Thr Thr Cys Thr Cys Cys Thr Cys Thr Gly Gly Thr Cys
                100                 105                 110

Cys Thr Cys Cys Thr Cys Ala Ala Thr Cys Thr Gly Gly Thr Cys Ala
    115                 120                 125

Ala Cys Ala Ala Cys Cys Thr Thr Cys Thr Thr Cys Thr Cys Cys Thr
    130                 135                 140

Thr Cys Thr Cys Cys Thr Cys Ala Ala Cys Ala Ala Cys

```
<221> NAME/KEY: VARIANT
<222> LOCATION: 3, 8, 14, 19, 20, 33, 37, 42, 55, 56, 67, 71, 74, 80,
      83, 85, 87, 91, 96, 100
<223> OTHER INFORMATION: Xaa = Lys, Glu or Gly

<400> SEQUENCE: 35

Pro Ser Xaa Ser Pro Ser Pro Xaa Pro Pro Gln Pro Ser Xaa Pro Pro
 1               5                  10                  15

Gln Ser Xaa Xaa Pro Gln Ser Gln Ser Pro Pro Pro Gln Ser Ser Pro
            20                  25                  30

Xaa Ser Pro Pro Xaa Pro Pro Gln Ser Xaa Gln Gln Pro Ser Ser Pro
            35                  40                  45

Ser Pro Gln Gln Pro Ser Xaa Xaa Ser Ser Ser Gln Ser Gln Pro
 50                  55                  60

Ser Gln Xaa Ser Ser Pro Xaa Ser Ser Xaa Pro Pro Ser Gln Xaa
65                  70                  75                  80

Pro Pro Xaa Pro Xaa Pro Xaa Pro Pro Pro Xaa Ser Pro Gln Ser Xaa
            85                  90                  95

Pro Gln Gln Xaa
            100

<210> SEQ ID NO 36
<211> LENGTH: 4237
<212> TYPE: DNA
<213> ORGANISM: Artificial Sequence
<220> FEATURE:
<223> OTHER INFORMATION: pAquoProt expression vector backbone

<400> SEQUENCE: 36
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgtt cagatctcct ttcagcaaaa aaccccctca agacccgttt agaggcccca    240
ggggttatgc tagttattgc tcagcggtgg cagcagccta ggttaattaa gctacgctag    300
tttaagcgta atctggaaca tcgtatgggt aaccctcgag tgcggccgca agcttggtac    360
cgatatcctc ccaattggga tccggactct tgtcgtcgtc atcattcgaa ccggcaccgt    420
ggtgatggtg atggtgtgcc atggtatatc tccttcttaa agttaaacaa aattatttct    480 agagggaat tgttatccgc tcacaattcc ctatagtga gtcgtattaa ttcgcggtcg     540
accagctgca ttaatgaatc ggccaacgcg cggggagagg cggtttgcgt attgggcgct    600
cttccgctga caccatcgaa tggcgcaaaa cctttcgcgg tatggcatga tagcgcccgg    660
aagagagtca attcagggtg gtgaatgtga accagtaac gttatacgat gtcgcagagt     720
atgccggtgt ctcttatcag accgtttccc gcgtggtgaa ccaggccagc cacgtttctg    780
cgaaaacgcg ggaaaaagtg gaagcggcga tggcggagct gaattacatt cccaaccgcg    840
tggcacaaca actggcgggc aaacagtcgt tgctgattgg cgttgccacc tccagtctgg    900
ccctgcacgc gccgtcgcaa attgtcgcgg cgattaaatc tcgcgccgat caactgggtg    960
ccagcgtggt ggtgtcgatg gtagaacgaa gcggcgtcga agcctgtaaa gcggcggtgc   1020
acaatcttct cgcgcaacgc gtcagtgggc tgatcattaa ctatccgctg gatgaccagg   1080
atgccattgc tgtggaagct gcctgcacta atgttccggc gttatttctt gatgtctctg   1140
accagacacc catcaacagt attatttttc tcccatgaaga cggtacgcga ctgggcgtgg   1200
agcatctggt cgcattgggt caccagcaaa tcgcgctgtt agcgggccca ttaagttctg   1260
```

```
tctcggcgcg tctgcgtctg gctggctggc ataaatatct cactcgcaat caaattcagc    1320
cgatagcgga acgggaaggc gactggagtg ccatgtccgg ttttcaacaa accatgcaaa    1380
tgctgaatga gggcatcgtt cccactgcga tgctggttgc aacgatcag atggcgctgg     1440 gcgcaatgcg cgccattacc gagtccggc tgcgcgttgg tgcggacatc tcggtagtgg     1500
gatacgacga taccgaagac agctcatgtt atatcccgcc gttaaccacc atcaaacagg    1560
attttcgcct gctggggcaa accagcgtgg accgcttgct gcaactctct cagggccagg    1620
cggtgaaggg caatcagctg ttgcccgtct cactggtgaa agaaaaaacc ccctggcgc     1680 ccaatacgca aaccgcctct ccccgcgcgt tggccgattc attaatgcag ctggcacgac    1740
aggtttcccg actggaaagc gggcagtgag ctcttccgct atcctcgctc actgactcgc    1800
tgcgctcggt cgttcggctg cggcgagcgg tatcagctca ctcaaaggcg gtaatacggt    1860
tatccacaga atcaggggat aacgcaggaa agaacatgtg agcaaaaggc cagcaaaagg    1920
ccaggaaccg taaaaaggcc gcgttgctgg cgttttttcca taggctccgc cccctgacg    1980 agcatcacaa aaatcgacgc tcaagtcaga ggtggcgaaa cccgacagga ctataaagat    2040
accaggcgtt ccccctgga agctccctcg tgcgctctcc tgttccgacc ctgccgctta    2100
ccggatacct gtccgccttt ctcccttcgg gaagcgtggc gctttctcat agctcacgct    2160
gtaggtatct cagttcggtg taggtcgttc gctccaagct gggctgtgtg cacgaaccc    2220 ccgttcagcc cgaccgctgc gccttatccg gtaactatcg tcttgagtcc aacccggtaa    2280
gacacgactt atcgccactg gcagcagcca ctggtaacag gattagcaga gcgaggtatg    2340
taggcggtgc tacagagttc ttgaagtggt ggcctaacta cggctacact agaaggacag    2400
tatttggtat ctgcgctctg ctgaagccag ttaccttcgg aaaaagagtt ggtagctctt    2460
gatccggcaa acaaaccacc gctggtagcg gtggttttt tgtttgcaag cagcagatta    2520
cgcgcagaaa aaaaggatct caagaagatc ctttgatctt ttctacgggg tctgacgctc    2580
agtggaacga aaactcacgt taagggattt tggtcatgag attatcaaaa aggatcttca    2640
cctagatcct tttaaattaa aaatgaagtt ttaaatcaat ctaaagtata tatgagtaaa    2700
cttggtctga cagttaccaa tgcttaatca gtgaggcacc tatctcagcg atctgtctat    2760
ttcgttcatc catagttgcc tgactccccg tcgtgtagat aactacgata cgggagggct    2820
taccatctgg ccccagtgct gcaatgatac cgcgagaccc acgctcaccg gctccagatt    2880
tatcagcaat aaaccagcca gccggaaggg ccgagcgcag aagtggtcct gcaactttat    2940
ccgcctccat ccagtctatt aattgttgcc gggaagctag agtaagtagt tcgccagtta    3000
atagtttgcg caacgttgtt gccattgcta caggcatcgt ggtgtcacgc tcgtcgtttg    3060
gtatggcttc attcagctcc ggttcccaac gatcaaggcg agttacatga tcccccatgt    3120
tgtgcaaaaa agcggttagc tccttcggtc ctccgatcgt tgtcagaagt aagttggccg    3180
cagtgttatc actcatggtt atggcagcac tgcataattc tcttactgtc atgccatccg    3240
taagatgctt ttctgtgact ggtgagtact caaccaagtc attctgagaa tagtgtatgc    3300
ggcgaccgag ttgctcttgc ccggcgtcaa tacgggataa taccgcgcca catagcagaa    3360
ctttaaaagt gctcatcatt ggaaaacgtt cttcggggcg aaaactctca aggatcttac    3420
cgctgttgag atccagttcg atgtaaccca ctcgtgcacc caactgatct tcagcatctt    3480
ttactttcac cagcgtttct gggtgagcaa aaacaggaag gcaaaatgcc gcaaaaaagg    3540
gaataagggc gacacggaaa tgttgaatac tcatactctt ccttttttcaa tattattgaa    3600 gcatttatca gggttattgt ctcatgagcg gatacatatt tgaatgtatt tagaaaaata    3660
```

```
aacaaatagg ggttccgcgc acatttcccc gaaaagtgcc acctgacgtc taagaaacca    3720
ttattatcat gacattaacc tataaaaata ggcgtatcac gaggccctaa attgtaaacg    3780
ttaatatttt gttaaaattc gcgttaaatt tttgttaaat cagctcattt tttaaccaat    3840
aggccgaaat cggcaaaatc ccttataaat caaaagaata gaccgagata gggttgagtg    3900
ttgttccagt ttggaacaag agtccactat taaagaacgt ggactccaac gtcaaagggc    3960
gaaaaaccgt ctatcagggc gatggcccac tacgtgaacc atcaccctaa tcaagttttt    4020
tggggtcgag gtgccgtaaa gcactaaatc ggaaccctaa agggagcccc cgatttagag    4080
cttgacgggg aaagccggcg aacgtggcga aaaggaagg gaagaaagcg aaaggagcgg    4140
gcgctagggc gctggcaagt gtagcggtca cgctgcgcgt aaccaccaca cccgccgcgc    4200
ttaatgcgcc gctacagggc gcgtaggccc tttcgtc                            4237

<210> SEQ ID NO 37
<211> LENGTH: 4240
<212> TYPE: DNA
<213> ORGANISM: Artificial Sequence
<220> FEATURE:
<223> OTHER INFORMATION: pAquoKin expression vector backbone

<400> SEQUENCE: 37
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgtt cagatctcct ttcagcaaaa aacccctcaa gacccgttta gaggccccaa     240
ggggttatgc tagttattgc tcagcggtgg cagcagccta ggttaattaa gctacgctag     300
tttaagcgct cttatcgtcg tcatccttgt aatcaccctc gagtgcggcc gcaagcttgg     360
taccgatatc ctcccaattg ggatccgac tcttgtcgtc gtcatcattc gaaccggcac     420
cgtggtgatg gtgatggtgt gccatggtat atctccttct taaagttaaa caaaattatt     480
tctagagggg aattgttatc cgctcacaat tcccctatag tgagtcgtat taattcgcgg     540
tcgaccagct gcattaatga atcggccaac gcgcggggag aggcggtttg cgtattgggc     600
gctcttccgc tgacaccatc gaatggcgca aaacctttcg cggtatggca tgatagcgcc     660
cggaagagag tcaattcagg gtggtgaatg tgaaaccagt aacgttatac gatgtcgcag     720
agtatgccgg tgtctcttat cagaccgttt cccgcgtggt gaaccaggcc agccacgttt     780
ctgcgaaaac gcgggaaaaa gtggaagcgg cgatggcgga gctgaattac attcccaacc     840
gcgtggcaca caactggcg gcaaacagt cgttgctgat tggcgttgcc acctccagtc     900
tggccctgca cgcgccgtcg caaattgtcg cggcgattaa atctcgcgcc gatcaactgg     960
gtgccagcgt ggtggtgtcg atggtagaac gaagcggcgt cgaagcctgt aaagcggcgg    1020
tgcacaatct tctcgcgcaa cgcgtcagtg ggctgatcat taactatccg ctggatgacc    1080
aggatgccat tgctgtggaa gctgcctgca ctaatgttcc ggcgttattt cttgatgtct    1140
ctgaccagac acccatcaac agtattattt tctcccatga agacggtacg cgactgggcg    1200
tggagcatct ggtcgcattg ggtcaccagc aaatcgcgct gttagcgggc ccattaagtt    1260
ctgtctcggc gcgtctgcgt ctggctggct ggcataaata tctcactcgc aatcaaattc    1320
agccgatagc ggaacgggaa ggcgactgga gtgccatgtc cggttttcaa caaaccatgc    1380
aaatgctgaa tgagggcatc gttcccactg cgatgctggt tgccaacgat cagatggcgc    1440
tgggcgcaat gcgcgccatt accgagtccg ggctgcgcgt tggtgcggac atctcggtag    1500
```

```
tgggatacga cgataccgaa gacagctcat gttatatccc gccgttaacc accatcaaac  1560
aggattttcg cctgctgggg caaaccagcg tggaccgctt gctgcaactc tctcagggcc  1620
aggcggtgaa gggcaatcag ctgttgcccg tctcactggt gaaaagaaaa accaccctgg  1680
cgcccaatac gcaaaccgcc tctccccgcg cgttggccga ttcattaatg cagctggcac  1740
gacaggtttc ccgactggaa agcgggcagt gagctcttcc gctatcctcg ctcactgact  1800
cgctgcgctc ggtcgttcgg ctgcggcgag cggtatcagc tcactcaaag gcggtaatac  1860
ggttatccac agaatcaggg gataacgcag gaaagaacat gtgagcaaaa ggccagcaaa  1920
aggccaggaa ccgtaaaaag gccgcgttgc tggcgttttt ccataggctc cgcccccctg  1980
acgagcatca caaaaatcga cgctcaagtc agaggtggcg aaacccgaca ggactataaa  2040
gataccaggc gtttccccct ggaagctccc tcgtgcgctc tcctgttccg accctgccgc  2100
ttaccggata cctgtccgcc tttctccctt cgggaagcgt ggcgctttct catagctcac  2160
gctgtaggta tctcagttcg gtgtaggtcg ttcgctccaa gctgggctgt gtgcacgaac  2220
cccccgttca gcccgaccgc tgcgccttat ccggtaacta tcgtcttgag tccaacccgg  2280
taagacacga cttatcgcca ctggcagcag ccactggtaa caggattagc agagcgaggt  2340
atgtaggcgg tgctacagag ttcttgaagt ggtggcctaa ctacggctac actagaagga  2400
cagtatttgg tatctgcgct ctgctgaagc cagttacctt cggaaaaaga gttggtagct  2460
cttgatccgg caaacaaacc accgctggta gcggtggttt ttttgtttgc aagcagcaga  2520
ttacgcgcag aaaaaaagga tctcaagaag atcctttgat cttttctacg ggtctgacg  2580
ctcagtggaa cgaaaactca cgttaaggga ttttggtcat gagattatca aaaaggatct  2640
tcacctagat ccttttaaat taaaaatgaa gttttaaatc aatctaaagt atatatgagt  2700
aaacttggtc tgacagttac caatgcttaa tcagtgaggc acctatctca gcgatctgtc  2760
tatttcgttc atccatagtt gcctgactcc ccgtcgtgta gataactacg atacgggagg  2820
gcttaccatc tggccccagt gctgcaatga taccgcgaga cccacgctca ccggctccag  2880
atttatcagc aataaaccag ccagccggaa gggccgagcg cagaagtggt cctgcaactt  2940
tatccgcctc catccagtct attaattgtt gccgggaagc tagagtaagt agttcgccag  3000
ttaatagttt gcgcaacgtt gttgccattg ctacaggcat cgtggtgtca cgctcgtcgt  3060
ttggtatggc ttcattcagc tccggttccc aacgatcaag gcgagttaca tgatccccca  3120
tgttgtgcaa aaaagcggtt agctccttcg gtcctccgat cgttgtcaga agtaagttgg  3180
ccgcagtgtt atcactcatg gttatggcag cactgcataa ttctcttact gtcatgccat  3240
ccgtaagatg cttttctgtg actggtgagt actcaaccaa gtcattctga aatagtgta  3300
tgcggcgacc gagttgctct tgcccggcgt caatacggga taataccgcg ccacatagca  3360
gaactttaaa agtgctcatc attggaaaac gttcttcggg gcgaaaactc tcaaggatct  3420
taccgctgtt gagatccagt tcgatgtaac ccactcgtgc acccaactga tcttcagcat  3480
cttttacttt caccagcgtt tctgggtgag caaaaacagg aaggcaaaat gccgcaaaaa  3540
agggaataag ggcgacacgg aaatgttgaa tactcatact cttccttttt caatattatt  3600
gaagcattta tcagggttat tgtctcatga gcggatacat atttgaatgt atttagaaaa  3660
ataaacaaat aggggttccg cgcacatttc cccgaaaagt gccacctgac gtctaagaaa  3720
ccattattat catgacatta acctataaaa ataggcgtat cacgaggccc taaattgtaa  3780
acgttaatat tttgttaaaa ttcgcgttaa attttttgtta aatcagctca ttttttaacc  3840
aataggccga atcggcaaa atcccttata aatcaaaaga atagaccgag atagggttga  3900
```

-continued

```
gtgttgttcc agtttggaac aagagtccac tattaaagaa cgtggactcc aacgtcaaag    3960
ggcgaaaaac cgtctatcag ggcgatggcc cactacgtga accatcaccc taatcaagtt    4020
ttttggggtc gaggtgccgt aaagcactaa atcggaaccc taaagggagc cccgattta     4080 gagcttgacg gggaaagccg gcgaacgtgg cgagaaagga agggaagaaa gcgaaaggag    4140
cgggcgctag ggcgctggca agtgtagcgg tcacgctgcg cgtaaccacc acacccgccg    4200
cgcttaatgc gccgctacag ggcgcgtagg ccctttcgtc                          4240
```

<210> SEQ ID NO 38
<211> LENGTH: 120
<212> TYPE: PRT
<213> ORGANISM: Artificial Sequence
<220> FEATURE:
<223> OTHER INFORMATION: Randomly generated sequence, created by ExPASy
   WWW server tool

<400> SEQUENCE: 38

Glu Pro Pro Ser Glu Pro Glu Ser Glu Glu Ser Glu Pro Glu Glu Pro
1               5                   10                  15

Gln Ser Ser Gln Pro Pro Pro Ser Glu Pro Gln Gln Pro Ser Gln
            20                  25                  30

Gln Pro Gln Gln Pro Ser Pro Glu Gln Pro Ser Gln Pro Glu Gln Pro
        35                  40                  45

Glu Pro Gln Ser Glu Pro Gln Gln Pro Glu Gln Pro Gln Pro Pro Gln
    50                  55                  60

Pro Pro Pro Pro Glu Gln Ser Pro Ser Pro Pro Glu Ser Gln Ser Gln
65                  70                  75                  80

Ser Ser Ser Pro Ser Pro Gln Gln Pro Ser Pro Glu Pro Ser Ser Ser
                85                  90                  95

Ser Gln Pro Glu Gln Pro Glu Pro Pro Gln Glu Pro Glu Ser Pro Glu
            100                 105                 110

Pro Pro Pro Gln Pro Gln Glu Gln
        115                 120

<210> SEQ ID NO 39
<211> LENGTH: 120
<212> TYPE: PRT
<213> ORGANISM: Artificial Sequence
<220> FEATURE:
<223> OTHER INFORMATION: Randomly generated sequence, created by ExPASy
   WWW server tool

<400> SEQUENCE: 39

Pro Glu Pro Glu Pro Gln Pro Ser Pro Gln Ser Pro Ser Pro Pro
1               5                   10                  15

Pro Pro Pro Pro Pro Pro Ser Gln Pro Pro Gln Pro Ser Pro Pro Pro
            20                  25                  30

Ser Glu Pro Glu Pro Pro Pro Glu Ser Pro Gln Pro Pro Pro Gln
        35                  40                  45

Gln Pro Pro Ser Pro Gln Ser Pro Ser Pro Gln Pro Pro
    50                  55                  60

Ser Pro Pro Pro Pro Pro Gln Pro Gln Pro Gln Ser Glu Pro Gln
65                  70                  75                  80

Pro Pro Gln Pro Glu Pro Pro Ser Ser Pro Pro Gln Glu Ser
            85                  90                  95

Gln Glu Gln Pro Ser Glu Pro Pro Pro Pro Ser Glu Pro Ser Ser
        100                 105                 110

Glu Glu Pro Pro Ser Pro Pro Pro

<210> SEQ ID NO 40
<211> LENGTH: 120
<212> TYPE: PRT
<213> ORGANISM: Artificial Sequence
<220> FEATURE:
<223> OTHER INFORMATION: Randomly generated sequence, created by ExPASy
       WWW server tool

<400> SEQUENCE: 40

Pro Gln Glu Glu Pro Glu Gln Ser Pro Gln Pro Glu Pro Pro Pro
 1               5                  10                  15

Pro Gln Gln Gln Ser Glu Pro Glu Ser Glu Glu Ser Glu Gln Pro
                20                  25                  30

Glu Pro Ser Pro Pro Pro Pro Gln Glu Ser Glu Ser Gln Gln Glu
             35                  40                  45

Ser Glu Pro Gln Pro Pro Ser Pro Ser Glu Pro Pro Glu Ser Ser
 50                  55                  60

Pro Glu Glu Pro Pro Glu Glu Pro Ser Gln Gln Glu Glu Pro Glu
 65                  70                  75                  80

Ser Glu Pro Ser Glu Ser Glu Ser Pro Pro Gln Glu Pro Ser Ser
                 85                  90                  95

Glu Pro Glu Gln Pro Gln Pro Glu Gln Pro Ser Glu Glu Glu Gln
                100                 105                 110

Pro Gln Glu Glu Pro Glu Gln Glu
        115                 120

<210> SEQ ID NO 41
<211> LENGTH: 120
<212> TYPE: PRT
<213> ORGANISM: Artificial Sequence
<220> FEATURE:
<223> OTHER INFORMATION: Randomly generated sequence, created by ExPASy
       WWW server tool

<400> SEQUENCE: 41

Pro Pro Gln Pro Pro Glu Pro Pro Glu Gly Gln Pro Pro Gly Gly
 1               5                  10                  15

Gly Pro Glu Pro Glu Gly Pro Pro Pro Pro Pro Pro Pro Pro Pro
                20                  25                  30

Pro Gln Gln Pro Gln Glu Gln Pro Pro Gly Pro Pro Gln Pro Glu Pro
         35                  40                  45

Gln Pro Pro Glu Pro Pro Glu Pro Gly Pro Pro Pro Gly Pro Pro
 50                  55                  60

Gln Pro Gln Pro Pro Gly Pro Gly Pro Glu Gly Pro Gly Pro Gln Pro
 65                  70                  75                  80

Gln Pro Pro Pro Pro Glu Pro Pro Glu Gly Gly Pro Pro Gln
                 85                  90                  95

Gln Pro Gln Pro Pro Glu Gln Glu Pro Gln Pro Glu  Glu Gly
             100                 105                 110

Pro Pro Gly Pro Gly Glu Pro Pro
        115                 120

<210> SEQ ID NO 42
<211> LENGTH: 120
<212> TYPE: PRT
<213> ORGANISM: Artificial Sequence
<220> FEATURE:
<223> OTHER INFORMATION: Randomly generated sequence, created by ExPASy
       WWW server tool

<400> SEQUENCE: 42

Glu Pro Gly Gln Pro Pro Gly Gly Pro Glu Glu Gln Glu Pro Pro
1               5                   10                  15

Glu Glu Glu Glu Glu Pro Pro Gln Glu Gln Pro Gln Glu Glu Gly
                20                  25                  30

Glu Pro Gln Gly Glu Glu Pro Gly Gly Glu Gln Gly Pro Glu Pro
            35                  40                  45

Gly Gln Pro Pro Pro Gln Pro Pro Gln Gly Pro Pro Gln Gly Gln
        50                  55                  60

Gly Glu Gln Glu Pro Gln Pro Gln Glu Gly Gln Pro Glu Gly
65                  70                  75                  80

Pro Glu Glu Pro Pro Gly Pro Gln Glu Glu Glu Pro Glu Pro
            85                  90                  95

Pro Glu Pro Pro Pro Gln Gly Gly Glu Glu Pro Gly Gln Pro Pro
        100                 105                 110

Pro Glu Glu Glu Gly Glu Gln Glu
        115                 120

<210> SEQ ID NO 43
<211> LENGTH: 120
<212> TYPE: PRT
<213> ORGANISM: Artificial Sequence
<220> FEATURE:
<223> OTHER INFORMATION: Randomly generated sequence, created by ExPASy
      WWW server tool

<400> SEQUENCE: 43

Glu Pro Glu Pro Gly Glu Gly Glu Glu Pro Gln Glu Glu Gln Gly Pro
1               5                   10                  15

Glu Glu Pro Gly Gln Glu Glu Gly Glu Glu Glu Glu Glu Glu Gly Glu
                20                  25                  30

Pro Pro Gln Gly Pro Gln Gln Glu Glu Pro Glu Gly Pro Pro Glu
            35                  40                  45

Glu Gln Gln Glu Pro Pro Pro Glu Gln Pro Glu Pro Glu Glu Pro Pro
        50                  55                  60

Glu Gly Pro Pro Pro Glu Glu Glu Gly Glu Glu Gly Glu Glu Gln Pro
65                  70                  75                  80

Gln Gly Pro Glu Glu Gly Gln Glu Glu Pro Gln Pro Glu Gly Gly Pro
            85                  90                  95

Gly Pro Pro Glu Glu Pro Pro Glu Glu Pro Gln Glu Gly Glu Pro
        100                 105                 110

Pro Glu Glu Glu Glu Glu Pro Glu
        115                 120

<210> SEQ ID NO 44
<211> LENGTH: 250
<212> TYPE: PRT
<213> ORGANISM: Artificial Sequence
<220> FEATURE:
<223> OTHER INFORMATION: Randomly generated sequence, created by ExPASy
      WWW server tool

<400> SEQUENCE: 44

Glu Glu Gln Pro Glu Pro Pro Gln Ser Glu Gln Glu Asp Pro Glu Glu
1               5                   10                  15

Pro Gly Ser Ser Gln Gly Glu Pro Gly Pro Pro Glu Gln Ser Pro Gly
                20                  25                  30

Gly Pro Pro Glu Glu Pro Asp Gln Pro Ser Glu Glu Pro Pro Pro Glu

```
                     35                  40                  45
Glu Pro Gln Pro Gln Ser Glu Gly Ser Pro Gly Pro Pro Glu Gly
 50                      55                  60

Pro Pro Glu Pro Asp Pro Glu Asp Glu Ser Glu Pro Gln Gln
 65                  70                  75                  80

Pro Pro Ser Gln Pro Ser Pro Ser Glu Gly Gln Pro Glu Pro
                 85                  90                  95

Pro Gln Glu Gln Ser Ser Ser Glu Glu Ser Gly Pro Ser Glu Pro
            100                 105                 110

Ser Ser Asp Pro Ser Ser Glu Glu Ser Asp Pro Pro Glu Pro Ser Pro
            115                 120                 125

Ser Pro Pro Pro Ser Glu Gly Ser Ser Glu Pro Pro Gln Gln Pro Asp
130                 135                 140

Asp Pro Ser Pro Pro Gly Glu Pro Gln Pro Glu Gln Pro Glu Pro
145                 150                 155                 160

Gly Ser Pro Asp Asp Gln Ser Pro Pro Ser Pro Ser Pro Gly
                165                 170                 175

Glu Pro Gln Gly Gln Pro Asp Gly Ser Pro Ser Gly Glu Pro Gly Gln
            180                 185                 190

Ser Glu Glu Pro Gln Pro Gly Gly Asp Pro Glu Pro Ser Pro Pro Gly
            195                 200                 205

Gln Glu Glu Pro Pro Glu Pro Ser Pro Glu Gly Pro Ser Glu Gly
            210                 215                 220

Ser Pro Gly Glu Pro Pro Ser Pro Pro Gly Ser Asp Pro Glu Ser Asp
225                 230                 235                 240

Gly Gly Pro Gln Pro Pro Gln Asp Gln Gln
                245                 250

<210> SEQ ID NO 45
<211> LENGTH: 250
<212> TYPE: PRT
<213> ORGANISM: Artificial Sequence
<220> FEATURE:
<223> OTHER INFORMATION: Randomly generated sequence, created by ExPASy
      WWW server tool

<400> SEQUENCE: 45

Glu Glu Gln Pro Glu Pro Ile Val Ser Glu Gln Glu Asp Pro Glu Glu
  1               5                  10                  15

Pro Gly Ser Ser Val Phe Glu Ile Leu Pro Pro Glu Gln Ser Pro Gly
                 20                  25                  30

Gly Pro Pro Glu Glu Pro Asp Gln Pro Ser Glu Glu Pro Val Met Glu
            35                  40                  45

Glu Ile Gln Pro Gln Leu Glu Gly Ser Pro Gly Pro Pro Glu Gly
 50                      55                  60

Pro Pro Glu Pro Asp Pro Glu Asp Glu Ser Glu Glu Ile Gln Gln
 65                  70                  75                  80

Pro Ile Ser Gln Pro Ser Pro Ser Glu Gly  Gln Leu Leu Glu Pro
                 85                  90                  95

Leu Gln Glu Gln Ser Ser Ser Glu Glu Ser Gly Pro Ser Glu Pro
            100                 105                 110

Ser Ser Asp Pro Ser Ser Glu Glu Ser Asp Pro Glu Pro Leu Ile
            115                 120                 125

Ser Val Phe Pro Ser Glu Gly Ser Ser Glu Pro Pro Gln Gln Pro Asp
130                 135                 140

Asp Leu Ser Pro Pro Leu Glu Pro Gln Pro Glu Glu Gln Pro Glu Pro
```

```
                145                 150                 155                 160
Gly Ser Pro Asp Asp Gln Ser Pro Pro Ser Pro Ser Pro Pro Gly
                165                 170                 175
Glu Pro Gln Gly Gln Pro Asp Gly Ser Pro Ser Gly Glu Pro Gly Gln
                180                 185                 190
Ser Glu Glu Pro Gln Pro Gly Gly Asp Pro Glu Ile Val Pro Pro Ile
        195                 200                 205
Gln Glu Glu Leu Pro Glu Pro Ser Pro Glu Gly Ser Pro Leu Glu Gly
        210                 215                 220
Ser Ile Gly Glu Met Val Ser Pro Pro Gly Ser Asp Pro Glu Ser Asp
225                 230                 235                 240
Gly Gly Pro Gln Pro Pro Gln Asp Gln Gln
                245                 250

<210> SEQ ID NO 46
<211> LENGTH: 360
<212> TYPE: DNA
<213> ORGANISM: Artificial Sequence
<220> FEATURE:
<223> OTHER INFORMATION: Sequence is produced using the reverse
      translation tool located at:
      www.vivo.colostate.edu/molkit/rtranslate/index.html.

<400> SEQUENCE: 46
gaaccgccga gcgaaccgga aagcgaagaa agcgaaccgg aagaaccgca gagcagccag      60
ccgccgccgc cgagcgaacc gcagcagccg agccagcagc cgcagcagcc gagcccggaa     120
cagccgagcc agccggaaca gccggaaccg cagagcgaac cgcagcagcc ggaacagccg     180
cagccgccgc agccgccgcc gccggaacag agcccgagcc cgccggaaag ccagagccag     240
agcagcagcc cgagcccgca gcagccgagc ccggaaccga gcagcagcag ccagccggaa     300
cagccggaac cgccgcagga accggaaagc ccggaaccgc cgccgcagcc gcaggaacag     360

<210> SEQ ID NO 47
<211> LENGTH: 360
<212> TYPE: DNA
<213> ORGANISM: Artificial Sequence
<220> FEATURE:
<223> OTHER INFORMATION: Sequence is produced using the reverse
      translation tool located at:
      www.vivo.colostate.edu/molkit/rtranslate/index.html.

<400> SEQUENCE: 47
ccggaaccgg aaccgcagcc gccgagcccg cagagcccga gccgccgcc gccgccgccg       60 ccgccgagcc agccgccgca gccgagcccg ccgccgagcg aaccggaacc gccgccgccg     120
gaaagcccgc agccgccgcc gcagcagccg ccgccgagcc gcagagcccg agcccgccg     180 cagccgccgc cgagcccgcc gccgccgccg cagccgcagc cgccgcagag cgaaccgcag     240
ccgccgcagc cggaaccgcc gccgagcagc ccgccgccgc aggaaagcca ggaacagccg     300
agcgaaccgc cgccgccgcc gagcgaaccg agcagcgaag aaccgccgag cccgccgccg     360

<210> SEQ ID NO 48
<211> LENGTH: 360
<212> TYPE: DNA
<213> ORGANISM: Artificial Sequence
<220> FEATURE:
<223> OTHER INFORMATION: Sequence is produced using the reverse
      translation tool located at:
      www.vivo.colostate.edu/molkit/rtranslate/index.html.

<400> SEQUENCE: 48
```

-continued

```
ccgcaggaag aaccggaaca gagcccgcag ccggaagaac cgccgccgcc gcagcagcag    60
agcgaaccgg aaagcgaaga agaaagcgaa cagccggaac cgagcccgcc gccgccgccg   120
caggaaagcg aaagccagca ggaaagcgaa ccgcagccgc cgccgagccc gagcgaaccg   180
ccggaaagca gcccggaaga accgccggaa gaaccgagcc agcaggaaga agaaccggaa   240
agcgaaccga gcgaaagcga aagcccgccg gaacaggaac cgagcagcga accggaacag   300
ccgcagccgg aacagccgcc gagcgaagaa gaacagccgc aggaagaacc ggaacaggaa   360
```

<210> SEQ ID NO 49
<211> LENGTH: 360
<212> TYPE: DNA
<213> ORGANISM: Artificial Sequence
<220> FEATURE:
<223> OTHER INFORMATION: Sequence is produced using the reverse
      translation tool located at:
      www.vivo.colostate.edu/molkit/rtranslate/index.html.

<400> SEQUENCE: 49

```
ccgccgcagc cgccggaacc gccggaaggc cagccgccgc cgggcggcgg cccggaaccg    60
gaaggcccgc cgccgccgcc gccgccgccg ccgccgccgc agcagccgca ggaacagccg   120
ccgggcccgc cgcagccgga accgcagccg ccggaaccgc cggaaccggg cccgccgccg   180
ccgggcccgc cgcagccgca gccgccgggc ccgggcccgg aaggcccggg cccgcagccg   240
cagccgccgc cgccgccgga accgccggaa ggcggcccgc cgccgcagca gccgcagccg   300
ccggaacagg aaccgcagcc ggaaccggaa gaaggcccgc cgggcccggg cgaaccgccg   360
```

<210> SEQ ID NO 50
<211> LENGTH: 360
<212> TYPE: DNA
<213> ORGANISM: Artificial Sequence
<220> FEATURE:
<223> OTHER INFORMATION: Sequence is produced using the reverse
      translation tool located at:
      www.vivo.colostate.edu/molkit/rtranslate/index.html.

<400> SEQUENCE: 50

```
gaaccgggcc agccgccgcc gggcggcccg gaagaacagg aaccgccgga agaagaagaa    60
gaaccgccgc aggaacagcc gcaggaagaa gaaggcgaac cgcagggcga agaaccgggc   120
ggcggcgaac agggcccgga accgggccag ccgccgccgc agccgccgca gggcccgccg   180
ccgcagggcc agggcgaaca ggaaccgcag ccggaacagg aagaaggcca gccggaaggc   240
ccggaagaac cgccgggccc gcaggaagaa gaagaaccgg aagaaccgcc ggaaccgccg   300
ccgcagggcg gcgaagaacc gggccagccg ccgccgccgg aagaagaagg cgaacaggaa   360
```

<210> SEQ ID NO 51
<211> LENGTH: 360
<212> TYPE: DNA
<213> ORGANISM: Artificial Sequence
<220> FEATURE:
<223> OTHER INFORMATION: Sequence is produced using the reverse
      translation tool located at:
      www.vivo.colostate.edu/molkit/rtranslate/index.html.

<400> SEQUENCE: 51

```
gaaccggaac cgggcgaagg cgaagaaccg caggaagaac agggcccgga agaaccgggc    60
caggaagaag gcgaagaaca ggaagaagaa ggcgaaccgc cgcagggccc gcagcagcag   120
gaagaaccgg aaggcccgcc ggaagaacag caggaaccgc cgccggaaca gccggaaccg   180
gaagaaccgc cggaaggccc gccgccggaa gaagaaggcg aagaaggcga agaacagccg   240
```

```
cagggcccgg aagaaggcca gcaggaaccg cagccggaag gcggcccggg cccgccggaa    300
gaaccgccgg aagaaccgcc gcaggaaggc gaaccgccgg aagaagaaga agaaccggaa    360
```

<210> SEQ ID NO 52
<211> LENGTH: 750
<212> TYPE: DNA
<213> ORGANISM: Artificial Sequence
<220> FEATURE:
<223> OTHER INFORMATION: Sequence is produced using the reverse
      translation tool located at:
      www.vivo.colostate.edu/molkit/rtranslate/index.html.

<400> SEQUENCE: 52

```
gaagaacagc cggaaccgcc gcagagcgaa caggaagatc cggaagaacc gggtagctct     60
cagggtgaac cggtccgcc ggaacagtct ccgggcggtc cgccggaaga accgaccag     120 ccgtctgaag aaccgccgcc ggaagaaccg cagccgcagt ctgaaggtag cccgggcccg    180
ccgccggaag gcccgccgga accgaccccg gaagaagatg aaagcgaaga accgcagcaa    240
ccgccgtctc agccgagtcc gccgtctgaa ggccagccgc cggaaccgcc gcaagaacag    300
agttctagca gcgaagaatc tggtccgagc gaaccgagct ctgatccgag ttctgaagaa    360
agcgacccgc cggaaccgtc tccgagcccg ccgccgagtg aaggtagctc tgaaccgccg    420
cagcagccgg atgatccgtc gccgccgggc gaaccgcagc cggaagaaca accgaaccg    480 ggttctccgg atgatcagag cccgccgccg tcgccgagcc cgccgggtga accgcagggt    540
caaccggacg gctctccgag cggtgaaccg ggtcagagcg aagaaccgca accgggtggc    600
gatccggaac cgagcccgcc gggccaggaa gaaccgccgg aaccgtcacc ggaaggttct    660
ccgtcagaag gttcgccggg tgaaccgccg tctccgccgg gttctgaccc ggaatctgat    720
ggtggcccgc agccgccgca ggatcaacag                                    750
```

<210> SEQ ID NO 53
<211> LENGTH: 750
<212> TYPE: DNA
<213> ORGANISM: Artificial Sequence
<220> FEATURE:
<223> OTHER INFORMATION: Sequence is produced using the reverse
      translation tool located at:
      www.vivo.colostate.edu/molkit/rtranslate/index.html.

<400> SEQUENCE: 53

```
gaagaacagc cggaaccgat cgtgagcgaa caggaagatc cggaagaacc gggtagctcg     60
gtgtttgaaa ttctgccgcc ggaacagagc ccggtggtc cgccggaaga accggatcaa    120
ccgtctgaag aaccggtgat ggaagaaatt caaccgcagc tggaaggctc tccgggtccg    180
ccgccggaag gtccgccgga accgaccccg gaagaagatg aatccgaaga aattcagcaa    240
ccgattagcc aaccgtctcc gccgagcgaa ggtcaactgc tggaaccgct gcaggaacag    300
tctagttcgt ccgaagaaag cggtccgtct gaaccgtcga gcgacccgag ctcggaagaa    360
agcgacccgc cggaaccgct gatctctgtc tttccgagtg aaggttctag cgaaccgccg    420
caacagccgg atgacctgtc gccgccgctg aaccgcagc cggaagaaca accgaaccg    480 ggttcgccgg acgatcagtc tccgccgccg tctccgagcc cgccgggtga accgcagggt    540
cagccggatg gtagcccgtc tggtgaaccg ggtcaaagtg aagaaccgca gccgggtggc    600
gatccggaaa tcgttccgcc gattcaggaa gaactgccgg aaccgagccc ggaaggttct    660
ccgctggaag ttctattggg tgaaatggtc tcaccgccgg ttctgatcc ggaaagcgat    720 ggtggtccgc agccgccgca ggatcagcaa                                    750
```

<210> SEQ ID NO 54
<211> LENGTH: 375
<212> TYPE: DNA
<213> ORGANISM: Artificial Sequence
<220> FEATURE:
<223> OTHER INFORMATION: Double stranded sequence of the
      expression/cloning region of the pAquoProt plasmid

<400> SEQUENCE: 54
tcgatcagct ggtcgaccgc gaattaatac gactcactat agggaattg tgagcggata      60 acaattcccc tctagaaata attttgttta actttaagaa ggagatatac catggcacac    120
catcaccatc accacggtgc cggttcgaat gatgacgacg acaagagtcc ggatcccaat    180
tgggaggata tcggtaccaa gcttgcggcc gcactcgagg gttacccata cgatgttcca    240
gattacgctt aaactagcgt agcttaatta acctaggctg ctgccaccgc tgagcaataa    300
ctagcataac cccttgggc ctctaaacgg gtcttgaggg gttttttgct gaaaggagat    360
ctgaacatat gccgg                                                     375

<210> SEQ ID NO 55
<211> LENGTH: 375
<212> TYPE: DNA
<213> ORGANISM: Artificial Sequence
<220> FEATURE:
<223> OTHER INFORMATION: Double stranded sequence of the
      expression/cloning region of the pAquoProt plasmid

<400> SEQUENCE: 55
ccggcatatg ttcagatctc ctttcagcaa aaaaccctc aagacccgtt tagaggcccc       60
aaggggttat gctagttatt gctcagcggt ggcagcagcc taggttaatt aagctacgct    120
agtttaagcg taatctggaa catcgtatgg gtaaccctcg agtgcggccg caagcttggt    180
accgatatcc tcccaattgg gatccggact cttgtcgtcg tcatcattcg aaccggcacc    240
gtggtgatgg tgatggtgtg ccatggtata tctccttctt aaagttaaac aaaattattt    300
ctagagggga attgttatcc gctcacaatt cccctatagt gagtcgtatt aattcgcggt    360
cgaccagctg atcga                                                    375

<210> SEQ ID NO 56
<211> LENGTH: 46
<212> TYPE: PRT
<213> ORGANISM: Artificial Sequence
<220> FEATURE:
<223> OTHER INFORMATION: pAquoProt plasmid coding sequences for a 6xHis
      tag, enterokinase (EK) cleavage site, multicloning
      site, and HA epitope tag

<400> SEQUENCE: 56

Met Ala His His His His His His Gly Ala Gly Ser Asn Asp Asp Asp
1               5                   10                  15

Asp Lys Ser Pro Asp Pro Asn Trp Glu Asp Ile Gly Thr Lys Leu Ala
            20                  25                  30

Ala Ala Leu Glu Gly Tyr Pro Tyr Asp Val Pro Asp Tyr Ala
        35                  40                  45

<210> SEQ ID NO 57
<211> LENGTH: 380
<212> TYPE: DNA
<213> ORGANISM: Artificial Sequence
<220> FEATURE:
<223> OTHER INFORMATION: Double stranded sequence of the
      expression/cloning region of the pAquoKin plasmid

```
<400> SEQUENCE: 57
tcgatcagct ggtcgaccgc gaattaatac gactcactat aggggaattg tgagcggata      60
acaattcccc tctagaaata attttgttta actttaagaa ggagatatac catggcacac     120
catcaccatc accacggtgc cggttcgaat gatgacgacg acaagagtcc ggatcccaat     180
tgggaggata tcggtaccaa gcttgcggcc gcactcgagg gtgattacaa ggatgacgac     240
gataagagcg cttaaactag cgtagcttaa ttaacctagg ctgctgccac cgctgagcaa     300
taactagcat aaccccttgg ggcctctaaa cgggtcttga ggggttttt gctgaaagga      360 gatctgaaca tatgccggat                                                 380

<210> SEQ ID NO 58
<211> LENGTH: 380
<212> TYPE: DNA
<213> ORGANISM: Artificial Sequence
<220> FEATURE:
<223> OTHER INFORMATION: Double stranded sequence of the
      expression/cloning region of the pAquoKin plasmid

<400> SEQUENCE: 58
atccggcata tgttcagatc tcctttcagc aaaaaacccc tcaagacccg tttagaggcc      60
ccaaggggtt atgctagtta ttgctcagcg gtggcagcag cctaggttaa ttaagctacg     120
ctagtttaag cgctcttatc cagcagtagg aacattagac cctcgagtgc ggccgcaagc     180
ttggtaccga tatcctccca attgggatcc ggactcttgt cgtcgtcatc attcgaaccg     240
gcaccgtggt gatggtgatg gtgtgccatg gtatatctcc ttcttaaagt taaacaaaat     300
tatttctaga ggggaattgt tatccgctca caattcccct atagtgagtc gtattaattc     360
gcggtcgacc agctgatcga                                                 380

<210> SEQ ID NO 59
<211> LENGTH: 47
<212> TYPE: PRT
<213> ORGANISM: Artificial Sequence
<220> FEATURE:
<223> OTHER INFORMATION: pAquoKin plasmid coding sequences for a 6xHis
      tag, enterokinase cleavage site, multicloning site, and
      the FLAG epitope tag

<400> SEQUENCE: 59

Met Ala His His His His His His Gly Ala Gly Ser Asn Asp Asp Asp
1               5                   10                  15

Asp Lys Ser Pro Asp Pro Asn Trp Glu Asp Ile Gly Thr Lys Leu Ala
            20                  25                  30

Ala Ala Leu Glu Gly Asp Tyr Lys Asp Asp Asp Asp Lys Ser Ala
        35                  40                  45
```